(12) United States Patent
Sukits et al.

(10) Patent No.: US 7,379,820 B2
(45) Date of Patent: May 27, 2008

(54) SOLUTION STRUCTURE OF RIP DD AND USES THEREOF

(75) Inventors: Steven F. Sukits, Arlington, MA (US); Jean-Baptiste Telliez, Waltham, MA (US); Lih-Ling Lin, Concord, MA (US); Guang-Yi Xu, Medford, MA (US)

(73) Assignee: Wyeth, Madison, NJ (US)

( * ) Notice: Subject to any disclaimer, the term of this patent is extended or adjusted under 35 U.S.C. 154(b) by 541 days.

(21) Appl. No.: 10/359,439

(22) Filed: Feb. 6, 2003

(65) Prior Publication Data

US 2003/0220481 A1 Nov. 27, 2003

Related U.S. Application Data

(60) Provisional application No. 60/356,391, filed on Feb. 11, 2002.

(51) Int. Cl.
*G06F 19/00* (2006.01)
*A61K 38/00* (2006.01)
*C07K 1/00* (2006.01)

(52) U.S. Cl. .................. 702/19; 530/300; 530/350
(58) Field of Classification Search .............. None
See application file for complete search history.

(56) References Cited

U.S. PATENT DOCUMENTS

| 5,674,734 | A | 10/1997 | Leder et al. | |
| 6,355,780 | B1 * | 3/2002 | Wallach et al. | .......... 530/389.1 |
| 2002/0094540 | A1 | 7/2002 | Tsao et al. | |
| 2002/0123117 | A1 * | 9/2002 | Wallach et al. | ............. 435/184 |

FOREIGN PATENT DOCUMENTS

WO WO9625941 * 8/1996

OTHER PUBLICATIONS

Arch et al., "Tumor necrosis factor receptor-associated factors (TRAFs)—a family of adapter proteins that regulates life and death," Genes & Development, 12, 2821-2830, 1988.
Boldin et al., "Self-association of the "Death Domains" of the p55 Tumor Necrosis Factor (TNF) Receptor and Fas/APO1 Prompts Signaling for TNF and Fas/APO1 Effects," The Journal of Biological Chemistry, 270 (1), 387-391, 1995.
Chou et al., "Solution Structure of the RAIDD CARD and Model for CARD/CARD Interaction in Caspase-2 and Caspase-9 Recruitment," Cell, 94, 171-180, 1988.
Day et al., "Solution Structure and mutagenesis of the caspase recruitment domain (CARD) from Apaf-1," Cell Death and Differentiation, 6, 1125-1132, 1999.
Duan et al, "RAIDD is a new 'death' adaptor molecule," Nature, 385, 86-89, Jan. 1997.
Eberstadt et al., "NMR structure and mutagenesis of the FADD (Mort1) death-effector domain," Nature, 392, 941-945, 1998.

Eck et al., "Crystallization of Trimeric Recombinant Human Tumor Necrosis Factor (Cachectin)," The Journal of Biological Chemistry, 263 (26), 12816-12819,1988.
Feinstein et al., "The death domain: a module shared by proteins with diverse cellular functions," Tibs, 20, 342-344, 1995.
Grell et al., "TR60 and TR80 Tumor Necrosis Factor (TNF)-Receptors Can Independently Mediate Cytolysis," Lymphokine and Cytokine Research, 12, 143-148, 1992.
Hofmann et al., "The CARD domain: a new apoptotic signalling motif," TIBS, 22, 155-156, 1997.
Hsu et al., "The TNF Receptor 1-Associated Protein TRADD Signals Cell Death and NF-κB Activation," Cell, 81, 495-504, 1995.
Hsu et al, "TRADD—TRAF2 and TRADD-FADD Interactions Define Two Distinct TNF Receptor 1 Signal Transduction Pathways," Cell, 84, 299-308, 1996.
Hsu et al, "TNF-Dependent Recruitment of the Protein Kinase RIP to the TNF Receptor-1 Signaling Complex," Immunity, 4, 387-396, 1996.
Huang et al, "NMR structure and mutagenesis of the Fas (APO-1/CD95) death domain," Nature, 384, 638-641, 1996.
Jeong et al., "The Solution Structiure of FADD Death Domain," The Journal of Biological Chemistry, 274(23), 16337-16342, 1999.
Kelliher et al., "The Death Domain Kinase RIP Mediates the TNF-Induced NF—κB Signal," Immunity, 8, 297-303, 1998.
Kieser et al, "LMP1 signal transduction differs substantially from TNF receptor 1 signaling in the molecular functions of TRADD and TRAF2," The EMBO Journal, 18(9), 2511-2521, 1999.
Liepinsh et al., "NMR structure of the death domain of the p75 neurotrophin receptor," The EMBO Journal, 16 (16), 4999-5005, 1997.
McWhirter et al, "Crystallographic analysis of CD40 recognition and signaling by human TRAF2," Proc. Natl. Acad. Sci. USA, 96, 8408-8413, 1999.
Nakano et al., "TRAF5, an Activator of NF-κB and Putative Signal Transducer for the Lymphotoxin-β Receptor," The Journal of Biological Chemistry, 271 (25), 14661-14664, 1996.
Park et al., "Structural basis for self-association and receptor recognition of human TRAF2," Nature, 398, 533-538, 1999.
Pullen et al., "CD40-Tumor Necrosis Factor Receptor-Associated Factor (TRAF) Interactions: Regulation of CD40 Signaling through Multiple TRAF Binding Sites and TRAF Hetero-Oligomerization," Biochemistry, 37, 11836-11845, 1998.

(Continued)

*Primary Examiner*—Lori A. Clow
(74) *Attorney, Agent, or Firm*—Lowrie, Lando & Anastasi, LLP

(57) ABSTRACT

The present invention relates to the three dimensional solution structure of receptor interacting protein dead domain (RIP DD), as well as the identification and characterization of various binding active sites of RIP DD. Also provided for by the present invention are methods of utilizing the three dimensional structure for the design and selection of potent and selective inhibitors of TNF signaling pathways.

21 Claims, 44 Drawing Sheets

OTHER PUBLICATIONS

Qin et al., "Structural basis of procaspase-9 recruitment by the apoptotic protease-activating factor 1," Nature, 399, 549-557, 1999.

Sato et al., "A novel member of the TRAF family of putative signal transducing protein binds to the cytosolic domain of CD40," FEBS Letters, 358, 113-118, 1995.

Sioud et al., "Design of Nuclease Resistant Protein Kinase CαDNA Enzymes with Potential Therapeutic Application," J. Mol. Biol., 296, 937-947, 2000.

Stanger et al., "RIP: A Novel Protein Containing a Death Domain That Interacts with Fas/APO-1 (CD95) in Yeast and Causes Cell Death," Cell, 81, 513-523, 1995.

Sukits et al., "Solution Structure of the Tumor Necrosis Factor Receptor-1 Death Domain," J. Mol. Biol., 310, 895-906, 2001.

Tartaglia et al., "Tumor Necrosis Factor's Cytotoxic Activity Is Signaled by the p55 TNF Receptor," Cell, 73, 213-216, 1993.

Telliez et al., "Mutational Analysis and NMR studies of the Death Domain of the Tumor Necrosis Factor Receptor-1," J. Mol. Biol., 300, 1323-1333, 2000.

Vandevoorde et al., "Induced Expression of Trimerized Intracellular Domains of the Human Tumor Necrosis Factor (TNF) p55 Receptor Elicits TNF Effects," The Journal of Cell Biology, 137 (7), 1627-1638, 1997.

Xiao et al., "Three-Dimensional Structure of a Complex between the Death Domains of Pelle and Tube," Cell, 99, 545-555, 1999.

Zhou et al., "Solution Structure of Apaf-1 CARD and its interaction with caspase-9 CARD: A Structural basis for specific adaptor/caspase interaction," Proc. Natl. Acad. Sci. USA, 96, 11265-11270, 1999.

* cited by examiner

| | | ATOM TYPE | RESIDUE | | X | Y | Z | | | |
|---|---|---|---|---|---|---|---|---|---|---|
| ATOM | 1 | N | ASP | 588 | -24.559 | 5.578 | 1.890 | 1.00 | 7.58 | RIPD |
| ATOM | 2 | HN | ASP | 588 | -25.011 | 4.723 | 2.057 | 1.00 | 8.02 | RIPD |
| ATOM | 3 | CA | ASP | 588 | -23.104 | 5.722 | 2.177 | 1.00 | 6.78 | RIPD |
| ATOM | 4 | HA | ASP | 588 | -22.857 | 6.769 | 2.254 | 1.00 | 6.88 | RIPD |
| ATOM | 5 | CB | ASP | 588 | -22.772 | 5.021 | 3.497 | 1.00 | 7.05 | RIPD |
| ATOM | 6 | HB1 | ASP | 588 | -22.520 | 3.989 | 3.303 | 1.00 | 6.97 | RIPD |
| ATOM | 7 | HB2 | ASP | 588 | -23.628 | 5.066 | 4.155 | 1.00 | 7.69 | RIPD |
| ATOM | 8 | CG | ASP | 588 | -21.581 | 5.717 | 4.159 | 1.00 | 6.97 | RIPD |
| ATOM | 9 | OD1 | ASP | 588 | -21.786 | 6.768 | 4.743 | 1.00 | 7.13 | RIPD |
| ATOM | 10 | OD2 | ASP | 588 | -20.487 | 5.186 | 4.072 | 1.00 | 7.08 | RIPD |
| ATOM | 11 | C | ASP | 588 | -22.291 | 5.081 | 1.043 | 1.00 | 6.03 | RIPD |
| ATOM | 12 | O | ASP | 588 | -22.658 | 4.038 | 0.541 | 1.00 | 5.86 | RIPD |
| ATOM | 13 | N | PRO | 589 | -21.206 | 5.722 | 0.677 | 1.00 | 5.94 | RIPD |
| ATOM | 14 | CA | PRO | 589 | -20.343 | 5.187 | -0.406 | 1.00 | 5.55 | RIPD |
| ATOM | 15 | HA | PRO | 589 | -20.925 | 4.957 | -1.283 | 1.00 | 5.82 | RIPD |
| ATOM | 16 | CB | PRO | 589 | -19.379 | 6.334 | -0.699 | 1.00 | 6.18 | RIPD |
| ATOM | 17 | HB1 | PRO | 589 | -19.750 | 6.941 | -1.510 | 1.00 | 6.82 | RIPD |
| ATOM | 18 | HB2 | PRO | 589 | -18.396 | 5.948 | -0.935 | 1.00 | 6.01 | RIPD |
| ATOM | 19 | CG | PRO | 589 | -19.338 | 7.136 | 0.561 | 1.00 | 6.58 | RIPD |
| ATOM | 20 | HG1 | PRO | 589 | -19.162 | 8.176 | 0.332 | 1.00 | 7.37 | RIPD |
| ATOM | 21 | HG2 | PRO | 589 | -18.559 | 6.762 | 1.211 | 1.00 | 6.36 | RIPD |
| ATOM | 22 | CD | PRO | 589 | -20.683 | 6.984 | 1.223 | 1.00 | 6.59 | RIPD |
| ATOM | 23 | HD2 | PRO | 589 | -20.571 | 6.920 | 2.297 | 1.00 | 6.69 | RIPD |
| ATOM | 24 | HD1 | PRO | 589 | -21.334 | 7.801 | 0.954 | 1.00 | 7.24 | RIPD |
| ATOM | 25 | C | PRO | 589 | -19.588 | 3.949 | 0.087 | 1.00 | 4.78 | RIPD |
| ATOM | 26 | O | PRO | 589 | -19.885 | 3.408 | 1.133 | 1.00 | 4.88 | RIPD |
| ATOM | 27 | N | ILE | 590 | -18.615 | 3.493 | -0.656 | 1.00 | 4.42 | RIPD |
| ATOM | 28 | HN | ILE | 590 | -18.388 | 3.940 | -1.498 | 1.00 | 4.71 | RIPD |
| ATOM | 29 | CA | ILE | 590 | -17.850 | 2.287 | -0.217 | 1.00 | 4.07 | RIPD |
| ATOM | 30 | HA | ILE | 590 | -18.102 | 2.067 | 0.811 | 1.00 | 4.30 | RIPD |
| ATOM | 31 | CB | ILE | 590 | -18.186 | 1.061 | -1.092 | 1.00 | 4.54 | RIPD |
| ATOM | 32 | HB | ILE | 590 | -17.268 | 0.542 | -1.336 | 1.00 | 4.90 | RIPD |
| ATOM | 33 | CG1 | ILE | 590 | -18.892 | 1.484 | -2.390 | 1.00 | 4.84 | RIPD |
| ATOM | 34 | HG11 | ILE | 590 | -18.244 | 2.135 | -2.956 | 1.00 | 4.95 | RIPD |

FIG. 6A-1

| ATOM | 35 | HG12 | ILE | 590 | -19.806 | 2.006  | -2.147 | 1.00 | 4.87 | RIPD |
|------|----|------|-----|-----|---------|--------|--------|------|------|------|
| ATOM | 36 | CG2  | ILE | 590 | -19.096 | 0.117  | -0.306 | 1.00 | 5.03 | RIPD |
| ATOM | 37 | HG21 | ILE | 590 | -18.618 | -0.151 | 0.625  | 1.00 | 5.36 | RIPD |
| ATOM | 38 | HG22 | ILE | 590 | -19.276 | -0.775 | -0.887 | 1.00 | 5.21 | RIPD |
| ATOM | 39 | HG23 | ILE | 590 | -20.035 | 0.610  | -0.101 | 1.00 | 5.29 | RIPD |
| ATOM | 40 | CD1  | ILE | 590 | -19.218 | 0.244  | -3.225 | 1.00 | 5.63 | RIPD |
| ATOM | 41 | HD11 | ILE | 590 | -18.348 | -0.393 | -3.282 | 1.00 | 5.97 | RIPD |
| ATOM | 42 | HD12 | ILE | 590 | -19.508 | 0.547  | -4.221 | 1.00 | 5.95 | RIPD |
| ATOM | 43 | HD13 | ILE | 590 | -20.031 | -0.298 | -2.764 | 1.00 | 5.91 | RIPD |
| ATOM | 44 | C    | ILE | 590 | -16.350 | 2.569  | -0.310 | 1.00 | 3.71 | RIPD |
| ATOM | 45 | O    | ILE | 590 | -15.858 | 3.045  | -1.314 | 1.00 | 4.20 | RIPD |
| ATOM | 46 | N    | ARG | 591 | -15.618 | 2.275  | 0.729  | 1.00 | 3.32 | RIPD |
| ATOM | 47 | HN   | ARG | 591 | -16.033 | 1.889  | 1.528  | 1.00 | 3.36 | RIPD |
| ATOM | 48 | CA   | ARG | 591 | -14.150 | 2.521  | 0.699  | 1.00 | 3.43 | RIPD |
| ATOM | 49 | HA   | ARG | 591 | -13.954 | 3.471  | 0.230  | 1.00 | 4.02 | RIPD |
| ATOM | 50 | CB   | ARG | 591 | -13.603 | 2.533  | 2.128  | 1.00 | 4.25 | RIPD |
| ATOM | 51 | HB1  | ARG | 591 | -12.664 | 2.002  | 2.160  | 1.00 | 4.48 | RIPD |
| ATOM | 52 | HB2  | ARG | 591 | -14.312 | 2.052  | 2.787  | 1.00 | 4.67 | RIPD |
| ATOM | 53 | CG   | ARG | 591 | -13.385 | 3.980  | 2.579  | 1.00 | 4.87 | RIPD |
| ATOM | 54 | HG1  | ARG | 591 | -13.102 | 3.993  | 3.621  | 1.00 | 5.00 | RIPD |
| ATOM | 55 | HG2  | ARG | 591 | -14.300 | 4.539  | 2.447  | 1.00 | 4.94 | RIPD |
| ATOM | 56 | CD   | ARG | 591 | -12.272 | 4.617  | 1.743  | 1.00 | 5.87 | RIPD |
| ATOM | 57 | HD1  | ARG | 591 | -11.971 | 3.935  | 0.962  | 1.00 | 6.22 | RIPD |
| ATOM | 58 | HD2  | ARG | 591 | -11.425 | 4.834  | 2.377  | 1.00 | 6.12 | RIPD |
| ATOM | 59 | NE   | ARG | 591 | -12.770 | 5.882  | 1.132  | 1.00 | 6.49 | RIPD |
| ATOM | 60 | HE   | ARG | 591 | -12.558 | 6.744  | 1.547  | 1.00 | 6.52 | RIPD |
| ATOM | 61 | CZ   | ARG | 591 | -13.488 | 5.840  | 0.043  | 1.00 | 7.30 | RIPD |
| ATOM | 62 | NH1  | ARG | 591 | -14.763 | 6.113  | 0.090  | 1.00 | 7.87 | RIPD |
| ATOM | 63 | HH11 | ARG | 591 | -15.192 | 6.356  | 0.960  | 1.00 | 7.74 | RIPD |
| ATOM | 64 | HH12 | ARG | 591 | -15.312 | 6.077  | -0.745 | 1.00 | 8.59 | RIPD |
| ATOM | 65 | NH2  | ARG | 591 | -12.931 | 5.521  | -1.093 | 1.00 | 7.76 | RIPD |
| ATOM | 66 | HH21 | ARG | 591 | -11.954 | 5.310  | -1.130 | 1.00 | 7.51 | RIPD |
| ATOM | 67 | HH22 | ARG | 591 | -13.481 | 5.487  | -1.928 | 1.00 | 8.49 | RIPD |
| ATOM | 68 | C    | ARG | 591 | -13.470 | 1.410  | -0.100 | 1.00 | 2.57 | RIPD |
| ATOM | 69 | O    | ARG | 591 | -13.630 | 0.240  | 0.184  | 1.00 | 2.66 | RIPD |
| ATOM | 70 | N    | GLU | 592 | -12.712 | 1.764  | -1.101 | 1.00 | 2.44 | RIPD |

FIG. 6A-2

| ATOM | 71 | HN | GLU | 592 | -12.597 | 2.713 | -1.316 | 1.00 | 3.03 | RIPD |
|------|----|----|----|----|----|----|----|----|----|----|
| ATOM | 72 | CA | GLU | 592 | -12.025 | 0.726 | -1.918 | 1.00 | 2.14 | RIPD |
| ATOM | 73 | HA | GLU | 592 | -12.568 | -0.204 | -1.848 | 1.00 | 2.43 | RIPD |
| ATOM | 74 | CB | GLU | 592 | -11.975 | 1.179 | -3.378 | 1.00 | 3.08 | RIPD |
| ATOM | 75 | HB1 | GLU | 592 | -11.618 | 0.368 | -3.995 | 1.00 | 3.33 | RIPD |
| ATOM | 76 | HB2 | GLU | 592 | -11.308 | 2.024 | -3.470 | 1.00 | 3.60 | RIPD |
| ATOM | 77 | CG | GLU | 592 | -13.378 | 1.585 | -3.835 | 1.00 | 3.83 | RIPD |
| ATOM | 78 | HG1 | GLU | 592 | -14.093 | 1.349 | -3.062 | 1.00 | 3.99 | RIPD |
| ATOM | 79 | HG2 | GLU | 592 | -13.633 | 1.048 | -4.738 | 1.00 | 3.87 | RIPD |
| ATOM | 80 | CD | GLU | 592 | -13.406 | 3.089 | -4.110 | 1.00 | 5.01 | RIPD |
| ATOM | 81 | OE1 | GLU | 592 | -13.452 | 3.459 | -5.272 | 1.00 | 5.51 | RIPD |
| ATOM | 82 | OE2 | GLU | 592 | -13.378 | 3.846 | -3.154 | 1.00 | 5.69 | RIPD |
| ATOM | 83 | C | GLU | 592 | -10.602 | 0.526 | -1.394 | 1.00 | 1.65 | RIPD |
| ATOM | 84 | O | GLU | 592 | -9.697 | 0.193 | -2.134 | 1.00 | 2.23 | RIPD |
| ATOM | 85 | N | ASN | 593 | -10.397 | 0.725 | -0.121 | 1.00 | 1.51 | RIPD |
| ATOM | 86 | HN | ASN | 593 | -11.140 | 0.992 | 0.458 | 1.00 | 1.91 | RIPD |
| ATOM | 87 | CA | ASN | 593 | -9.035 | 0.547 | 0.454 | 1.00 | 1.86 | RIPD |
| ATOM | 88 | HA | ASN | 593 | -8.366 | 1.278 | 0.026 | 1.00 | 2.39 | RIPD |
| ATOM | 89 | CB | ASN | 593 | -9.095 | 0.735 | 1.972 | 1.00 | 2.90 | RIPD |
| ATOM | 90 | HB1 | ASN | 593 | -8.121 | 0.543 | 2.397 | 1.00 | 3.42 | RIPD |
| ATOM | 91 | HB2 | ASN | 593 | -9.814 | 0.047 | 2.391 | 1.00 | 3.25 | RIPD |
| ATOM | 92 | CG | ASN | 593 | -9.515 | 2.171 | 2.292 | 1.00 | 3.56 | RIPD |
| ATOM | 93 | OD1 | ASN | 593 | -9.051 | 3.106 | 1.669 | 1.00 | 3.75 | RIPD |
| ATOM | 94 | ND2 | ASN | 593 | -10.379 | 2.389 | 3.246 | 1.00 | 4.42 | RIPD |
| ATOM | 95 | HD21 | ASN | 593 | -10.752 | 1.636 | 3.750 | 1.00 | 4.64 | RIPD |
| ATOM | 96 | HD22 | ASN | 593 | -10.656 | 3.305 | 3.458 | 1.00 | 5.04 | RIPD |
| ATOM | 97 | C | ASN | 593 | -8.524 | -0.859 | 0.133 | 1.00 | 1.28 | RIPD |
| ATOM | 98 | O | ASN | 593 | -9.191 | -1.640 | -0.517 | 1.00 | 1.47 | RIPD |
| ATOM | 99 | N | LEU | 594 | -7.344 | -1.188 | 0.584 | 1.00 | 0.91 | RIPD |
| ATOM | 100 | HN | LEU | 594 | -6.823 | -0.543 | 1.106 | 1.00 | 1.06 | RIPD |
| ATOM | 101 | CA | LEU | 594 | -6.794 | -2.547 | 0.301 | 1.00 | 0.89 | RIPD |
| ATOM | 102 | HA | LEU | 594 | -6.876 | -2.752 | -0.755 | 1.00 | 1.16 | RIPD |
| ATOM | 103 | CB | LEU | 594 | -5.319 | -2.618 | 0.722 | 1.00 | 1.25 | RIPD |
| ATOM | 104 | HB1 | LEU | 594 | -4.998 | -3.649 | 0.716 | 1.00 | 1.78 | RIPD |
| ATOM | 105 | HB2 | LEU | 594 | -5.215 | -2.219 | 1.718 | 1.00 | 1.56 | RIPD |
| ATOM | 106 | CG | LEU | 594 | -4.441 | -1.809 | -0.244 | 1.00 | 1.09 | RIPD |

FIG. 6A-3

| ATOM | 107 | HG   | LEU | 594 | -3.401  | -1.980 | -0.008 | 1.00 | 1.74 | RIPD |
|------|-----|------|-----|-----|---------|--------|--------|------|------|------|
| ATOM | 108 | CD1  | LEU | 594 | -4.707  | -2.236 | -1.687 | 1.00 | 1.67 | RIPD |
| ATOM | 109 | HD11 | LEU | 594 | -3.878  | -1.935 | -2.309 | 1.00 | 1.97 | RIPD |
| ATOM | 110 | HD12 | LEU | 594 | -5.612  | -1.762 | -2.038 | 1.00 | 2.15 | RIPD |
| ATOM | 111 | HD13 | LEU | 594 | -4.822  | -3.308 | -1.729 | 1.00 | 2.34 | RIPD |
| ATOM | 112 | CD2  | LEU | 594 | -4.751  | -0.325 | -0.093 | 1.00 | 0.95 | RIPD |
| ATOM | 113 | HD21 | LEU | 594 | -4.804  | -0.085 | 0.955  | 1.00 | 1.47 | RIPD |
| ATOM | 114 | HD22 | LEU | 594 | -5.698  | -0.103 | -0.564 | 1.00 | 1.52 | RIPD |
| ATOM | 115 | HD23 | LEU | 594 | -3.970  | 0.258  | -0.559 | 1.00 | 1.53 | RIPD |
| ATOM | 116 | C    | LEU | 594 | -7.590  | -3.598 | 1.083  | 1.00 | 0.95 | RIPD |
| ATOM | 117 | O    | LEU | 594 | -7.514  | -4.777 | 0.803  | 1.00 | 1.35 | RIPD |
| ATOM | 118 | N    | GLY | 595 | -8.352  | -3.188 | 2.062  | 1.00 | 0.95 | RIPD |
| ATOM | 119 | HN   | GLY | 595 | -8.404  | -2.234 | 2.281  | 1.00 | 1.16 | RIPD |
| ATOM | 120 | CA   | GLY | 595 | -9.144  | -4.176 | 2.847  | 1.00 | 1.09 | RIPD |
| ATOM | 121 | HA1  | GLY | 595 | -8.697  | -5.153 | 2.749  | 1.00 | 1.26 | RIPD |
| ATOM | 122 | HA2  | GLY | 595 | -10.157 | -4.204 | 2.473  | 1.00 | 1.37 | RIPD |
| ATOM | 123 | C    | GLY | 595 | -9.154  | -3.772 | 4.322  | 1.00 | 0.89 | RIPD |
| ATOM | 124 | O    | GLY | 595 | -8.582  | -2.772 | 4.707  | 1.00 | 0.81 | RIPD |
| ATOM | 125 | N    | LYS | 596 | -9.802  | -4.543 | 5.152  | 1.00 | 0.95 | RIPD |
| ATOM | 126 | HN   | LYS | 596 | -10.257 | -5.345 | 4.821  | 1.00 | 1.08 | RIPD |
| ATOM | 127 | CA   | LYS | 596 | -9.851  | -4.204 | 6.603  | 1.00 | 0.96 | RIPD |
| ATOM | 128 | HA   | LYS | 596 | -9.974  | -3.137 | 6.718  | 1.00 | 1.10 | RIPD |
| ATOM | 129 | CB   | LYS | 596 | -11.033 | -4.924 | 7.255  | 1.00 | 1.12 | RIPD |
| ATOM | 130 | HB1  | LYS | 596 | -10.881 | -4.972 | 8.322  | 1.00 | 1.46 | RIPD |
| ATOM | 131 | HB2  | LYS | 596 | -11.110 | -5.926 | 6.856  | 1.00 | 1.56 | RIPD |
| ATOM | 132 | CG   | LYS | 596 | -12.323 | -4.155 | 6.960  | 1.00 | 1.50 | RIPD |
| ATOM | 133 | HG1  | LYS | 596 | -12.526 | -4.187 | 5.900  | 1.00 | 1.93 | RIPD |
| ATOM | 134 | HG2  | LYS | 596 | -12.208 | -3.128 | 7.275  | 1.00 | 1.95 | RIPD |
| ATOM | 135 | CD   | LYS | 596 | -13.486 | -4.796 | 7.719  | 1.00 | 1.97 | RIPD |
| ATOM | 136 | HD1  | LYS | 596 | -13.409 | -4.552 | 8.768  | 1.00 | 2.28 | RIPD |
| ATOM | 137 | HD2  | LYS | 596 | -13.449 | -5.869 | 7.595  | 1.00 | 2.22 | RIPD |
| ATOM | 138 | CE   | LYS | 596 | -14.811 | -4.264 | 7.170  | 1.00 | 2.76 | RIPD |
| ATOM | 139 | HE1  | LYS | 596 | -15.068 | -4.799 | 6.268  | 1.00 | 3.04 | RIPD |
| ATOM | 140 | HE2  | LYS | 596 | -14.711 | -3.211 | 6.947  | 1.00 | 3.15 | RIPD |
| ATOM | 141 | NZ   | LYS | 596 | -15.883 | -4.458 | 8.187  | 1.00 | 3.51 | RIPD |
| ATOM | 142 | HZ1  | LYS | 596 | -16.788 | -4.118 | 7.806  | 1.00 | 3.80 | RIPD |

FIG. 6A-4

| | | | | | | | | | | |
|---|---|---|---|---|---|---|---|---|---|---|
| ATOM | 143 | HZ2 | LYS | 596 | -15.645 | -3.924 | 9.047 | 1.00 | 3.88 | RIPD |
| ATOM | 144 | HZ3 | LYS | 596 | -15.964 | -5.468 | 8.416 | 1.00 | 3.85 | RIPD |
| ATOM | 145 | C | LYS | 596 | -8.549 | -4.642 | 7.278 | 1.00 | 0.88 | RIPD |
| ATOM | 146 | O | LYS | 596 | -7.991 | -3.929 | 8.088 | 1.00 | 0.87 | RIPD |
| ATOM | 147 | N | HIS | 597 | -8.061 | -5.809 | 6.954 | 1.00 | 0.85 | RIPD |
| ATOM | 148 | HN | HIS | 597 | -8.526 | -6.371 | 6.299 | 1.00 | 0.88 | RIPD |
| ATOM | 149 | CA | HIS | 597 | -6.795 | -6.288 | 7.582 | 1.00 | 0.82 | RIPD |
| ATOM | 150 | HA | HIS | 597 | -6.954 | -6.441 | 8.639 | 1.00 | 0.87 | RIPD |
| ATOM | 151 | CB | HIS | 597 | -6.371 | -7.609 | 6.935 | 1.00 | 0.85 | RIPD |
| ATOM | 152 | HB1 | HIS | 597 | -5.297 | -7.707 | 6.990 | 1.00 | 1.21 | RIPD |
| ATOM | 153 | HB2 | HIS | 597 | -6.680 | -7.618 | 5.900 | 1.00 | 1.16 | RIPD |
| ATOM | 154 | CG | HIS | 597 | -7.017 | -8.756 | 7.662 | 1.00 | 1.33 | RIPD |
| ATOM | 155 | ND1 | HIS | 597 | -6.964 | -8.880 | 9.042 | 1.00 | 2.23 | RIPD |
| ATOM | 156 | HD1 | HIS | 597 | -6.525 | -8.261 | 9.662 | 1.00 | 2.74 | RIPD |
| ATOM | 157 | CD2 | HIS | 597 | -7.728 | -9.842 | 7.216 | 1.00 | 2.02 | RIPD |
| ATOM | 158 | HD2 | HIS | 597 | -7.956 | -10.055 | 6.182 | 1.00 | 2.51 | RIPD |
| ATOM | 159 | CE1 | HIS | 597 | -7.625 | -10.004 | 9.374 | 1.00 | 2.81 | RIPD |
| ATOM | 160 | HE1 | HIS | 597 | -7.747 | -10.358 | 10.387 | 1.00 | 3.63 | RIPD |
| ATOM | 161 | NE2 | HIS | 597 | -8.112 | -10.629 | 8.298 | 1.00 | 2.72 | RIPD |
| ATOM | 162 | C | HIS | 597 | -5.695 | -5.243 | 7.379 | 1.00 | 0.73 | RIPD |
| ATOM | 163 | O | HIS | 597 | -5.111 | -4.752 | 8.324 | 1.00 | 0.71 | RIPD |
| ATOM | 164 | N | TRP | 598 | -5.408 | -4.898 | 6.152 | 1.00 | 0.69 | RIPD |
| ATOM | 165 | HN | TRP | 598 | -5.891 | -5.305 | 5.403 | 1.00 | 0.73 | RIPD |
| ATOM | 166 | CA | TRP | 598 | -4.346 | -3.883 | 5.891 | 1.00 | 0.62 | RIPD |
| ATOM | 167 | HA | TRP | 598 | -3.412 | -4.224 | 6.313 | 1.00 | 0.60 | RIPD |
| ATOM | 168 | CB | TRP | 598 | -4.185 | -3.695 | 4.378 | 1.00 | 0.60 | RIPD |
| ATOM | 169 | HB1 | TRP | 598 | -5.140 | -3.434 | 3.946 | 1.00 | 0.66 | RIPD |
| ATOM | 170 | HB2 | TRP | 598 | -3.835 | -4.617 | 3.938 | 1.00 | 0.62 | RIPD |
| ATOM | 171 | CG | TRP | 598 | -3.197 | -2.604 | 4.095 | 1.00 | 0.54 | RIPD |
| ATOM | 172 | CD1 | TRP | 598 | -3.488 | -1.436 | 3.478 | 1.00 | 0.59 | RIPD |
| ATOM | 173 | HD1 | TRP | 598 | -4.461 | -1.143 | 3.117 | 1.00 | 0.70 | RIPD |
| ATOM | 174 | CD2 | TRP | 598 | -1.773 | -2.558 | 4.405 | 1.00 | 0.50 | RIPD |
| ATOM | 175 | NE1 | TRP | 598 | -2.335 | -0.678 | 3.385 | 1.00 | 0.55 | RIPD |
| ATOM | 176 | HE1 | TRP | 598 | -2.274 | 0.211 | 2.978 | 1.00 | 0.61 | RIPD |
| ATOM | 177 | CE2 | TRP | 598 | -1.251 | -1.326 | 3.942 | 1.00 | 0.49 | RIPD |
| ATOM | 178 | CE3 | TRP | 598 | -0.891 | -3.455 | 5.034 | 1.00 | 0.58 | RIPD |

FIG. 6A-5

| ATOM | 179 | HE3 | TRP | 598 | -1.259 | -4.403 | 5.398 | 1.00 | 0.65 | RIPD |
|------|-----|-----|-----|-----|--------|--------|-------|------|------|------|
| ATOM | 180 | CZ2 | TRP | 598 | 0.095 | -0.996 | 4.097 | 1.00 | 0.51 | RIPD |
| ATOM | 181 | HZ2 | TRP | 598 | 0.468 | -0.049 | 3.735 | 1.00 | 0.53 | RIPD |
| ATOM | 182 | CZ3 | TRP | 598 | 0.466 | -3.126 | 5.192 | 1.00 | 0.65 | RIPD |
| ATOM | 183 | HZ3 | TRP | 598 | 1.134 | -3.822 | 5.677 | 1.00 | 0.79 | RIPD |
| ATOM | 184 | CH2 | TRP | 598 | 0.957 | -1.898 | 4.724 | 1.00 | 0.60 | RIPD |
| ATOM | 185 | HH2 | TRP | 598 | 2.001 | -1.650 | 4.847 | 1.00 | 0.68 | RIPD |
| ATOM | 186 | C | TRP | 598 | -4.744 | -2.555 | 6.540 | 1.00 | 0.62 | RIPD |
| ATOM | 187 | O | TRP | 598 | -3.907 | -1.733 | 6.855 | 1.00 | 0.60 | RIPD |
| ATOM | 188 | N | LYS | 599 | -6.015 | -2.336 | 6.742 | 1.00 | 0.71 | RIPD |
| ATOM | 189 | HN | LYS | 599 | -6.676 | -3.010 | 6.481 | 1.00 | 0.76 | RIPD |
| ATOM | 190 | CA | LYS | 599 | -6.455 | -1.060 | 7.370 | 1.00 | 0.77 | RIPD |
| ATOM | 191 | HA | LYS | 599 | -6.090 | -0.228 | 6.787 | 1.00 | 0.76 | RIPD |
| ATOM | 192 | CB | LYS | 599 | -7.983 | -1.014 | 7.426 | 1.00 | 0.91 | RIPD |
| ATOM | 193 | HB1 | LYS | 599 | -8.339 | -1.720 | 8.160 | 1.00 | 1.18 | RIPD |
| ATOM | 194 | HB2 | LYS | 599 | -8.387 | -1.268 | 6.456 | 1.00 | 1.35 | RIPD |
| ATOM | 195 | CG | LYS | 599 | -8.434 | 0.395 | 7.816 | 1.00 | 1.08 | RIPD |
| ATOM | 196 | HG1 | LYS | 599 | -8.067 | 1.104 | 7.089 | 1.00 | 1.45 | RIPD |
| ATOM | 197 | HG2 | LYS | 599 | -8.039 | 0.641 | 8.791 | 1.00 | 1.45 | RIPD |
| ATOM | 198 | CD | LYS | 599 | -9.962 | 0.454 | 7.854 | 1.00 | 1.23 | RIPD |
| ATOM | 199 | HD1 | LYS | 599 | -10.345 | -0.424 | 8.350 | 1.00 | 1.63 | RIPD |
| ATOM | 200 | HD2 | LYS | 599 | -10.346 | 0.494 | 6.844 | 1.00 | 1.48 | RIPD |
| ATOM | 201 | CE | LYS | 599 | -10.404 | 1.703 | 8.619 | 1.00 | 1.94 | RIPD |
| ATOM | 202 | HE1 | LYS | 599 | -10.055 | 2.584 | 8.102 | 1.00 | 2.45 | RIPD |
| ATOM | 203 | HE2 | LYS | 599 | -9.985 | 1.681 | 9.615 | 1.00 | 2.49 | RIPD |
| ATOM | 204 | NZ | LYS | 599 | -11.891 | 1.735 | 8.708 | 1.00 | 1.89 | RIPD |
| ATOM | 205 | HZ1 | LYS | 599 | -12.297 | 1.679 | 7.753 | 1.00 | 2.19 | RIPD |
| ATOM | 206 | HZ2 | LYS | 599 | -12.192 | 2.622 | 9.162 | 1.00 | 2.07 | RIPD |
| ATOM | 207 | HZ3 | LYS | 599 | -12.223 | 0.927 | 9.271 | 1.00 | 2.05 | RIPD |
| ATOM | 208 | C | LYS | 599 | -5.889 | -0.975 | 8.788 | 1.00 | 0.75 | RIPD |
| ATOM | 209 | O | LYS | 599 | -5.435 | 0.064 | 9.224 | 1.00 | 0.76 | RIPD |
| ATOM | 210 | N | ASN | 600 | -5.908 | -2.062 | 9.509 | 1.00 | 0.77 | RIPD |
| ATOM | 211 | HN | ASN | 600 | -6.276 | -2.891 | 9.137 | 1.00 | 0.78 | RIPD |
| ATOM | 212 | CA | ASN | 600 | -5.366 | -2.045 | 10.896 | 1.00 | 0.80 | RIPD |
| ATOM | 213 | HA | ASN | 600 | -5.820 | -1.237 | 11.450 | 1.00 | 0.86 | RIPD |
| ATOM | 214 | CB | ASN | 600 | -5.680 | -3.376 | 11.582 | 1.00 | 0.87 | RIPD |

FIG. 6A-6

| ATOM | 215 | HB1  | ASN | 600 | -5.001 | -4.135 | 11.224 | 1.00 | 1.01 | RIPD |
|------|-----|------|-----|-----|--------|--------|--------|------|------|------|
| ATOM | 216 | HB2  | ASN | 600 | -6.696 | -3.665 | 11.358 | 1.00 | 1.09 | RIPD |
| ATOM | 217 | CG   | ASN | 600 | -5.514 | -3.220 | 13.095 | 1.00 | 1.21 | RIPD |
| ATOM | 218 | OD1  | ASN | 600 | -5.248 | -2.139 | 13.580 | 1.00 | 1.74 | RIPD |
| ATOM | 219 | ND2  | ASN | 600 | -5.662 | -4.263 | 13.865 | 1.00 | 1.59 | RIPD |
| ATOM | 220 | HD21 | ASN | 600 | -5.877 | -5.135 | 13.474 | 1.00 | 1.81 | RIPD |
| ATOM | 221 | HD22 | ASN | 600 | -5.557 | -4.174 | 14.836 | 1.00 | 1.97 | RIPD |
| ATOM | 222 | C    | ASN | 600 | -3.851 | -1.841 | 10.843 | 1.00 | 0.73 | RIPD |
| ATOM | 223 | O    | ASN | 600 | -3.283 | -1.123 | 11.641 | 1.00 | 0.75 | RIPD |
| ATOM | 224 | N    | CYS | 601 | -3.194 | -2.466 | 9.904  | 1.00 | 0.67 | RIPD |
| ATOM | 225 | HN   | CYS | 601 | -3.673 | -3.038 | 9.268  | 1.00 | 0.67 | RIPD |
| ATOM | 226 | CA   | CYS | 601 | -1.717 | -2.306 | 9.795  | 1.00 | 0.63 | RIPD |
| ATOM | 227 | HA   | CYS | 601 | -1.271 | -2.401 | 10.774 | 1.00 | 0.67 | RIPD |
| ATOM | 228 | CB   | CYS | 601 | -1.154 | -3.387 | 8.870  | 1.00 | 0.62 | RIPD |
| ATOM | 229 | HB1  | CYS | 601 | -0.324 | -2.983 | 8.308  | 1.00 | 0.76 | RIPD |
| ATOM | 230 | HB2  | CYS | 601 | -1.924 | -3.715 | 8.188  | 1.00 | 0.83 | RIPD |
| ATOM | 231 | SG   | CYS | 601 | -0.586 | -4.792 | 9.859  | 1.00 | 1.24 | RIPD |
| ATOM | 232 | HG   | CYS | 601 | -1.349 | -5.169 | 10.304 | 1.00 | 1.58 | RIPD |
| ATOM | 233 | C    | CYS | 601 | -1.399 | -0.925 | 9.220  | 1.00 | 0.57 | RIPD |
| ATOM | 234 | O    | CYS | 601 | -0.558 | -0.210 | 9.726  | 1.00 | 0.56 | RIPD |
| ATOM | 235 | N    | ALA | 602 | -2.069 | -0.542 | 8.166  | 1.00 | 0.55 | RIPD |
| ATOM | 236 | HN   | ALA | 602 | -2.746 | -1.133 | 7.774  | 1.00 | 0.58 | RIPD |
| ATOM | 237 | CA   | ALA | 602 | -1.807 | 0.795  | 7.564  | 1.00 | 0.53 | RIPD |
| ATOM | 238 | HA   | ALA | 602 | -0.792 | 0.834  | 7.198  | 1.00 | 0.51 | RIPD |
| ATOM | 239 | CB   | ALA | 602 | -2.779 | 1.034  | 6.406  | 1.00 | 0.56 | RIPD |
| ATOM | 240 | HB1  | ALA | 602 | -3.792 | 1.023  | 6.778  | 1.00 | 1.23 | RIPD |
| ATOM | 241 | HB2  | ALA | 602 | -2.657 | 0.255  | 5.668  | 1.00 | 1.12 | RIPD |
| ATOM | 242 | HB3  | ALA | 602 | -2.572 | 1.993  | 5.955  | 1.00 | 1.05 | RIPD |
| ATOM | 243 | C    | ALA | 602 | -2.007 | 1.873  | 8.630  | 1.00 | 0.54 | RIPD |
| ATOM | 244 | O    | ALA | 602 | -1.130 | 2.673  | 8.890  | 1.00 | 0.53 | RIPD |
| ATOM | 245 | N    | ARG | 603 | -3.154 | 1.897  | 9.255  | 1.00 | 0.58 | RIPD |
| ATOM | 246 | HN   | ARG | 603 | -3.846 | 1.240  | 9.034  | 1.00 | 0.60 | RIPD |
| ATOM | 247 | CA   | ARG | 603 | -3.405 | 2.920  | 10.309 | 1.00 | 0.62 | RIPD |
| ATOM | 248 | HA   | ARG | 603 | -3.393 | 3.905  | 9.867  | 1.00 | 0.63 | RIPD |
| ATOM | 249 | CB   | ARG | 603 | -4.768 | 2.664  | 10.956 | 1.00 | 0.67 | RIPD |
| ATOM | 250 | HB1  | ARG | 603 | -4.889 | 3.313  | 11.809 | 1.00 | 0.71 | RIPD |

FIG. 6A-7

| ATOM | 251 | HB2  | ARG | 603 | -4.827 | 1.633  | 11.275 | 1.00 | 0.68 | RIPD |
|------|-----|------|-----|-----|--------|--------|--------|------|------|------|
| ATOM | 252 | CG   | ARG | 603 | -5.878 | 2.948  | 9.942  | 1.00 | 0.71 | RIPD |
| ATOM | 253 | HG1  | ARG | 603 | -5.765 | 2.294  | 9.090  | 1.00 | 0.97 | RIPD |
| ATOM | 254 | HG2  | ARG | 603 | -5.815 | 3.977  | 9.617  | 1.00 | 1.03 | RIPD |
| ATOM | 255 | CD   | ARG | 603 | -7.240 | 2.700  | 10.594 | 1.00 | 1.07 | RIPD |
| ATOM | 256 | HD1  | ARG | 603 | -7.285 | 1.684  | 10.958 | 1.00 | 1.68 | RIPD |
| ATOM | 257 | HD2  | ARG | 603 | -8.022 | 2.856  | 9.865  | 1.00 | 1.61 | RIPD |
| ATOM | 258 | NE   | ARG | 603 | -7.426 | 3.645  | 11.731 | 1.00 | 1.53 | RIPD |
| ATOM | 259 | HE   | ARG | 603 | -6.758 | 4.341  | 11.903 | 1.00 | 1.95 | RIPD |
| ATOM | 260 | CZ   | ARG | 603 | -8.477 | 3.544  | 12.497 | 1.00 | 2.13 | RIPD |
| ATOM | 261 | NH1  | ARG | 603 | -9.146 | 4.613  | 12.831 | 1.00 | 2.45 | RIPD |
| ATOM | 262 | HH11 | ARG | 603 | -8.854 | 5.510  | 12.499 | 1.00 | 2.54 | RIPD |
| ATOM | 263 | HH12 | ARG | 603 | -9.952 | 4.535  | 13.418 | 1.00 | 2.98 | RIPD |
| ATOM | 264 | NH2  | ARG | 603 | -8.858 | 2.374  | 12.930 | 1.00 | 2.96 | RIPD |
| ATOM | 265 | HH21 | ARG | 603 | -8.346 | 1.554  | 12.675 | 1.00 | 3.27 | RIPD |
| ATOM | 266 | HH22 | ARG | 603 | -9.664 | 2.296  | 13.517 | 1.00 | 3.53 | RIPD |
| ATOM | 267 | C    | ARG | 603 | -2.310 | 2.822  | 11.372 | 1.00 | 0.60 | RIPD |
| ATOM | 268 | O    | ARG | 603 | -1.970 | 3.792  | 12.020 | 1.00 | 0.62 | RIPD |
| ATOM | 269 | N    | LYS | 604 | -1.752 | 1.656  | 11.551 | 1.00 | 0.59 | RIPD |
| ATOM | 270 | HN   | LYS | 604 | -2.040 | 0.888  | 11.014 | 1.00 | 0.59 | RIPD |
| ATOM | 271 | CA   | LYS | 604 | -0.675 | 1.491  | 12.566 | 1.00 | 0.60 | RIPD |
| ATOM | 272 | HA   | LYS | 604 | -0.984 | 1.942  | 13.497 | 1.00 | 0.63 | RIPD |
| ATOM | 273 | CB   | LYS | 604 | -0.404 | 0.000  | 12.783 | 1.00 | 0.62 | RIPD |
| ATOM | 274 | HB1  | LYS | 604 | 0.455  | -0.298 | 12.200 | 1.00 | 1.06 | RIPD |
| ATOM | 275 | HB2  | LYS | 604 | -1.267 | -0.571 | 12.472 | 1.00 | 0.95 | RIPD |
| ATOM | 276 | CG   | LYS | 604 | -0.126 | -0.259 | 14.264 | 1.00 | 1.23 | RIPD |
| ATOM | 277 | HG1  | LYS | 604 | -0.995 | 0.008  | 14.846 | 1.00 | 1.72 | RIPD |
| ATOM | 278 | HG2  | LYS | 604 | 0.718  | 0.336  | 14.582 | 1.00 | 1.77 | RIPD |
| ATOM | 279 | CD   | LYS | 604 | 0.187  | -1.742 | 14.473 | 1.00 | 1.29 | RIPD |
| ATOM | 280 | HD1  | LYS | 604 | 0.990  | -2.037 | 13.814 | 1.00 | 1.54 | RIPD |
| ATOM | 281 | HD2  | LYS | 604 | -0.693 | -2.330 | 14.255 | 1.00 | 1.35 | RIPD |
| ATOM | 282 | CE   | LYS | 604 | 0.611  | -1.975 | 15.925 | 1.00 | 1.92 | RIPD |
| ATOM | 283 | HE1  | LYS | 604 | -0.248 | -1.870 | 16.571 | 1.00 | 2.39 | RIPD |
| ATOM | 284 | HE2  | LYS | 604 | 1.361  | -1.249 | 16.201 | 1.00 | 2.24 | RIPD |
| ATOM | 285 | NZ   | LYS | 604 | 1.174  | -3.348 | 16.064 | 1.00 | 2.28 | RIPD |
| ATOM | 286 | HZ1  | LYS | 604 | 0.522  | -4.035 | 15.636 | 1.00 | 2.52 | RIPD |

FIG. 6A-8

| ATOM | 287 | HZ2 | LYS | 604 | 1.299 | -3.569 | 17.073 | 1.00 | 2.64 | RIPD |
|---|---|---|---|---|---|---|---|---|---|---|
| ATOM | 288 | HZ3 | LYS | 604 | 2.093 | -3.397 | 15.581 | 1.00 | 2.60 | RIPD |
| ATOM | 289 | C | LYS | 604 | 0.598 | 2.173 | 12.064 | 1.00 | 0.59 | RIPD |
| ATOM | 290 | O | LYS | 604 | 1.320 | 2.796 | 12.817 | 1.00 | 0.62 | RIPD |
| ATOM | 291 | N | LEU | 605 | 0.878 | 2.062 | 10.794 | 1.00 | 0.56 | RIPD |
| ATOM | 292 | HN | LEU | 605 | 0.281 | 1.556 | 10.204 | 1.00 | 0.54 | RIPD |
| ATOM | 293 | CA | LEU | 605 | 2.101 | 2.705 | 10.241 | 1.00 | 0.57 | RIPD |
| ATOM | 294 | HA | LEU | 605 | 2.967 | 2.361 | 10.785 | 1.00 | 0.59 | RIPD |
| ATOM | 295 | CB | LEU | 605 | 2.249 | 2.333 | 8.765 | 1.00 | 0.56 | RIPD |
| ATOM | 296 | HB1 | LEU | 605 | 3.155 | 2.769 | 8.372 | 1.00 | 0.58 | RIPD |
| ATOM | 297 | HB2 | LEU | 605 | 1.400 | 2.708 | 8.213 | 1.00 | 0.55 | RIPD |
| ATOM | 298 | CG | LEU | 605 | 2.318 | 0.812 | 8.628 | 1.00 | 0.57 | RIPD |
| ATOM | 299 | HG | LEU | 605 | 1.525 | 0.362 | 9.209 | 1.00 | 0.57 | RIPD |
| ATOM | 300 | CD1 | LEU | 605 | 2.153 | 0.425 | 7.159 | 1.00 | 0.58 | RIPD |
| ATOM | 301 | HD11 | LEU | 605 | 1.255 | -0.163 | 7.040 | 1.00 | 1.16 | RIPD |
| ATOM | 302 | HD12 | LEU | 605 | 3.008 | -0.153 | 6.841 | 1.00 | 1.14 | RIPD |
| ATOM | 303 | HD13 | LEU | 605 | 2.079 | 1.319 | 6.558 | 1.00 | 1.20 | RIPD |
| ATOM | 304 | CD2 | LEU | 605 | 3.673 | 0.313 | 9.136 | 1.00 | 0.61 | RIPD |
| ATOM | 305 | HD21 | LEU | 605 | 3.973 | -0.554 | 8.567 | 1.00 | 1.09 | RIPD |
| ATOM | 306 | HD22 | LEU | 605 | 3.591 | 0.048 | 10.180 | 1.00 | 1.32 | RIPD |
| ATOM | 307 | HD23 | LEU | 605 | 4.410 | 1.094 | 9.019 | 1.00 | 1.14 | RIPD |
| ATOM | 308 | C | LEU | 605 | 1.980 | 4.224 | 10.374 | 1.00 | 0.59 | RIPD |
| ATOM | 309 | O | LEU | 605 | 2.965 | 4.932 | 10.451 | 1.00 | 0.63 | RIPD |
| ATOM | 310 | N | GLY | 606 | 0.778 | 4.732 | 10.401 | 1.00 | 0.58 | RIPD |
| ATOM | 311 | HN | GLY | 606 | -0.003 | 4.143 | 10.337 | 1.00 | 0.57 | RIPD |
| ATOM | 312 | CA | GLY | 606 | 0.592 | 6.205 | 10.529 | 1.00 | 0.62 | RIPD |
| ATOM | 313 | HA1 | GLY | 606 | 1.551 | 6.679 | 10.667 | 1.00 | 0.66 | RIPD |
| ATOM | 314 | HA2 | GLY | 606 | -0.041 | 6.414 | 11.381 | 1.00 | 0.66 | RIPD |
| ATOM | 315 | C | GLY | 606 | -0.063 | 6.749 | 9.258 | 1.00 | 0.59 | RIPD |
| ATOM | 316 | O | GLY | 606 | 0.316 | 7.784 | 8.748 | 1.00 | 0.64 | RIPD |
| ATOM | 317 | N | PHE | 607 | -1.044 | 6.060 | 8.742 | 1.00 | 0.55 | RIPD |
| ATOM | 318 | HN | PHE | 607 | -1.335 | 5.226 | 9.168 | 1.00 | 0.54 | RIPD |
| ATOM | 319 | CA | PHE | 607 | -1.720 | 6.539 | 7.503 | 1.00 | 0.55 | RIPD |
| ATOM | 320 | HA | PHE | 607 | -1.313 | 7.499 | 7.220 | 1.00 | 0.57 | RIPD |
| ATOM | 321 | CB | PHE | 607 | -1.486 | 5.534 | 6.374 | 1.00 | 0.52 | RIPD |
| ATOM | 322 | HB1 | PHE | 607 | -1.989 | 5.873 | 5.480 | 1.00 | 0.54 | RIPD |

FIG. 6A-9

| ATOM | 323 | HB2 | PHE | 607 | -1.878 | 4.569 | 6.664 | 1.00 | 0.53 | RIPD |
| ATOM | 324 | CG | PHE | 607 | -0.006 | 5.416 | 6.104 | 1.00 | 0.49 | RIPD |
| ATOM | 325 | CD1 | PHE | 607 | 0.584 | 4.153 | 5.973 | 1.00 | 0.51 | RIPD |
| ATOM | 326 | HD1 | PHE | 607 | -0.021 | 3.263 | 6.065 | 1.00 | 0.57 | RIPD |
| ATOM | 327 | CD2 | PHE | 607 | 0.778 | 6.570 | 5.985 | 1.00 | 0.50 | RIPD |
| ATOM | 328 | HD2 | PHE | 607 | 0.323 | 7.544 | 6.086 | 1.00 | 0.55 | RIPD |
| ATOM | 329 | CE1 | PHE | 607 | 1.957 | 4.044 | 5.723 | 1.00 | 0.50 | RIPD |
| ATOM | 330 | HE1 | PHE | 607 | 2.412 | 3.070 | 5.622 | 1.00 | 0.56 | RIPD |
| ATOM | 331 | CE2 | PHE | 607 | 2.151 | 6.461 | 5.735 | 1.00 | 0.49 | RIPD |
| ATOM | 332 | HE2 | PHE | 607 | 2.755 | 7.351 | 5.643 | 1.00 | 0.55 | RIPD |
| ATOM | 333 | CZ | PHE | 607 | 2.741 | 5.198 | 5.604 | 1.00 | 0.47 | RIPD |
| ATOM | 334 | HZ | PHE | 607 | 3.800 | .114 | 5.412 | 1.00 | 0.49 | RIPD |
| ATOM | 335 | C | PHE | 607 | -3.222 | 6.678 | 7.760 | 1.00 | 0.60 | RIPD |
| ATOM | 336 | O | PHE | 607 | -3.793 | 5.967 | 8.563 | 1.00 | 0.64 | RIPD |
| ATOM | 337 | N | THR | 608 | -3.866 | 7.588 | 7.082 | 1.00 | 0.64 | RIPD |
| ATOM | 338 | HN | THR | 608 | -3.387 | 8.150 | 6.439 | 1.00 | 0.65 | RIPD |
| ATOM | 339 | CA | THR | 608 | -5.331 | 7.772 | 7.286 | 1.00 | 0.71 | RIPD |
| ATOM | 340 | HA | THR | 608 | -5.583 | 7.544 | 8.311 | 1.00 | 0.75 | RIPD |
| ATOM | 341 | CB | THR | 608 | -5.710 | 9.222 | 6.976 | 1.00 | 0.79 | RIPD |
| ATOM | 342 | HB | THR | 608 | -6.653 | 9.245 | 6.453 | 1.00 | 1.37 | RIPD |
| ATOM | 343 | OG1 | THR | 608 | -4.702 | 9.809 | 6.165 | 1.00 | 1.38 | RIPD |
| ATOM | 344 | HG1 | THR | 608 | -5.098 | 10.538 | 5.681 | 1.00 | 1.79 | RIPD |
| ATOM | 345 | CG2 | THR | 608 | -5.838 | 10.008 | 8.282 | 1.00 | 1.31 | RIPD |
| ATOM | 346 | HG21 | THR | 608 | -4.882 | 10.032 | 8.784 | 1.00 | 1.85 | RIPD |
| ATOM | 347 | HG22 | THR | 608 | -6.568 | 9.530 | 8.919 | 1.00 | 1.92 | RIPD |
| ATOM | 348 | HG23 | THR | 608 | -6.156 | 11.017 | 8.065 | 1.00 | 1.77 | RIPD |
| ATOM | 349 | C | THR | 608 | -6.096 | 6.832 | 6.351 | 1.00 | 0.71 | RIPD |
| ATOM | 350 | O | THR | 608 | -5.511 | 6.094 | 5.584 | 1.00 | 0.68 | RIPD |
| ATOM | 351 | N | GLN | 609 | -7.400 | 6.853 | 6.409 | 1.00 | 0.77 | RIPD |
| ATOM | 352 | HN | GLN | 609 | -7.853 | 7.455 | 7.035 | 1.00 | 0.82 | RIPD |
| ATOM | 353 | CA | GLN | 609 | -8.198 | 5.959 | 5.523 | 1.00 | 0.80 | RIPD |
| ATOM | 354 | HA | GLN | 609 | -7.822 | 4.950 | 5.598 | 1.00 | 0.78 | RIPD |
| ATOM | 355 | CB | GLN | 609 | -9.666 | 5.989 | 5.956 | 1.00 | 0.89 | RIPD |
| ATOM | 356 | HB1 | GLN | 609 | -10.290 | 6.195 | 5.100 | 1.00 | 1.31 | RIPD |
| ATOM | 357 | HB2 | GLN | 609 | -9.806 | 6.761 | 6.700 | 1.00 | 1.29 | RIPD |
| ATOM | 358 | CG | GLN | 609 | -10.050 | 4.632 | 6.549 | 1.00 | 1.46 | RIPD |

FIG. 6A-10

| | | | | | | | | | | |
|---|---|---|---|---|---|---|---|---|---|---|
| ATOM | 359 | HG1 | GLN | 609 | -9.487 | 4.462 | 7.454 | 1.00 | 1.96 | RIPD |
| ATOM | 360 | HG2 | GLN | 609 | -9.829 | 3.852 | 5.835 | 1.00 | 1.98 | RIPD |
| ATOM | 361 | CD | GLN | 609 | -11.545 | 4.620 | 6.872 | 1.00 | 1.50 | RIPD |
| ATOM | 362 | OE1 | GLN | 609 | -12.030 | 5.472 | 7.590 | 1.00 | 1.10 | RIPD |
| ATOM | 363 | NE2 | GLN | 609 | -12.302 | 3.683 | 6.370 | 1.00 | 2.26 | RIPD |
| ATOM | 364 | HE21 | GLN | 609 | -11.910 | 2.995 | 5.791 | 1.00 | 2.88 | RIPD |
| ATOM | 365 | HE22 | GLN | 609 | -13.261 | 3.667 | 6.570 | 1.00 | 2.29 | RIPD |
| ATOM | 366 | C | GLN | 609 | -8.082 | 6.438 | 4.074 | 1.00 | 0.78 | RIPD |
| ATOM | 367 | O | GLN | 609 | -7.950 | 5.650 | 3.159 | 1.00 | 0.76 | RIPD |
| ATOM | 368 | N | SER | 610 | -8.129 | 7.724 | 3.858 | 1.00 | 0.81 | RIPD |
| ATOM | 369 | HN | SER | 610 | -8.235 | 8.344 | 4.610 | 1.00 | 0.84 | RIPD |
| ATOM | 370 | CA | SER | 610 | -8.020 | 8.250 | 2.468 | 1.00 | 0.82 | RIPD |
| ATOM | 371 | HA | SER | 610 | -8.690 | 7.701 | 1.822 | 1.00 | 0.86 | RIPD |
| ATOM | 372 | CB | SER | 610 | -8.395 | 9.732 | 2.453 | 1.00 | 0.92 | RIPD |
| ATOM | 373 | HB1 | SER | 610 | -9.246 | 9.892 | 3.102 | 1.00 | 1.46 | RIPD |
| ATOM | 374 | HB2 | SER | 610 | -8.650 | 10.030 | 1.450 | 1.00 | 1.43 | RIPD |
| ATOM | 375 | OG | SER | 610 | -7.288 | 10.501 | 2.903 | 1.00 | 1.48 | RIPD |
| ATOM | 376 | HG | SER | 610 | -7.578 | 11.411 | 2.998 | 1.00 | 1.71 | RIPD |
| ATOM | 377 | C | SER | 610 | -6.582 | 8.083 | 1.971 | 1.00 | 0.73 | RIPD |
| ATOM | 378 | O | SER | 610 | -6.343 | 7.801 | 0.813 | 1.00 | 0.70 | RIPD |
| ATOM | 379 | N | GLN | 611 | -5.621 | 8.256 | 2.838 | 1.00 | 0.70 | RIPD |
| ATOM | 380 | HN | GLN | 611 | -5.835 | 8.483 | 3.767 | 1.00 | 0.73 | RIPD |
| ATOM | 381 | CA | GLN | 611 | -4.199 | 8.108 | 2.417 | 1.00 | 0.64 | RIPD |
| ATOM | 382 | HA | GLN | 611 | -3.960 | 8.866 | 1.685 | 1.00 | 0.67 | RIPD |
| ATOM | 383 | CB | GLN | 611 | -3.288 | 8.270 | 3.635 | 1.00 | 0.65 | RIPD |
| ATOM | 384 | HB1 | GLN | 611 | -2.421 | 7.636 | 3.523 | 1.00 | 1.10 | RIPD |
| ATOM | 385 | HB2 | GLN | 611 | -3.828 | 7.990 | 4.528 | 1.00 | 0.96 | RIPD |
| ATOM | 386 | CG | GLN | 611 | -2.839 | 9.729 | 3.745 | 1.00 | 1.01 | RIPD |
| ATOM | 387 | HG1 | GLN | 611 | -3.657 | 10.330 | 4.113 | 1.00 | 1.68 | RIPD |
| ATOM | 388 | HG2 | GLN | 611 | -2.538 | 10.087 | 2.771 | 1.00 | 1.58 | RIPD |
| ATOM | 389 | CD | GLN | 611 | -1.660 | 9.828 | 4.714 | 1.00 | 1.19 | RIPD |
| ATOM | 390 | OE1 | GLN | 611 | -1.306 | 8.861 | 5.359 | 1.00 | 1.41 | RIPD |
| ATOM | 391 | NE2 | GLN | 611 | -1.032 | 10.964 | 4.845 | 1.00 | 1.92 | RIPD |
| ATOM | 392 | HE21 | GLN | 611 | -1.317 | 11.744 | 4.325 | 1.00 | 2.31 | RIPD |
| ATOM | 393 | HE22 | GLN | 611 | -0.275 | 11.037 | 5.463 | 1.00 | 2.31 | RIPD |
| ATOM | 394 | C | GLN | 611 | -3.989 | 6.723 | 1.802 | 1.00 | 0.55 | RIPD |

FIG. 6A-11

| ATOM | 395 | O    | GLN | 611 | -3.268 | 6.565 | 0.837  | 1.00 | 0.52 | RIPD |
| ---- | --- | ---- | --- | --- | ------ | ----- | ------ | ---- | ---- | ---- |
| ATOM | 396 | N    | ILE | 612 | -4.613 | 5.719 | 2.352  | 1.00 | 0.54 | RIPD |
| ATOM | 397 | HN   | ILE | 612 | -5.190 | 5.867 | 3.130  | 1.00 | 0.59 | RIPD |
| ATOM | 398 | CA   | ILE | 612 | -4.448 | 4.347 | 1.797  | 1.00 | 0.50 | RIPD |
| ATOM | 399 | HA   | ILE | 612 | -3.410 | 4.054 | 1.865  | 1.00 | 0.47 | RIPD |
| ATOM | 400 | CB   | ILE | 612 | -5.311 | 3.364 | 2.606  | 1.00 | 0.56 | RIPD |
| ATOM | 401 | HB   | ILE | 612 | -6.307 | 3.768 | 2.714  | 1.00 | 0.61 | RIPD |
| ATOM | 402 | CG1  | ILE | 612 | -4.686 | 3.162 | 3.994  | 1.00 | 0.61 | RIPD |
| ATOM | 403 | HG11 | ILE | 612 | -4.778 | 4.074 | 4.565  | 1.00 | 0.65 | RIPD |
| ATOM | 404 | HG12 | ILE | 612 | -3.641 | 2.912 | 3.884  | 1.00 | 0.58 | RIPD |
| ATOM | 405 | CG2  | ILE | 612 | -5.386 | 2.017 | 1.879  | 1.00 | 0.57 | RIPD |
| ATOM | 406 | HG21 | ILE | 612 | -4.389 | 1.621 | 1.755  | 1.00 | 1.09 | RIPD |
| ATOM | 407 | HG22 | ILE | 612 | -5.842 | 2.156 | 0.910  | 1.00 | 1.25 | RIPD |
| ATOM | 408 | HG23 | ILE | 612 | -5.979 | 1.326 | 2.461  | 1.00 | 1.11 | RIPD |
| ATOM | 409 | CD1  | ILE | 612 | -5.407 | 2.027 | 4.733  | 1.00 | 0.71 | RIPD |
| ATOM | 410 | HD11 | ILE | 612 | -6.246 | 1.690 | 4.140  | 1.00 | 1.27 | RIPD |
| ATOM | 411 | HD12 | ILE | 612 | -5.760 | 2.384 | 5.688  | 1.00 | 1.32 | RIPD |
| ATOM | 412 | HD13 | ILE | 612 | -4.723 | 1.205 | 4.884  | 1.00 | 1.18 | RIPD |
| ATOM | 413 | C    | ILE | 612 | -4.885 | 4.338 | 0.327  | 1.00 | 0.49 | RIPD |
| ATOM | 414 | O    | ILE | 612 | -4.119 | 4.008 | -0.558 | 1.00 | 0.46 | RIPD |
| ATOM | 415 | N    | ASP | 613 | -6.117 | 4.685 | 0.064  | 1.00 | 0.55 | RIPD |
| ATOM | 416 | HN   | ASP | 613 | -6.720 | 4.937 | 0.795  | 1.00 | 0.60 | RIPD |
| ATOM | 417 | CA   | ASP | 613 | -6.615 | 4.684 | -1.343 | 1.00 | 0.58 | RIPD |
| ATOM | 418 | HA   | ASP | 613 | -6.719 | 3.663 | -1.682 | 1.00 | 0.58 | RIPD |
| ATOM | 419 | CB   | ASP | 613 | -7.977 | 5.379 | -1.401 | 1.00 | 0.67 | RIPD |
| ATOM | 420 | HB1  | ASP | 613 | -8.129 | 5.792 | -2.387 | 1.00 | 1.11 | RIPD |
| ATOM | 421 | HB2  | ASP | 613 | -8.007 | 6.173 | -0.669 | 1.00 | 1.10 | RIPD |
| ATOM | 422 | CG   | ASP | 613 | -9.081 | 4.366 | -1.100 | 1.00 | 1.38 | RIPD |
| ATOM | 423 | OD1  | ASP | 613 | -9.884 | 4.639 | -0.223 | 1.00 | 2.06 | RIPD |
| ATOM | 424 | OD2  | ASP | 613 | -9.105 | 3.334 | -1.750 | 1.00 | 2.10 | RIPD |
| ATOM | 425 | C    | ASP | 613 | -5.626 | 5.426 | -2.250 | 1.00 | 0.56 | RIPD |
| ATOM | 426 | O    | ASP | 613 | -5.525 | 5.151 | -3.428 | 1.00 | 0.57 | RIPD |
| ATOM | 427 | N    | GLU | 614 | -4.895 | 6.362 | -1.707 | 1.00 | 0.56 | RIPD |
| ATOM | 428 | HN   | GLU | 614 | -4.990 | 6.568 | -0.754 | 1.00 | 0.57 | RIPD |
| ATOM | 429 | CA   | GLU | 614 | -3.913 | 7.118 | -2.538 | 1.00 | 0.57 | RIPD |
| ATOM | 430 | HA   | GLU | 614 | -4.393 | 7.455 | -3.445 | 1.00 | 0.62 | RIPD |

FIG. 6A-12

| | | | | | | | | | |
|---|---|---|---|---|---|---|---|---|---|
| ATOM | 431 | CB | GLU | 614 | -3.402 | 8.327 | -1.750 | 1.00 | 0.61 | RIPD |
| ATOM | 432 | HB1 | GLU | 614 | -2.852 | 7.986 | -0.886 | 1.00 | 1.14 | RIPD |
| ATOM | 433 | HB2 | GLU | 614 | -4.241 | 8.928 | -1.430 | 1.00 | 1.10 | RIPD |
| ATOM | 434 | CG | GLU | 614 | -2.481 | 9.166 | -2.639 | 1.00 | 1.12 | RIPD |
| ATOM | 435 | HG1 | GLU | 614 | -2.875 | 9.191 | -3.644 | 1.00 | 1.64 | RIPD |
| ATOM | 436 | HG2 | GLU | 614 | -1.494 | 8.727 | -2.650 | 1.00 | 1.80 | RIPD |
| ATOM | 437 | CD | GLU | 614 | -2.400 | 10.592 | -2.091 | 1.00 | 1.62 | RIPD |
| ATOM | 438 | OE1 | GLU | 614 | -2.116 | 10.738 | -0.913 | 1.00 | 2.14 | RIPD |
| ATOM | 439 | OE2 | GLU | 614 | -2.624 | 11.515 | -2.858 | 1.00 | 2.29 | RIPD |
| ATOM | 440 | C | GLU | 614 | -2.737 | 6.205 | -2.893 | 1.00 | 0.52 | RIPD |
| ATOM | 441 | O | GLU | 614 | -2.233 | 6.227 | -3.998 | 1.00 | 0.53 | RIPD |
| ATOM | 442 | N | ILE | 615 | -2.296 | 5.404 | -1.963 | 1.00 | 0.47 | RIPD |
| ATOM | 443 | HN | ILE | 615 | -2.717 | 5.403 | -1.078 | 1.00 | 0.47 | RIPD |
| ATOM | 444 | CA | ILE | 615 | -1.153 | 4.490 | -2.244 | 1.00 | 0.45 | RIPD |
| ATOM | 445 | HA | ILE | 615 | -0.290 | 5.070 | -2.538 | 1.00 | 0.45 | RIPD |
| ATOM | 446 | CB | ILE | 615 | -0.825 | 3.687 | -0.985 | 1.00 | 0.44 | RIPD |
| ATOM | 447 | HB | ILE | 615 | -1.691 | 3.111 | -0.691 | 1.00 | 0.46 | RIPD |
| ATOM | 448 | CG1 | ILE | 615 | -0.439 | 4.645 | 0.145 | 1.00 | 0.46 | RIPD |
| ATOM | 449 | HG11 | ILE | 615 | -1.265 | 5.309 | 0.352 | 1.00 | 0.47 | RIPD |
| ATOM | 450 | HG12 | ILE | 615 | 0.423 | 5.223 | -0.153 | 1.00 | 0.48 | RIPD |
| ATOM | 451 | CG2 | ILE | 615 | 0.342 | 2.741 | -1.271 | 1.00 | 0.47 | RIPD |
| ATOM | 452 | HG21 | ILE | 615 | 0.506 | 2.103 | -0.415 | 1.00 | 1.05 | RIPD |
| ATOM | 453 | HG22 | ILE | 615 | 1.234 | 3.318 | -1.466 | 1.00 | 1.06 | RIPD |
| ATOM | 454 | HG23 | ILE | 615 | 0.110 | 2.133 | -2.133 | 1.00 | 1.26 | RIPD |
| ATOM | 455 | CD1 | ILE | 615 | -0.107 | 3.841 | 1.403 | 1.00 | 0.48 | RIPD |
| ATOM | 456 | HD11 | ILE | 615 | -0.261 | 4.459 | 2.276 | 1.00 | 1.09 | RIPD |
| ATOM | 457 | HD12 | ILE | 615 | 0.924 | 3.523 | 1.365 | 1.00 | 1.13 | RIPD |
| ATOM | 458 | HD13 | ILE | 615 | -0.749 | 2.975 | 1.458 | 1.00 | 1.14 | RIPD |
| ATOM | 459 | C | ILE | 615 | -1.530 | 3.532 | -3.375 | 1.00 | 0.45 | RIPD |
| ATOM | 460 | O | ILE | 615 | -0.936 | 3.544 | -4.435 | 1.00 | 0.43 | RIPD |
| ATOM | 461 | N | ASP | 616 | -2.512 | 2.698 | -3.160 | 1.00 | 0.50 | RIPD |
| ATOM | 462 | HN | ASP | 616 | -2.978 | 2.701 | -2.298 | 1.00 | 0.55 | RIPD |
| ATOM | 463 | CA | ASP | 616 | -2.920 | 1.740 | -4.227 | 1.00 | 0.52 | RIPD |
| ATOM | 464 | HA | ASP | 616 | -2.111 | 1.049 | -4.416 | 1.00 | 0.51 | RIPD |
| ATOM | 465 | CB | ASP | 616 | -4.157 | 0.962 | -3.773 | 1.00 | 0.62 | RIPD |
| ATOM | 466 | HB1 | ASP | 616 | -3.897 | 0.327 | -2.939 | 1.00 | 0.70 | RIPD |

FIG. 6A-13

| ATOM | 467 | HB2 | ASP | 616 | -4.518 | 0.353 | -4.589 | 1.00 | 0.58 | RIPD |
| ATOM | 468 | CG | ASP | 616 | -5.250 | 1.941 | -3.344 | 1.00 | 0.74 | RIPD |
| ATOM | 469 | OD1 | ASP | 616 | -5.754 | 1.790 | -2.243 | 1.00 | 1.43 | RIPD |
| ATOM | 470 | OD2 | ASP | 616 | -5.566 | 2.825 | -4.123 | 1.00 | 1.20 | RIPD |
| ATOM | 471 | C | ASP | 616 | -3.242 | 2.509 | -5.510 | 1.00 | 0.52 | RIPD |
| ATOM | 472 | O | ASP | 616 | -3.198 | 1.967 | -6.597 | 1.00 | 0.53 | RIPD |
| ATOM | 473 | N | HIS | 617 | -3.564 | 3.769 | -5.396 | 1.00 | 0.56 | RIPD |
| ATOM | 474 | HN | HIS | 617 | -3.593 | 4.190 | -4.511 | 1.00 | 0.57 | RIPD |
| ATOM | 475 | CA | HIS | 617 | -3.885 | 4.566 | -6.612 | 1.00 | 0.61 | RIPD |
| ATOM | 476 | HA | HIS | 617 | -4.631 | 4.047 | -7.196 | 1.00 | 0.67 | RIPD |
| ATOM | 477 | CB | HIS | 617 | -4.424 | 5.937 | -6.199 | 1.00 | 0.68 | RIPD |
| ATOM | 478 | HB1 | HIS | 617 | -3.636 | 6.508 | -5.731 | 1.00 | 1.06 | RIPD |
| ATOM | 479 | HB2 | HIS | 617 | -5.239 | 5.808 | -5.502 | 1.00 | 1.06 | RIPD |
| ATOM | 480 | CG | HIS | 617 | -4.916 | 6.668 | -7.417 | 1.00 | 0.89 | RIPD |
| ATOM | 481 | ND1 | HIS | 617 | -5.661 | 6.042 | -8.404 | 1.00 | 1.64 | RIPD |
| ATOM | 482 | HD1 | HIS | 617 | -5.935 | 5.101 | -8.413 | 1.00 | 2.26 | RIPD |
| ATOM | 483 | CD2 | HIS | 617 | -4.776 | 7.972 | -7.825 | 1.00 | 1.73 | RIPD |
| ATOM | 484 | HD2 | HIS | 617 | -4.244 | 8.739 | -7.282 | 1.00 | 2.46 | RIPD |
| ATOM | 485 | CE1 | HIS | 617 | -5.939 | 6.961 | -9.347 | 1.00 | 2.07 | RIPD |
| ATOM | 486 | HE1 | HIS | 617 | -6.509 | 6.758 | -10.242 | 1.00 | 2.79 | RIPD |
| ATOM | 487 | NE2 | HIS | 617 | -5.422 | 8.154 | -9.043 | 1.00 | 2.14 | RIPD |
| ATOM | 488 | C | HIS | 617 | -2.618 | 4.748 | -7.450 | 1.00 | 0.56 | RIPD |
| ATOM | 489 | O | HIS | 617 | -2.668 | 4.815 | -8.662 | 1.00 | 0.62 | RIPD |
| ATOM | 490 | N | ASP | 618 | -1.481 | 4.828 | -6.813 | 1.00 | 0.51 | RIPD |
| ATOM | 491 | HN | ASP | 618 | -1.462 | 4.771 | -5.835 | 1.00 | 0.49 | RIPD |
| ATOM | 492 | CA | ASP | 618 | -0.213 | 5.005 | -7.575 | 1.00 | 0.52 | RIPD |
| ATOM | 493 | HA | ASP | 618 | -0.374 | 5.696 | -8.389 | 1.00 | 0.60 | RIPD |
| ATOM | 494 | CB | ASP | 618 | 0.869 | 5.556 | -6.643 | 1.00 | 0.50 | RIPD |
| ATOM | 495 | HB1 | ASP | 618 | 1.829 | 5.500 | -7.134 | 1.00 | 0.52 | RIPD |
| ATOM | 496 | HB2 | ASP | 618 | 0.893 | 4.971 | -5.735 | 1.00 | 0.46 | RIPD |
| ATOM | 497 | CG | ASP | 618 | 0.556 | 7.015 | -6.305 | 1.00 | 0.65 | RIPD |
| ATOM | 498 | OD1 | ASP | 618 | -0.179 | 7.633 | -7.057 | 1.00 | 1.25 | RIPD |
| ATOM | 499 | OD2 | ASP | 618 | 1.058 | 7.489 | -5.298 | 1.00 | 1.33 | RIPD |
| ATOM | 500 | C | ASP | 618 | 0.237 | 3.654 | -8.135 | 1.00 | 0.52 | RIPD |
| ATOM | 501 | O | ASP | 618 | 0.885 | 3.580 | -9.160 | 1.00 | 0.57 | RIPD |
| ATOM | 502 | N | TYR | 619 | -0.100 | 2.584 | -7.467 | 1.00 | 0.51 | RIPD |

FIG. 6A-14

| ATOM | 503 | HN  | TYR | 619 | -0.621 | 2.665  | -6.642  | 1.00 | 0.52 | RIPD |
| ATOM | 504 | CA  | TYR | 619 | 0.310  | 1.238  | -7.959  | 1.00 | 0.54 | RIPD |
| ATOM | 505 | HA  | TYR | 619 | 1.320  | 1.285  | -8.337  | 1.00 | 0.53 | RIPD |
| ATOM | 506 | CB  | TYR | 619 | 0.244  | 0.234  | -6.806  | 1.00 | 0.60 | RIPD |
| ATOM | 507 | HB1 | TYR | 619 | 0.326  | -0.769 | -7.197  | 1.00 | 0.66 | RIPD |
| ATOM | 508 | HB2 | TYR | 619 | -0.698 | 0.343  | -6.288  | 1.00 | 0.64 | RIPD |
| ATOM | 509 | CG  | TYR | 619 | 1.380  | 0.493  | -5.845  | 1.00 | 0.59 | RIPD |
| ATOM | 510 | CD1 | TYR | 619 | 2.654  | -0.021 | -6.113  | 1.00 | 1.29 | RIPD |
| ATOM | 511 | HD1 | TYR | 619 | 2.824  | -0.602 | -7.008  | 1.00 | 2.14 | RIPD |
| ATOM | 512 | CD2 | TYR | 619 | 1.159  | 1.247  | -4.686  | 1.00 | 1.40 | RIPD |
| ATOM | 513 | HD2 | TYR | 619 | 0.176  | 1.644  | -4.479  | 1.00 | 2.28 | RIPD |
| ATOM | 514 | CE1 | TYR | 619 | 3.707  | 0.218  | -5.223  | 1.00 | 1.34 | RIPD |
| ATOM | 515 | HE1 | TYR | 619 | 4.690  | -0.179 | -5.430  | 1.00 | 2.21 | RIPD |
| ATOM | 516 | CE2 | TYR | 619 | 2.212  | 1.486  | -3.795  | 1.00 | 1.41 | RIPD |
| ATOM | 517 | HE2 | TYR | 619 | 2.042  | 2.068  | -2.901  | 1.00 | 2.27 | RIPD |
| ATOM | 518 | CZ  | TYR | 619 | 3.486  | 0.972  | -4.064  | 1.00 | 0.70 | RIPD |
| ATOM | 519 | OH  | TYR | 619 | 4.524  | 1.208  | -3.186  | 1.00 | 0.80 | RIPD |
| ATOM | 520 | HH  | TYR | 619 | 4.373  | 2.059  | -2.768  | 1.00 | 1.06 | RIPD |
| ATOM | 521 | C   | TYR | 619 | -0.634 | 0.791  | -9.078  | 1.00 | 0.59 | RIPD |
| ATOM | 522 | O   | TYR | 619 | -0.224 | 0.171  | -10.039 | 1.00 | 0.63 | RIPD |
| ATOM | 523 | N   | GLU | 620 | -1.897 | 1.098  | -8.960  | 1.00 | 0.65 | RIPD |
| ATOM | 524 | HN  | GLU | 620 | -2.209 | 1.597  | -8.176  | 1.00 | 0.66 | RIPD |
| ATOM | 525 | CA  | GLU | 620 | -2.866 | 0.688  | -10.015 | 1.00 | 0.74 | RIPD |
| ATOM | 526 | HA  | GLU | 620 | -2.828 | -0.384 | -10.142 | 1.00 | 0.78 | RIPD |
| ATOM | 527 | CB  | GLU | 620 | -4.279 | 1.100  | -9.596  | 1.00 | 0.84 | RIPD |
| ATOM | 528 | HB1 | GLU | 620 | -4.442 | 2.137  | -9.850  | 1.00 | 1.14 | RIPD |
| ATOM | 529 | HB2 | GLU | 620 | -4.391 | 0.968  | -8.529  | 1.00 | 1.23 | RIPD |
| ATOM | 530 | CG  | GLU | 620 | -5.304 | 0.231  | -10.329 | 1.00 | 1.19 | RIPD |
| ATOM | 531 | HG1 | GLU | 620 | -5.161 | -0.803 | -10.054 | 1.00 | 1.73 | RIPD |
| ATOM | 532 | HG2 | GLU | 620 | -5.173 | 0.343  | -11.395 | 1.00 | 1.61 | RIPD |
| ATOM | 533 | CD  | GLU | 620 | -6.717 | 0.669  | -9.939  | 1.00 | 1.43 | RIPD |
| ATOM | 534 | OE1 | GLU | 620 | -6.872 | 1.808  | -9.531  | 1.00 | 1.89 | RIPD |
| ATOM | 535 | OE2 | GLU | 620 | -7.621 | -0.143 | -10.055 | 1.00 | 1.99 | RIPD |
| ATOM | 536 | C   | GLU | 620 | -2.508 | 1.370  | -11.338 | 1.00 | 0.74 | RIPD |
| ATOM | 537 | O   | GLU | 620 | -2.514 | 0.756  | -12.386 | 1.00 | 0.80 | RIPD |
| ATOM | 538 | N   | ARG | 621 | -2.198 | 2.637  | -11.298 | 1.00 | 0.73 | RIPD |

FIG. 6A-15

| ATOM | 539 | HN | ARG | 621 | -2.201 | 3.115 | -10.442 | 1.00 | 0.71 | RIPD |
| ATOM | 540 | CA | ARG | 621 | -1.844 | 3.359 | -12.553 | 1.00 | 0.80 | RIPD |
| ATOM | 541 | HA | ARG | 621 | -2.661 | 3.281 | -13.255 | 1.00 | 0.89 | RIPD |
| ATOM | 542 | CB | ARG | 621 | -1.584 | 4.833 | -12.235 | 1.00 | 0.85 | RIPD |
| ATOM | 543 | HB1 | ARG | 621 | -0.742 | 4.913 | -11.564 | 1.00 | 0.80 | RIPD |
| ATOM | 544 | HB2 | ARG | 621 | -2.460 | 5.259 | -11.767 | 1.00 | 0.88 | RIPD |
| ATOM | 545 | CG | ARG | 621 | -1.277 | 5.589 | -13.528 | 1.00 | 0.98 | RIPD |
| ATOM | 546 | HG1 | ARG | 621 | -2.201 | 5.879 | -14.004 | 1.00 | 1.08 | RIPD |
| ATOM | 547 | HG2 | ARG | 621 | -0.713 | 4.951 | -14.193 | 1.00 | 1.03 | RIPD |
| ATOM | 548 | CD | ARG | 621 | -0.459 | 6.841 | -13.204 | 1.00 | 1.21 | RIPD |
| ATOM | 549 | HD1 | ARG | 621 | 0.588 | 6.643 | -13.382 | 1.00 | 1.59 | RIPD |
| ATOM | 550 | HD2 | ARG | 621 | -0.604 | 7.106 | -12.167 | 1.00 | 1.72 | RIPD |
| ATOM | 551 | NE | ARG | 621 | -0.906 | 7.966 | -14.071 | 1.00 | 1.89 | RIPD |
| ATOM | 552 | HE | ARG | 621 | -1.518 | 7.796 | -14.818 | 1.00 | 2.45 | RIPD |
| ATOM | 553 | CZ | ARG | 621 | -0.482 | 9.178 | -13.837 | 1.00 | 2.29 | RIPD |
| ATOM | 554 | NH1 | ARG | 621 | -0.413 | 9.620 | -12.611 | 1.00 | 2.51 | RIPD |
| ATOM | 555 | HH11 | ARG | 621 | -0.684 | 9.029 | -11.851 | 1.00 | 2.65 | RIPD |
| ATOM | 556 | HH12 | ARG | 621 | -0.088 | 10.548 | -12.432 | 1.00 | 2.91 | RIPD |
| ATOM | 557 | NH2 | ARG | 621 | -0.127 | 9.948 | -14.829 | 1.00 | 2.99 | RIPD |
| ATOM | 558 | HH21 | ARG | 621 | -0.180 | 9.609 | -15.769 | 1.00 | 3.38 | RIPD |
| ATOM | 559 | HH22 | ARG | 621 | 0.198 | 10.876 | -14.650 | 1.00 | 3.37 | RIPD |
| ATOM | 560 | C | ARG | 621 | -0.585 | 2.741 | -13.165 | 1.00 | 0.79 | RIPD |
| ATOM | 561 | O | ARG | 621 | -0.521 | 2.486 | -14.352 | 1.00 | 0.88 | RIPD |
| ATOM | 562 | N | ASP | 622 | 0.419 | 2.501 | -12.368 | 1.00 | 0.71 | RIPD |
| ATOM | 563 | HN | ASP | 622 | 0.349 | 2.716 | -11.414 | 1.00 | 0.66 | RIPD |
| ATOM | 564 | CA | ASP | 622 | 1.674 | 1.903 | -12.907 | 1.00 | 0.76 | RIPD |
| ATOM | 565 | HA | ASP | 622 | 1.980 | 2.448 | -13.788 | 1.00 | 0.88 | RIPD |
| ATOM | 566 | CB | ASP | 622 | 2.776 | 1.993 | -11.848 | 1.00 | 0.73 | RIPD |
| ATOM | 567 | HB1 | ASP | 622 | 3.553 | 1.280 | -12.076 | 1.00 | 0.95 | RIPD |
| ATOM | 568 | HB2 | ASP | 622 | 2.359 | 1.773 | -10.876 | 1.00 | 1.06 | RIPD |
| ATOM | 569 | CG | ASP | 622 | 3.367 | 3.404 | -11.844 | 1.00 | 1.01 | RIPD |
| ATOM | 570 | OD1 | ASP | 622 | 4.485 | 3.555 | -11.379 | 1.00 | 1.60 | RIPD |
| ATOM | 571 | OD2 | ASP | 622 | 2.692 | 4.309 | -12.306 | 1.00 | 1.71 | RIPD |
| ATOM | 572 | C | ASP | 622 | 1.439 | 0.434 | -13.276 | 1.00 | 0.76 | RIPD |
| ATOM | 573 | O | ASP | 622 | 2.241 | -0.176 | -13.956 | 1.00 | 0.89 | RIPD |
| ATOM | 574 | N | GLY | 623 | 0.354 | -0.145 | -12.834 | 1.00 | 0.72 | RIPD |

FIG. 6A-16

| ATOM | 575 | HN | GLY | 623 | -0.283 | 0.355 | -12.283 | 1.00 | 0.73 | RIPD |
|------|-----|------|-----|-----|--------|--------|---------|------|------|------|
| ATOM | 576 | CA | GLY | 623 | 0.091 | -1.574 | -13.166 | 1.00 | 0.77 | RIPD |
| ATOM | 577 | HA1 | GLY | 623 | 0.004 | -1.687 | -14.236 | 1.00 | 0.84 | RIPD |
| ATOM | 578 | HA2 | GLY | 623 | -0.827 | -1.892 | -12.692 | 1.00 | 0.82 | RIPD |
| ATOM | 579 | C | GLY | 623 | 1.253 | -2.429 | -12.660 | 1.00 | 0.74 | RIPD |
| ATOM | 580 | O | GLY | 623 | 1.999 | -3.000 | -13.431 | 1.00 | 0.83 | RIPD |
| ATOM | 581 | N | LEU | 624 | 1.420 | -2.512 | -11.369 | 1.00 | 0.75 | RIPD |
| ATOM | 582 | HN | LEU | 624 | 0.811 | -2.037 | -10.766 | 1.00 | 0.79 | RIPD |
| ATOM | 583 | CA | LEU | 624 | 2.540 | -3.319 | -10.812 | 1.00 | 0.82 | RIPD |
| ATOM | 584 | HA | LEU | 624 | 3.431 | -3.144 | -11.396 | 1.00 | 0.88 | RIPD |
| ATOM | 585 | CB | LEU | 624 | 2.791 | -2.903 | -9.361 | 1.00 | 0.96 | RIPD |
| ATOM | 586 | HB1 | LEU | 624 | 3.088 | -3.767 | -8.787 | 1.00 | 1.07 | RIPD |
| ATOM | 587 | HB2 | LEU | 624 | 1.884 | -2.489 | -8.945 | 1.00 | 1.00 | RIPD |
| ATOM | 588 | CG | LEU | 624 | 3.903 | -1.852 | -9.307 | 1.00 | 1.06 | RIPD |
| ATOM | 589 | HG | LEU | 624 | 4.051 | -1.541 | -8.283 | 1.00 | 1.56 | RIPD |
| ATOM | 590 | CD1 | LEU | 624 | 5.203 | -2.450 | -9.848 | 1.00 | 1.63 | RIPD |
| ATOM | 591 | HD11 | LEU | 624 | 5.633 | -1.779 | -10.577 | 1.00 | 2.11 | RIPD |
| ATOM | 592 | HD12 | LEU | 624 | 4.997 | -3.403 | -10.312 | 1.00 | 1.95 | RIPD |
| ATOM | 593 | HD13 | LEU | 624 | 5.899 | -2.591 | -9.034 | 1.00 | 2.21 | RIPD |
| ATOM | 594 | CD2 | LEU | 624 | 3.505 | -0.642 | -10.157 | 1.00 | 1.11 | RIPD |
| ATOM | 595 | HD21 | LEU | 624 | 3.409 | -0.942 | -11.190 | 1.00 | 1.68 | RIPD |
| ATOM | 596 | HD22 | LEU | 624 | 4.264 | 0.122 | -10.074 | 1.00 | 1.54 | RIPD |
| ATOM | 597 | HD23 | LEU | 624 | 2.561 | -0.251 | -9.807 | 1.00 | 1.56 | RIPD |
| ATOM | 598 | C | LEU | 624 | 2.184 | -4.808 | -10.861 | 1.00 | 0.82 | RIPD |
| ATOM | 599 | O | LEU | 624 | 1.157 | -5.195 | -11.382 | 1.00 | 1.38 | RIPD |
| ATOM | 600 | N | LYS | 625 | 3.030 | -5.646 | -10.322 | 1.00 | 0.97 | RIPD |
| ATOM | 601 | HN | LYS | 625 | 3.853 | -5.312 | -9.908 | 1.00 | 1.48 | RIPD |
| ATOM | 602 | CA | LYS | 625 | 2.746 | -7.110 | -10.336 | 1.00 | 0.97 | RIPD |
| ATOM | 603 | HA | LYS | 625 | 1.678 | -7.269 | -10.319 | 1.00 | 0.98 | RIPD |
| ATOM | 604 | CB | LYS | 625 | 3.334 | -7.726 | -11.608 | 1.00 | 1.14 | RIPD |
| ATOM | 605 | HB1 | LYS | 625 | 3.137 | -8.787 | -11.620 | 1.00 | 1.49 | RIPD |
| ATOM | 606 | HB2 | LYS | 625 | 4.400 | -7.557 | -11.630 | 1.00 | 1.36 | RIPD |
| ATOM | 607 | CG | LYS | 625 | 2.688 | -7.078 | -12.834 | 1.00 | 1.64 | RIPD |
| ATOM | 608 | HG1 | LYS | 625 | 3.146 | -6.119 | -13.018 | 1.00 | 2.11 | RIPD |
| ATOM | 609 | HG2 | LYS | 625 | 1.630 | -6.945 | -12.655 | 1.00 | 2.13 | RIPD |
| ATOM | 610 | CD | LYS | 625 | 2.889 | -7.979 | -14.055 | 1.00 | 1.71 | RIPD |

FIG. 6A-17

| ATOM | 611 | HD1 | LYS | 625 | 2.313 | -8.884 | -13.933 | 1.00 | 1.84 | RIPD |
| --- | --- | --- | --- | --- | --- | --- | --- | --- | --- | --- |
| ATOM | 612 | HD2 | LYS | 625 | 3.936 | -8.228 | -14.149 | 1.00 | 1.67 | RIPD |
| ATOM | 613 | CE | LYS | 625 | 2.422 | -7.246 | -15.313 | 1.00 | 2.59 | RIPD |
| ATOM | 614 | HE1 | LYS | 625 | 2.770 | -6.224 | -15.284 | 1.00 | 3.07 | RIPD |
| ATOM | 615 | HE2 | LYS | 625 | 1.343 | -7.259 | -15.358 | 1.00 | 2.98 | RIPD |
| ATOM | 616 | NZ | LYS | 625 | 2.977 | -7.925 | -16.518 | 1.00 | 2.85 | RIPD |
| ATOM | 617 | HZ1 | LYS | 625 | 3.855 | -7.452 | -16.810 | 1.00 | 3.11 | RIPD |
| ATOM | 618 | HZ2 | LYS | 625 | 2.283 | -7.877 | -17.293 | 1.00 | 3.27 | RIPD |
| ATOM | 619 | HZ3 | LYS | 625 | 3.180 | -8.919 | -16.294 | 1.00 | 2.90 | RIPD |
| ATOM | 620 | C | LYS | 625 | 3.380 | -7.769 | -9.106 | 1.00 | 0.87 | RIPD |
| ATOM | 621 | O | LYS | 625 | 3.772 | -7.104 | -8.167 | 1.00 | 0.80 | RIPD |
| ATOM | 622 | N | GLU | 626 | 3.480 | -9.072 | -9.101 | 1.00 | 0.91 | RIPD |
| ATOM | 623 | HN | GLU | 626 | 3.154 | -9.589 | -9.866 | 1.00 | 1.00 | RIPD |
| ATOM | 624 | CA | GLU | 626 | 4.083 | -9.776 | -7.931 | 1.00 | 0.88 | RIPD |
| ATOM | 625 | HA | GLU | 626 | 3.453 | -9.635 | -7.065 | 1.00 | 0.81 | RIPD |
| ATOM | 626 | CB | GLU | 626 | 4.194 | -11.270 | -8.240 | 1.00 | 0.99 | RIPD |
| ATOM | 627 | HB1 | GLU | 626 | 5.065 | -11.675 | -7.749 | 1.00 | 1.36 | RIPD |
| ATOM | 628 | HB2 | GLU | 626 | 4.282 | -11.412 | -9.307 | 1.00 | 1.35 | RIPD |
| ATOM | 629 | CG | GLU | 626 | 2.944 | -11.990 | -7.730 | 1.00 | 1.40 | RIPD |
| ATOM | 630 | HG1 | GLU | 626 | 2.091 | -11.692 | -8.321 | 1.00 | 1.89 | RIPD |
| ATOM | 631 | HG2 | GLU | 626 | 2.774 | -11.727 | -6.696 | 1.00 | 1.85 | RIPD |
| ATOM | 632 | CD | GLU | 626 | 3.139 | -13.502 | -7.847 | 1.00 | 1.79 | RIPD |
| ATOM | 633 | OE1 | GLU | 626 | 3.477 | -13.955 | -8.929 | 1.00 | 2.33 | RIPD |
| ATOM | 634 | OE2 | GLU | 626 | 2.948 | -14.183 | -6.853 | 1.00 | 2.26 | RIPD |
| ATOM | 635 | C | GLU | 626 | 5.476 | -9.211 | -7.644 | 1.00 | 0.87 | RIPD |
| ATOM | 636 | O | GLU | 626 | 5.909 | -9.151 | -6.510 | 1.00 | 0.83 | RIPD |
| ATOM | 637 | N | LYS | 627 | 6.183 | -8.796 | -8.660 | 1.00 | 0.93 | RIPD |
| ATOM | 638 | HN | LYS | 627 | 5.817 | -8.853 | -9.567 | 1.00 | 0.97 | RIPD |
| ATOM | 639 | CA | LYS | 627 | 7.549 | -8.236 | -8.441 | 1.00 | 0.94 | RIPD |
| ATOM | 640 | HA | LYS | 627 | 8.127 | -8.929 | -7.848 | 1.00 | 0.98 | RIPD |
| ATOM | 641 | CB | LYS | 627 | 8.237 | -8.029 | -9.791 | 1.00 | 1.08 | RIPD |
| ATOM | 642 | HB1 | LYS | 627 | 8.757 | -7.083 | -9.789 | 1.00 | 1.49 | RIPD |
| ATOM | 643 | HB2 | LYS | 627 | 7.496 | -8.033 | -10.577 | 1.00 | 1.46 | RIPD |
| ATOM | 644 | CG | LYS | 627 | 9.242 | -9.158 | -10.028 | 1.00 | 1.65 | RIPD |
| ATOM | 645 | HG1 | LYS | 627 | 8.810 | -10.097 | -9.716 | 1.00 | 2.16 | RIPD |
| ATOM | 646 | HG2 | LYS | 627 | 10.140 | -8.967 | -9.458 | 1.00 | 2.31 | RIPD |

FIG. 6A-18

| | | | | | | | | | |
|---|---|---|---|---|---|---|---|---|---|
| ATOM | 647 | CD | LYS | 627 | 9.586 | -9.229 | -11.517 | 1.00 | 1.76 | RIPD |
| ATOM | 648 | HD1 | LYS | 627 | 8.816 | -8.734 | -12.088 | 1.00 | 2.08 | RIPD |
| ATOM | 649 | HD2 | LYS | 627 | 9.653 | -10.264 | -11.822 | 1.00 | 1.86 | RIPD |
| ATOM | 650 | CE | LYS | 627 | 10.927 | -8.535 | -11.765 | 1.00 | 2.58 | RIPD |
| ATOM | 651 | HE1 | LYS | 627 | 11.668 | -8.930 | -11.086 | 1.00 | 2.91 | RIPD |
| ATOM | 652 | HE2 | LYS | 62 | 10.818 | -7.473 | -11.600 | 1.00 | 3.15 | RIPD |
| ATOM | 653 | NZ | LYS | 627 | 11.360 | -8.779 | -13.170 | 1.00 | 3.13 | RIPD |
| ATOM | 654 | HZ1 | LYS | 627 | 11.021 | -9.711 | -13.480 | 1.00 | 3.53 | RIPD |
| ATOM | 655 | HZ2 | LYS | 627 | 12.399 | -8.752 | -13.221 | 1.00 | 3.24 | RIPD |
| ATOM | 656 | HZ3 | LYS | 627 | 10.963 | -8.044 | -13.788 | 1.00 | 3.59 | RIPD |
| ATOM | 657 | C | LYS | 627 | 7.455 | -6.893 | -7.704 | 1.00 | 0.81 | RIPD |
| ATOM | 658 | O | LYS | 627 | 8.452 | -6.343 | -7.277 | 1.00 | 0.79 | RIPD |
| ATOM | 659 | N | VAL | 628 | 6.270 | -6.356 | -7.554 | 1.00 | 0.75 | RIPD |
| ATOM | 660 | HN | VAL | 628 | 5.479 | -6.808 | -7.907 | 1.00 | 0.78 | RIPD |
| ATOM | 661 | CA | VAL | 628 | 6.116 | -5.049 | -6.849 | 1.00 | 0.64 | RIPD |
| ATOM | 662 | HA | VAL | 628 | 6.500 | -4.258 | -7.475 | 1.00 | 0.67 | RIPD |
| ATOM | 663 | CB | VAL | 628 | 4.635 | -4.797 | -6.566 | 1.00 | 0.62 | RIPD |
| ATOM | 664 | HB | VAL | 628 | 4.087 | -4.795 | -7.495 | 1.00 | 0.68 | RIPD |
| ATOM | 665 | CG1 | VAL | 628 | 4.090 | -5.899 | -5.655 | 1.00 | 0.62 | RIPD |
| ATOM | 666 | HG11 | VAL | 628 | 4.337 | -5.672 | -4.629 | 1.00 | 1.24 | RIPD |
| ATOM | 667 | HG12 | VAL | 628 | 4.531 | -6.845 | -5.931 | 1.00 | 1.18 | RIPD |
| ATOM | 668 | HG13 | VAL | 628 | 3.017 | -5.956 | -5.763 | 1.00 | 1.16 | RIPD |
| ATOM | 669 | CG2 | VAL | 628 | 4.476 | -3.442 | -5.874 | 1.00 | 0.58 | RIPD |
| ATOM | 670 | HG21 | VAL | 628 | 3.433 | -3.162 | -5.866 | 1.00 | 1.24 | RIPD |
| ATOM | 671 | HG22 | VAL | 628 | 5.045 | -2.696 | -6.408 | 1.00 | 1.09 | RIPD |
| ATOM | 672 | HG23 | VAL | 628 | 4.837 | -3.512 | -4.859 | 1.00 | 1.17 | RIPD |
| ATOM | 673 | C | VAL | 628 | 6.889 | -5.071 | -5.527 | 1.00 | 0.57 | RIPD |
| ATOM | 674 | O | VAL | 628 | 7.297 | -4.046 | -5.023 | 1.00 | 0.52 | RIPD |
| ATOM | 675 | N | TYR | 629 | 7.098 | -6.229 | -4.963 | 1.00 | 0.61 | RIPD |
| ATOM | 676 | HN | TYR | 629 | 6.763 | -7.048 | -5.384 | 1.00 | 0.67 | RIPD |
| ATOM | 677 | CA | TYR | 629 | 7.850 | -6.305 | -3.678 | 1.00 | 0.59 | RIPD |
| ATOM | 678 | HA | TYR | 629 | 7.284 | -5.814 | -2.900 | 1.00 | 0.55 | RIPD |
| ATOM | 679 | CB | TYR | 629 | 8.068 | -7.776 | -3.304 | 1.00 | 0.69 | RIPD |
| ATOM | 680 | HB1 | TYR | 629 | 8.581 | -8.279 | -4.110 | 1.00 | 0.74 | RIPD |
| ATOM | 681 | HB2 | TYR | 629 | 7.111 | -8.248 | -3.138 | 1.00 | 0.71 | RIPD |
| ATOM | 682 | CG | TYR | 629 | 8.898 | -7.868 | -2.045 | 1.00 | 0.73 | RIPD |

FIG. 6A-19

| ATOM | 683 | CD1 | TYR | 629 | 10.232 | -8.289 | -2.117 | 1.00 | 1.44 | RIPD |
| --- | --- | --- | --- | --- | --- | --- | --- | --- | --- | --- |
| ATOM | 684 | HD1 | TYR | 629 | 10.666 | -8.546 | -3.071 | 1.00 | 2.24 | RIPD |
| ATOM | 685 | CD2 | TYR | 629 | 8.335 | -7.534 | -0.808 | 1.00 | 1.30 | RIPD |
| ATOM | 686 | HD2 | TYR | 629 | 7.307 | -7.210 | -0.752 | 1.00 | 2.07 | RIPD |
| ATOM | 687 | CE1 | TYR | 629 | 11.003 | -8.374 | -0.952 | 1.00 | 1.48 | RIPD |
| ATOM | 688 | HE1 | TYR | 629 | 12.032 | -8.699 | -1.008 | 1.00 | 2.28 | RIPD |
| ATOM | 689 | CE2 | TYR | 629 | 9.107 | -7.620 | 0.358 | 1.00 | 1.36 | RIPD |
| ATOM | 690 | HE2 | TYR | 629 | 8.673 | -7.363 | 1.313 | 1.00 | 2.14 | RIPD |
| ATOM | 691 | CZ | TYR | 629 | 10.440 | -8.040 | 0.286 | 1.00 | 0.89 | RIPD |
| ATOM | 692 | OH | TYR | 629 | 11.200 | -8.125 | 1.435 | 1.00 | 1.00 | RIPD |
| ATOM | 693 | HH | TYR | 629 | 11.286 | -7.241 | 1.799 | 1.00 | 1.53 | RIPD |
| ATOM | 694 | C | TYR | 629 | 9.204 | -5.605 | -3.845 | 1.00 | 0.59 | RIPD |
| ATOM | 695 | O | TYR | 629 | 9.500 | -4.631 | -3.179 | 1.00 | 0.54 | RIPD |
| ATOM | 696 | N | GLN | 630 | 10.024 | -6.086 | -4.738 | 1.00 | 0.65 | RIPD |
| ATOM | 697 | HN | GLN | 630 | 9.766 | -6.867 | -5.274 | 1.00 | 0.71 | RIPD |
| ATOM | 698 | CA | GLN | 630 | 11.348 | -5.438 | -4.949 | 1.00 | 0.67 | RIPD |
| ATOM | 699 | HA | GLN | 630 | 11.926 | -5.492 | -4.038 | 1.00 | 0.67 | RIPD |
| ATOM | 700 | CB | GLN | 630 | 12.096 | -6.153 | -6.076 | 1.00 | 0.78 | RIPD |
| ATOM | 701 | HB1 | GLN | 630 | 12.978 | -5.588 | -6.338 | 1.00 | 1.13 | RIPD |
| ATOM | 702 | HB2 | GLN | 630 | 11.451 | -6.236 | -6.940 | 1.00 | 1.01 | RIPD |
| ATOM | 703 | CG | GLN | 630 | 12.509 | -7.551 | -5.610 | 1.00 | 1.33 | RIPD |
| ATOM | 704 | HG1 | GLN | 630 | 11.645 | -8.071 | -5.224 | 1.00 | 1.69 | RIPD |
| ATOM | 705 | HG2 | GLN | 630 | 13.255 | -7.465 | -4.833 | 1.00 | 1.76 | RIPD |
| ATOM | 706 | CD | GLN | 630 | 13.087 | -8.332 | -6.791 | 1.00 | 1.41 | RIPD |
| ATOM | 707 | OE1 | GLN | 630 | 12.716 | -8.104 | -7.925 | 1.00 | 1.08 | RIPD |
| ATOM | 708 | NE2 | GLN | 630 | 13.987 | -9.251 | -6.572 | 1.00 | 2.04 | RIPD |
| ATOM | 709 | HE21 | GLN | 630 | 14.287 | -9.436 | -5.657 | 1.00 | 2.52 | RIPD |
| ATOM | 710 | HE22 | GLN | 630 | 14.364 | -9.757 | -7.322 | 1.00 | 2.09 | RIPD |
| ATOM | 711 | C | GLN | 630 | 11.125 | -3.974 | -5.328 | 1.00 | 0.60 | RIPD |
| ATOM | 712 | O | GLN | 630 | 11.785 | -3.079 | -4.828 | 1.00 | 0.57 | RIPD |
| ATOM | 713 | N | MET | 631 | 10.190 | -3.719 | -6.202 | 1.00 | 0.62 | RIPD |
| ATOM | 714 | HN | MET | 631 | 9.665 | -4.452 | -6.588 | 1.00 | 0.66 | RIPD |
| ATOM | 715 | CA | MET | 631 | 9.918 | -2.315 | -6.605 | 1.00 | 0.60 | RIPD |
| ATOM | 716 | HA | MET | 631 | 10.810 | -1.887 | -7.039 | 1.00 | 0.64 | RIPD |
| ATOM | 717 | CB | MET | 631 | 8.783 | -2.280 | -7.631 | 1.00 | 0.69 | RIPD |
| ATOM | 718 | HB1 | MET | 631 | 7.833 | -2.325 | -7.121 | 1.00 | 1.09 | RIPD |

FIG. 6A-20

| ATOM | 719 | HB2  | MET | 631 | 8.876  | -3.125 | -8.298 | 1.00 | 1.20 | RIPD |
| ATOM | 720 | CG   | MET | 631 | 8.869  | -0.980 | -8.435 | 1.00 | 1.10 | RIPD |
| ATOM | 721 | HG1  | MET | 631 | 9.372  | -1.172 | -9.372 | 1.00 | 1.48 | RIPD |
| ATOM | 722 | HG2  | MET | 631 | 9.425  | -0.246 | -7.873 | 1.00 | 1.71 | RIPD |
| ATOM | 723 | SD   | MET | 631 | 7.203  | -0.349 | -8.765 | 1.00 | 1.93 | RIPD |
| ATOM | 724 | CE   | MET | 631 | 6.655  | -0.206 | -7.046 | 1.00 | 2.68 | RIPD |
| ATOM | 725 | HE1  | MET | 631 | 7.504  | -0.322 | -6.386 | 1.00 | 2.95 | RIPD |
| ATOM | 726 | HE2  | MET | 631 | 5.929  | -0.974 | -6.833 | 1.00 | 3.10 | RIPD |
| ATOM | 727 | HE3  | MET | 631 | 6.203  | 0.765  | -6.894 | 1.00 | 3.07 | RIPD |
| ATOM | 728 | C    | MET | 631 | 9.520  | -1.511 | -5.367 | 1.00 | 0.52 | RIPD |
| ATOM | 729 | O    | MET | 631 | 9.894  | -0.371 | -5.213 | 1.00 | 0.52 | RIPD |
| ATOM | 730 | N    | LEU | 632 | 8.773  | -2.097 | -4.473 | 1.00 | 0.50 | RIPD |
| ATOM | 731 | HN   | LEU | 632 | 8.483  | -3.024 | -4.607 | 1.00 | 0.54 | RIPD |
| ATOM | 732 | CA   | LEU | 632 | 8.368  | -1.357 | -3.245 | 1.00 | 0.47 | RIPD |
| ATOM | 733 | HA   | LEU | 632 | 7.744  | -0.519 | -3.516 | 1.00 | 0.48 | RIPD |
| ATOM | 734 | CB   | LEU | 632 | 7.596  | -2.291 | -2.311 | 1.00 | 0.48 | RIPD |
| ATOM | 735 | HB1  | LEU | 632 | 7.536  | -1.848 | -1.328 | 1.00 | 0.49 | RIPD |
| ATOM | 736 | HB2  | LEU | 632 | 8.108  | -3.239 | -2.247 | 1.00 | 0.51 | RIPD |
| ATOM | 737 | CG   | LEU | 632 | 6.186  | -2.508 | -2.856 | 1.00 | 0.49 | RIPD |
| ATOM | 738 | HG   | LEU | 632 | 6.210  | -2.485 | -3.936 | 1.00 | 0.52 | RIPD |
| ATOM | 739 | CD1  | LEU | 632 | 5.664  | -3.867 | -2.386 | 1.00 | 0.58 | RIPD |
| ATOM | 740 | HD11 | LEU | 632 | 6.446  | -4.389 | -1.854 | 1.00 | 1.21 | RIPD |
| ATOM | 741 | HD12 | LEU | 632 | 5.360  | -4.452 | -3.242 | 1.00 | 1.25 | RIPD |
| ATOM | 742 | HD13 | LEU | 632 | 4.819  | -3.722 | -1.731 | 1.00 | 1.00 | RIPD |
| ATOM | 743 | CD2  | LEU | 632 | 5.264  | -1.402 | -2.338 | 1.00 | 0.48 | RIPD |
| ATOM | 744 | HD21 | LEU | 632 | 5.821  | -0.480 | -2.252 | 1.00 | 1.09 | RIPD |
| ATOM | 745 | HD22 | LEU | 632 | 4.876  | -1.680 | -1.369 | 1.00 | 1.15 | RIPD |
| ATOM | 746 | HD23 | LEU | 632 | 4.445  | -1.264 | -3.028 | 1.00 | 1.13 | RIPD |
| ATOM | 747 | C    | LEU | 632 | 9.622  | -0.852 | -2.530 | 1.00 | 0.47 | RIPD |
| ATOM | 748 | O    | LEU | 632 | 9.610  | 0.178  | -1.885 | 1.00 | 0.52 | RIPD |
| ATOM | 749 | N    | GLN | 633 | 10.704 | -1.572 | -2.641 | 1.00 | 0.47 | RIPD |
| ATOM | 750 | HN   | GLN | 633 | 10.690 | -2.401 | -3.165 | 1.00 | 0.48 | RIPD |
| ATOM | 751 | CA   | GLN | 633 | 11.958 | -1.136 | -1.967 | 1.00 | 0.50 | RIPD |
| ATOM | 752 | HA   | GLN | 633 | 11.745 | -0.902 | -0.933 | 1.00 | 0.53 | RIPD |
| ATOM | 753 | CB   | GLN | 633 | 12.988 | -2.265 | -2.029 | 1.00 | 0.56 | RIPD |
| ATOM | 754 | HB1  | GLN | 633 | 13.903 | -1.945 | -1.554 | 1.00 | 0.67 | RIPD |

FIG. 6A-21

| ATOM | 755 | HB2  | GLN | 633 | 13.186 | -2.514 | -3.062 | 1.00 | 0.70 | RIPD |
| ---- | --- | ---- | --- | --- | ------ | ------ | ------ | ---- | ---- | ---- |
| ATOM | 756 | CG   | GLN | 633 | 12.442 | -3.496 | -1.302 | 1.00 | 0.71 | RIPD |
| ATOM | 757 | HG1  | GLN | 633 | 11.686 | -3.967 | -1.911 | 1.00 | 0.95 | RIPD |
| ATOM | 758 | HG2  | GLN | 633 | 12.010 | -3.194 | -0.359 | 1.00 | 1.06 | RIPD |
| ATOM | 759 | CD   | GLN | 633 | 13.580 | -4.486 | -1.050 | 1.00 | 1.04 | RIPD |
| ATOM | 760 | OE1  | GLN | 633 | 14.599 | -4.440 | -1.710 | 1.00 | 1.36 | RIPD |
| ATOM | 761 | NE2  | GLN | 633 | 13.449 | -5.387 | -0.114 | 1.00 | 1.62 | RIPD |
| ATOM | 762 | HE21 | GLN | 633 | 12.628 | -5.424 | 0.418  | 1.00 | 1.95 | RIPD |
| ATOM | 763 | HE22 | GLN | 633 | 14.173 | -6.026 | 0.055  | 1.00 | 1.95 | RIPD |
| ATOM | 764 | C    | GLN | 633 | 12.520 | 0.107  | -2.666 | 1.00 | 0.51 | RIPD |
| ATOM | 765 | O    | GLN | 633 | 12.799 | 1.109  | -2.036 | 1.00 | 0.56 | RIPD |
| ATOM | 766 | N    | LYS | 634 | 12.697 | 0.053  | -3.960 | 1.00 | 0.51 | RIPD |
| ATOM | 767 | HN   | LYS | 634 | 12.472 | -0.764 | -4.453 | 1.00 | 0.52 | RIPD |
| ATOM | 768 | CA   | LYS | 634 | 13.250 | 1.237  | -4.687 | 1.00 | 0.55 | RIPD |
| ATOM | 769 | HA   | LYS | 634 | 14.030 | 1.690  | -4.092 | 1.00 | 0.59 | RIPD |
| ATOM | 770 | CB   | LYS | 634 | 13.833 | 0.786  | -6.029 | 1.00 | 0.61 | RIPD |
| ATOM | 771 | HB1  | LYS | 634 | 14.320 | 1.622  | -6.509 | 1.00 | 1.09 | RIPD |
| ATOM | 772 | HB2  | LYS | 634 | 13.038 | 0.420  | -6.662 | 1.00 | 0.99 | RIPD |
| ATOM | 773 | CG   | LYS | 634 | 14.855 | -0.328 | -5.794 | 1.00 | 1.06 | RIPD |
| ATOM | 774 | HG1  | LYS | 634 | 14.352 | -1.201 | -5.405 | 1.00 | 1.60 | RIPD |
| ATOM | 775 | HG2  | LYS | 634 | 15.596 | 0.007  | -5.083 | 1.00 | 1.64 | RIPD |
| ATOM | 776 | CD   | LYS | 634 | 15.539 | -0.683 | -7.115 | 1.00 | 1.26 | RIPD |
| ATOM | 777 | HD1  | LYS | 634 | 16.017 | 0.195  | -7.521 | 1.00 | 1.56 | RIPD |
| ATOM | 778 | HD2  | LYS | 634 | 14.801 | -1.048 | -7.816 | 1.00 | 1.41 | RIPD |
| ATOM | 779 | CE   | LYS | 634 | 16.591 | -1.766 | -6.870 | 1.00 | 2.07 | RIPD |
| ATOM | 780 | HE1  | LYS | 634 | 16.101 | -2.719 | -6.733 | 1.00 | 2.55 | RIPD |
| ATOM | 781 | HE2  | LYS | 634 | 17.159 | -1.522 | -5.985 | 1.00 | 2.38 | RIPD |
| ATOM | 782 | NZ   | LYS | 634 | 17.507 | -1.843 | -8.043 | 1.00 | 2.60 | RIPD |
| ATOM | 783 | HZ1  | LYS | 634 | 18.458 | -2.115 | -7.723 | 1.00 | 3.02 | RIPD |
| ATOM | 784 | HZ2  | LYS | 634 | 17.550 | -0.915 | -8.510 | 1.00 | 2.92 | RIPD |
| ATOM | 785 | HZ3  | LYS | 634 | 17.154 | -2.554 | -8.714 | 1.00 | 2.86 | RIPD |
| ATOM | 786 | C    | LYS | 634 | 12.138 | 2.263  | -4.933 | 1.00 | 0.50 | RIPD |
| ATOM | 787 | O    | LYS | 634 | 12.295 | 3.438  | -4.671 | 1.00 | 0.54 | RIPD |
| ATOM | 788 | N    | TRP | 635 | 11.017 | 1.821  | -5.435 | 1.00 | 0.46 | RIPD |
| ATOM | 789 | HN   | TRP | 635 | 10.921 | 0.867  | -5.636 | 1.00 | 0.46 | RIPD |
| ATOM | 790 | CA   | TRP | 635 | 9.878  | 2.751  | -5.707 | 1.00 | 0.45 | RIPD |

FIG. 6A-22

| ATOM | 791 | HA   | TRP | 635 | 10.104 | 3.357 | -6.572 | 1.00 | 0.50 | RIPD |
|------|-----|------|-----|-----|--------|-------|--------|------|------|------|
| ATOM | 792 | CB   | TRP | 635 | 8.619  | 1.924 | -5.978 | 1.00 | 0.46 | RIPD |
| ATOM | 793 | HB1  | TRP | 635 | 8.170  | 1.637 | -5.038 | 1.00 | 0.44 | RIPD |
| ATOM | 794 | HB2  | TRP | 635 | 8.886  | 1.038 | -6.532 | 1.00 | 0.51 | RIPD |
| ATOM | 795 | CG   | TRP | 635 | 7.637  | 2.724 | -6.773 | 1.00 | 0.49 | RIPD |
| ATOM | 796 | CD1  | TRP | 635 | 7.626  | 2.818 | -8.122 | 1.00 | 0.58 | RIPD |
| ATOM | 797 | HD1  | TRP | 635 | 8.324  | 2.337 | -8.792 | 1.00 | 0.64 | RIPD |
| ATOM | 798 | CD2  | TRP | 635 | 6.519  | 3.528 | -6.297 | 1.00 | 0.49 | RIPD |
| ATOM | 799 | NE1  | TRP | 635 | 6.573  | 3.630 | -8.505 | 1.00 | 0.61 | RIPD |
| ATOM | 800 | HE1  | TRP | 635 | 6.345  | 3.860 | -9.430 | 1.00 | 0.70 | RIPD |
| ATOM | 801 | CE2  | TRP | 635 | 5.862  | 4.094 | -7.416 | 1.00 | 0.55 | RIPD |
| ATOM | 802 | CE3  | TRP | 635 | 6.016  | 3.820 | -5.016 | 1.00 | 0.51 | RIPD |
| ATOM | 803 | HE3  | TRP | 635 | 6.496  | 3.402 | -4.143 | 1.00 | 0.52 | RIPD |
| ATOM | 804 | CZ2  | TRP | 635 | 4.747  | 4.920 | -7.268 | 1.00 | 0.58 | RIPD |
| ATOM | 805 | HZ2  | TRP | 635 | 4.263  | 5.340 | -8.138 | 1.00 | 0.65 | RIPD |
| ATOM | 806 | CZ3  | TRP | 635 | 4.894  | 4.651 | -4.864 | 1.00 | 0.57 | RIPD |
| ATOM | 807 | HZ3  | TRP | 635 | 4.516  | 4.868 | -3.876 | 1.00 | 0.64 | RIPD |
| ATOM | 808 | CH2  | TRP | 635 | 4.260  | 5.200 | -5.988 | 1.00 | 0.59 | RIPD |
| ATOM | 809 | HH2  | TRP | 635 | 3.397  | 5.837 | -5.864 | 1.00 | 0.64 | RIPD |
| ATOM | 810 | C    | TRP | 635 | 9.638  | 3.658 | -4.494 | 1.00 | 0.43 | RIPD |
| ATOM | 811 | O    | TRP | 635 | 9.273  | 4.809 | -4.631 | 1.00 | 0.48 | RIPD |
| ATOM | 812 | N    | VAL | 636 | 9.838  | 3.147 | -3.310 | 1.00 | 0.40 | RIPD |
| ATOM | 813 | HN   | VAL | 636 | 10.130 | 2.216 | -3.221 | 1.00 | 0.39 | RIPD |
| ATOM | 814 | CA   | VAL | 636 | 9.618  | 3.979 | -2.093 | 1.00 | 0.43 | RIPD |
| ATOM | 815 | HA   | VAL | 636 | 8.819  | 4.682 | -2.278 | 1.00 | 0.45 | RIPD |
| ATOM | 816 | CB   | VAL | 636 | 9.237  | 3.075 | -0.919 | 1.00 | 0.45 | RIPD |
| ATOM | 817 | HB   | VAL | 636 | 10.032 | 2.365 | -0.739 | 1.00 | 0.45 | RIPD |
| ATOM | 818 | CG1  | VAL | 636 | 9.020  | 3.926 | 0.333  | 1.00 | 0.53 | RIPD |
| ATOM | 819 | HG11 | VAL | 636 | 8.315  | 3.433 | 0.986  | 1.00 | 1.17 | RIPD |
| ATOM | 820 | HG12 | VAL | 636 | 8.632  | 4.893 | 0.049  | 1.00 | 1.19 | RIPD |
| ATOM | 821 | HG13 | VAL | 636 | 9.961  | 4.053 | 0.849  | 1.00 | 1.09 | RIPD |
| ATOM | 822 | CG2  | VAL | 636 | 7.946  | 2.326 | -1.255 | 1.00 | 0.44 | RIPD |
| ATOM | 823 | HG21 | VAL | 636 | 7.971  | 1.345 | -0.804 | 1.00 | 1.11 | RIPD |
| ATOM | 824 | HG22 | VAL | 636 | 7.855  | 2.227 | -2.327 | 1.00 | 1.12 | RIPD |
| ATOM | 825 | HG23 | VAL | 636 | 7.100  | 2.877 | -0.871 | 1.00 | 1.09 | RIPD |
| ATOM | 826 | C    | VAL | 636 | 10.900 | 4.742 | -1.754 | 1.00 | 0.50 | RIPD |

FIG. 6A-23

| | | | | | | | | | |
|---|---|---|---|---|---|---|---|---|---|
| ATOM | 827 | O | VAL | 636 | 10.888 | 5.944 | -1.570 | 1.00 | 0.54 | RIPD |
| ATOM | 828 | N | MET | 637 | 12.006 | 4.056 | -1.669 | 1.00 | 0.58 | RIPD |
| ATOM | 829 | HN | MET | 637 | 11.995 | 3.088 | -1.820 | 1.00 | 0.59 | RIPD |
| ATOM | 830 | CA | MET | 637 | 13.286 | 4.745 | -1.340 | 1.00 | 0.70 | RIPD |
| ATOM | 831 | HA | MET | 637 | 13.189 | 5.248 | -0.389 | 1.00 | 0.73 | RIPD |
| ATOM | 832 | CB | MET | 637 | 14.413 | 3.714 | -1.259 | 1.00 | 0.83 | RIPD |
| ATOM | 833 | HB1 | MET | 637 | 15.365 | 4.223 | -1.219 | 1.00 | 0.92 | RIPD |
| ATOM | 834 | HB2 | MET | 637 | 14.381 | 3.077 | -2.131 | 1.00 | 0.84 | RIPD |
| ATOM | 835 | CG | MET | 637 | 14.239 | 2.866 | 0.002 | 1.00 | 0.89 | RIPD |
| ATOM | 836 | HG1 | MET | 637 | 13.416 | 2.180 | -0.136 | 1.00 | 0.78 | RIPD |
| ATOM | 837 | HG2 | MET | 637 | 14.033 | 3.511 | 0.844 | 1.00 | 0.95 | RIPD |
| ATOM | 838 | SD | MET | 637 | 15.757 | 1.932 | 0.316 | 1.00 | 1.13 | RIPD |
| ATOM | 839 | CE | MET | 637 | 15.110 | 0.294 | -0.102 | 1.00 | 0.75 | RIPD |
| ATOM | 840 | HE1 | MET | 637 | 14.419 | -0.025 | 0.665 | 1.00 | 1.24 | RIPD |
| ATOM | 841 | HE2 | MET | 637 | 15.923 | -0.410 | -0.166 | 1.00 | 1.35 | RIPD |
| ATOM | 842 | HE3 | MET | 637 | 14.602 | 0.342 | -1.056 | 1.00 | 1.40 | RIPD |
| ATOM | 843 | C | MET | 637 | 13.609 | 5.772 | -2.428 | 1.00 | 0.72 | RIPD |
| ATOM | 844 | O | MET | 637 | 14.334 | 6.720 | -2.204 | 1.00 | 0.78 | RIPD |
| ATOM | 845 | N | ARG | 638 | 13.077 | 5.591 | -3.607 | 1.00 | 0.73 | RIPD |
| ATOM | 846 | HN | ARG | 638 | 12.494 | 4.819 | -3.768 | 1.00 | 0.72 | RIPD |
| ATOM | 847 | CA | ARG | 638 | 13.355 | 6.557 | -4.706 | 1.00 | 0.83 | RIPD |
| ATOM | 848 | HA | ARG | 638 | 14.398 | 6.838 | -4.683 | 1.00 | 0.98 | RIPD |
| ATOM | 849 | CB | ARG | 638 | 13.033 | 5.905 | -6.053 | 1.00 | 0.94 | RIPD |
| ATOM | 850 | HB1 | ARG | 638 | 11.963 | 5.879 | -6.193 | 1.00 | 1.42 | RIPD |
| ATOM | 851 | HB2 | ARG | 638 | 13.423 | 4.898 | -6.067 | 1.00 | 1.37 | RIPD |
| ATOM | 852 | CG | ARG | 638 | 13.673 | 6.718 | -7.180 | 1.00 | 1.51 | RIPD |
| ATOM | 853 | HG1 | ARG | 638 | 14.357 | 7.440 | -6.760 | 1.00 | 2.12 | RIPD |
| ATOM | 854 | HG2 | ARG | 638 | 12.901 | 7.232 | -7.736 | 1.00 | 2.12 | RIPD |
| ATOM | 855 | CD | ARG | 638 | 14.437 | 5.779 | -8.115 | 1.00 | 1.89 | RIPD |
| ATOM | 856 | HD1 | ARG | 638 | 14.629 | 4.845 | -7.608 | 1.00 | 2.27 | RIPD |
| ATOM | 857 | HD2 | ARG | 638 | 15.375 | 6.236 | -8.396 | 1.00 | 2.31 | RIPD |
| ATOM | 858 | NE | ARG | 638 | 13.624 | 5.524 | -9.337 | 1.00 | 2.49 | RIPD |
| ATOM | 859 | HE | ARG | 638 | 12.683 | 5.798 | -9.365 | 1.00 | 2.88 | RIPD |
| ATOM | 860 | CZ | ARG | 638 | 14.163 | 4.935 | -10.370 | 1.00 | 3.05 | RIPD |
| ATOM | 861 | NH1 | ARG | 638 | 14.151 | 5.522 | -11.535 | 1.00 | 3.23 | RIPD |
| ATOM | 862 | HH11 | ARG | 638 | 13.729 | 6.424 | -11.636 | 1.00 | 3.15 | RIPD |

FIG. 6A-24

| ATOM | 863 | HH12 | ARG | 638 | 14.563 | 5.071 | -12.327 | 1.00 | 3.76 | RIPD |
| ATOM | 864 | NH2 | ARG | 638 | 14.713 | 3.759 | -10.237 | 1.00 | 3.85 | RIPD |
| ATOM | 865 | HH21 | ARG | 638 | 14.722 | 3.309 | -9.344 | 1.00 | 4.13 | RIPD |
| ATOM | 866 | HH22 | ARG | 638 | 15.125 | 3.308 | -11.029 | 1.00 | 4.37 | RIPD |
| ATOM | 867 | C | ARG | 638 | 12.488 | 7.803 | -4.521 | 1.00 | 0.78 | RIPD |
| ATOM | 868 | O | ARG | 638 | 12.981 | 8.912 | -4.470 | 1.00 | 0.92 | RIPD |
| ATOM | 869 | N | GLU | 639 | 11.198 | 7.630 | -4.421 | 1.00 | 0.76 | RIPD |
| ATOM | 870 | HN | GLU | 639 | 10.820 | 6.727 | -4.465 | 1.00 | 0.79 | RIPD |
| ATOM | 871 | CA | GLU | 639 | 10.301 | 8.806 | -4.239 | 1.00 | 0.90 | RIPD |
| ATOM | 872 | HA | GLU | 639 | 10.741 | 9.669 | -4.715 | 1.00 | 1.04 | RIPD |
| ATOM | 873 | CB | GLU | 639 | 8.943 | 8.512 | -4.879 | 1.00 | 1.19 | RIPD |
| ATOM | 874 | HB1 | GLU | 639 | 8.383 | 7.841 | -4.244 | 1.00 | 1.21 | RIPD |
| ATOM | 875 | HB2 | GLU | 639 | 9.092 | 8.053 | -5.846 | 1.00 | 1.32 | RIPD |
| ATOM | 876 | CG | GLU | 639 | 8.164 | 9.818 | -5.048 | 1.00 | 1.43 | RIPD |
| ATOM | 877 | HG1 | GLU | 639 | 8.762 | 10.525 | -5.603 | 1.00 | 1.58 | RIPD |
| ATOM | 878 | HG2 | GLU | 639 | 7.932 | 10.227 | -4.075 | 1.00 | 1.56 | RIPD |
| ATOM | 879 | CD | GLU | 639 | 6.866 | 9.544 | -5.810 | 1.00 | 1.67 | RIPD |
| ATOM | 880 | OE1 | GLU | 639 | 6.431 | 8.405 | -5.810 | 1.00 | 2.21 | RIPD |
| ATOM | 881 | OE2 | GLU | 639 | 6.328 | 10.480 | -6.380 | 1.00 | 1.94 | RIPD |
| ATOM | 882 | C | GLU | 639 | 10.109 | 9.090 | -2.745 | 1.00 | 0.86 | RIPD |
| ATOM | 883 | O | GLU | 639 | 9.232 | 9.836 | -2.357 | 1.00 | 1.02 | RIPD |
| ATOM | 884 | N | GLY | 640 | 10.920 | 8.508 | -1.901 | 1.00 | 0.87 | RIPD |
| ATOM | 885 | HN | GLY | 640 | 11.625 | 7.912 | -2.227 | 1.00 | 0.91 | RIPD |
| ATOM | 886 | CA | GLY | 640 | 10.775 | 8.757 | -0.439 | 1.00 | 1.02 | RIPD |
| ATOM | 887 | HA1 | GLY | 640 | 11.200 | 7.931 | 0.111 | 1.00 | 1.17 | RIPD |
| ATOM | 888 | HA2 | GLY | 640 | 9.726 | 8.854 | -0.194 | 1.00 | 1.18 | RIPD |
| ATOM | 889 | C | GLY | 640 | 11.510 | 10.045 | -0.065 | 1.00 | 1.05 | RIPD |
| ATOM | 890 | O | GLY | 640 | 11.217 | 10.672 | 0.934 | 1.00 | 1.30 | RIPD |
| ATOM | 891 | N | ILE | 641 | 12.465 | 10.446 | -0.860 | 1.00 | 1.44 | RIPD |
| ATOM | 892 | HN | ILE | 641 | 12.687 | 9.927 | -1.661 | 1.00 | 1.79 | RIPD |
| ATOM | 893 | CA | ILE | 641 | 13.219 | 11.693 | -0.552 | 1.00 | 1.74 | RIPD |
| ATOM | 894 | HA | ILE | 641 | 13.760 | 11.566 | 0.374 | 1.00 | 1.70 | RIPD |
| ATOM | 895 | CB | ILE | 641 | 14.207 | 11.980 | -1.684 | 1.00 | 2.10 | RIPD |
| ATOM | 896 | HB | ILE | 641 | 13.666 | 12.107 | -2.611 | 1.00 | 2.41 | RIPD |
| ATOM | 897 | CG1 | ILE | 641 | 15.180 | 10.805 | -1.815 | 1.00 | 2.58 | RIPD |
| ATOM | 898 | HG11 | ILE | 641 | 14.623 | 9.884 | -1.898 | 1.00 | 2.94 | RIPD |

FIG. 6A-25

| ATOM | 899 | HG12 | ILE | 641 | 15.815 | 10.764 | -0.942 | 1.00 | 2.87 | RIPD |
| --- | --- | --- | --- | --- | --- | --- | --- | --- | --- | --- |
| ATOM | 900 | CG2 | ILE | 641 | 14.989 | 13.256 | -1.371 | 1.00 | 2.67 | RIPD |
| ATOM | 901 | HG21 | ILE | 641 | 14.314 | 14.100 | -1.362 | 1.00 | 3.14 | RIPD |
| ATOM | 902 | HG22 | ILE | 641 | 15.746 | 13.409 | -2.126 | 1.00 | 3.04 | RIPD |
| ATOM | 903 | HG23 | ILE | 641 | 15.459 | 13.162 | -0.403 | 1.00 | 2.93 | RIPD |
| ATOM | 904 | CD1 | ILE | 641 | 16.043 | 10.990 | -3.065 | 1.00 | 3.17 | RIPD |
| ATOM | 905 | HD11 | ILE | 641 | 15.997 | 10.096 | -3.669 | 1.00 | 3.72 | RIPD |
| ATOM | 906 | HD12 | ILE | 641 | 17.066 | 11.174 | -2.772 | 1.00 | 3.36 | RIPD |
| ATOM | 907 | HD13 | ILE | 641 | 15.675 | 11.829 | -3.636 | 1.00 | 3.41 | RIPD |
| ATOM | 908 | C | ILE | 641 | 12.238 | 12.861 | -0.415 | 1.00 | 2.09 | RIPD |
| ATOM | 909 | O | ILE | 641 | 12.521 | 13.848 | 0.236 | 1.00 | 2.61 | RIPD |
| ATOM | 910 | N | LYS | 642 | 11.085 | 12.755 | -1.018 | 1.00 | 2.27 | RIPD |
| ATOM | 911 | HN | LYS | 642 | 10.875 | 11.949 | -1.535 | 1.00 | 2.29 | RIPD |
| ATOM | 912 | CA | LYS | 642 | 10.087 | 13.856 | -0.915 | 1.00 | 2.89 | RIPD |
| ATOM | 913 | HA | LYS | 642 | 10.600 | 14.797 | -0.780 | 1.00 | 3.31 | RIPD |
| ATOM | 914 | CB | LYS | 642 | 9.246 | 13.910 | -2.194 | 1.00 | 3.69 | RIPD |
| ATOM | 915 | HB1 | LYS | 642 | 8.705 | 14.843 | -2.230 | 1.00 | 4.04 | RIPD |
| ATOM | 916 | HB2 | LYS | 642 | 8.547 | 13.087 | -2.199 | 1.00 | 3.75 | RIPD |
| ATOM | 917 | CG | LYS | 642 | 10.163 | 13.810 | -3.415 | 1.00 | 4.43 | RIPD |
| ATOM | 918 | HG1 | LYS | 642 | 9.947 | 12.899 | -3.953 | 1.00 | 4.52 | RIPD |
| ATOM | 919 | HG2 | LYS | 642 | 11.193 | 13.802 | -3.091 | 1.00 | 4.62 | RIPD |
| ATOM | 920 | CD | LYS | 642 | 9.925 | 15.011 | -4.333 | 1.00 | 5.32 | RIPD |
| ATOM | 921 | HD1 | LYS | 642 | 9.909 | 15.916 | -3.745 | 1.00 | 5.56 | RIPD |
| ATOM | 922 | HD2 | LYS | 642 | 8.978 | 14.893 | -4.841 | 1.00 | 5.53 | RIPD |
| ATOM | 923 | CE | LYS | 642 | 11.051 | 15.095 | -5.364 | 1.00 | 6.07 | RIPD |
| ATOM | 924 | HE1 | LYS | 642 | 10.798 | 14.493 | -6.224 | 1.00 | 6.27 | RIPD |
| ATOM | 925 | HE2 | LYS | 642 | 11.969 | 14.731 | -4.927 | 1.00 | 6.27 | RIPD |
| ATOM | 926 | NZ | LYS | 642 | 11.231 | 16.513 | -5.787 | 1.00 | 6.69 | RIPD |
| ATOM | 927 | HZ1 | LYS | 642 | 11.562 | 17.076 | -4.979 | 1.00 | 6.74 | RIPD |
| ATOM | 928 | HZ2 | LYS | 642 | 10.323 | 16.890 | -6.126 | 1.00 | 7.05 | RIPD |
| ATOM | 929 | HZ3 | LYS | 642 | 11.934 | 16.561 | -6.551 | 1.00 | 6.99 | RIPD |
| ATOM | 930 | C | LYS | 642 | 9.172 | 13.596 | 0.283 | 1.00 | 2.58 | RIPD |
| ATOM | 931 | O | LYS | 642 | 9.088 | 12.491 | 0.782 | 1.00 | 3.11 | RIPD |
| ATOM | 932 | N | GLY | 643 | 8.487 | 14.602 | 0.752 | 1.00 | 2.18 | RIPD |
| ATOM | 933 | HN | GLY | 643 | 8.567 | 15.486 | 0.337 | 1.00 | 2.30 | RIPD |
| ATOM | 934 | CA | GLY | 643 | 7.581 | 14.405 | 1.918 | 1.00 | 2.18 | RIPD |

FIG. 6A-26

| ATOM | 935 | HA1  | GLY | 643 | 7.467 | 15.339 | 2.449  | 1.00 | 2.77 | RIPD |
|------|-----|------|-----|-----|-------|--------|--------|------|------|------|
| ATOM | 936 | HA2  | GLY | 643 | 8.003 | 13.663 | 2.580  | 1.00 | 2.61 | RIPD |
| ATOM | 937 | C    | GLY | 643 | 6.211 | 13.934 | 1.427  | 1.00 | 1.46 | RIPD |
| ATOM | 938 | O    | GLY | 643 | 5.232 | 14.650 | 1.506  | 1.00 | 2.07 | RIPD |
| ATOM | 939 | N    | ALA | 644 | 6.132 | 12.734 | 0.917  | 1.00 | 0.94 | RIPD |
| ATOM | 940 | HN   | ALA | 644 | 6.934 | 12.173 | 0.861  | 1.00 | 1.46 | RIPD |
| ATOM | 941 | CA   | ALA | 644 | 4.825 | 12.222 | 0.420  | 1.00 | 1.04 | RIPD |
| ATOM | 942 | HA   | ALA | 644 | 4.057 | 12.957 | 0.605  | 1.00 | 1.55 | RIPD |
| ATOM | 943 | CB   | ALA | 644 | 4.922 | 11.955 | -1.084 | 1.00 | 1.83 | RIPD |
| ATOM | 944 | HB1  | ALA | 644 | 4.489 | 12.784 | -1.624 | 1.00 | 2.35 | RIPD |
| ATOM | 945 | HB2  | ALA | 644 | 4.385 | 11.048 | -1.324 | 1.00 | 2.39 | RIPD |
| ATOM | 946 | HB3  | ALA | 644 | 5.960 | 11.845 | -1.364 | 1.00 | 2.15 | RIPD |
| ATOM | 947 | C    | ALA | 644 | 4.472 | 10.921 | 1.145  | 1.00 | 0.81 | RIPD |
| ATOM | 948 | O    | ALA | 644 | 5.252 | 10.397 | 1.915  | 1.00 | 0.74 | RIPD |
| ATOM | 949 | N    | THR | 645 | 3.301 | 10.398 | 0.903  | 1.00 | 0.77 | RIPD |
| ATOM | 950 | HN   | THR | 645 | 2.689 | 10.838 | 0.278  | 1.00 | 0.89 | RIPD |
| ATOM | 951 | CA   | THR | 645 | 2.895 | 9.131  | 1.576  | 1.00 | 0.66 | RIPD |
| ATOM | 952 | HA   | THR | 645 | 2.890 | 9.276  | 2.646  | 1.00 | 0.66 | RIPD |
| ATOM | 953 | CB   | THR | 645 | 1.492 | 8.734  | 1.107  | 1.00 | 0.79 | RIPD |
| ATOM | 954 | HB   | THR | 645 | 1.525 | 8.459  | 0.065  | 1.00 | 1.03 | RIPD |
| ATOM | 955 | OG1  | THR | 645 | 0.609 | 9.833  | 1.281  | 1.00 | 1.02 | RIPD |
| ATOM | 956 | HG1  | THR | 645 | 0.114 | 9.947  | 0.466  | 1.00 | 1.18 | RIPD |
| ATOM | 957 | CG2  | THR | 645 | 0.995 | 7.543  | 1.928  | 1.00 | 0.82 | RIPD |
| ATOM | 958 | HG21 | THR | 645 | 0.524 | 7.900  | 2.832  | 1.00 | 1.31 | RIPD |
| ATOM | 959 | HG22 | THR | 645 | 1.830 | 6.908  | 2.183  | 1.00 | 1.40 | RIPD |
| ATOM | 960 | HG23 | THR | 645 | 0.278 | 6.980  | 1.347  | 1.00 | 1.30 | RIPD |
| ATOM | 961 | C    | THR | 645 | 3.885 | 8.022  | 1.215  | 1.00 | 0.57 | RIPD |
| ATOM | 962 | O    | THR | 645 | 4.055 | 7.067  | 1.946  | 1.00 | 0.52 | RIPD |
| ATOM | 963 | N    | VAL | 646 | 4.539 | 8.140  | 0.093  | 1.00 | 0.61 | RIPD |
| ATOM | 964 | HN   | VAL | 646 | 4.387 | 8.919  | -0.483 | 1.00 | 0.70 | RIPD |
| ATOM | 965 | CA   | VAL | 646 | 5.517 | 7.093  | -0.315 | 1.00 | 0.57 | RIPD |
| ATOM | 966 | HA   | VAL | 646 | 5.036 | 6.126  | -0.299 | 1.00 | 0.59 | RIPD |
| ATOM | 967 | CB   | VAL | 646 | 6.019 | 7.390  | -1.729 | 1.00 | 0.68 | RIPD |
| ATOM | 968 | HB   | VAL | 646 | 6.525 | 8.345  | -1.738 | 1.00 | 0.71 | RIPD |
| ATOM | 969 | CG1  | VAL | 646 | 6.992 | 6.294  | -2.167 | 1.00 | 0.69 | RIPD |
| ATOM | 970 | HG11 | VAL | 646 | 6.479 | 5.590  | -2.804 | 1.00 | 1.19 | RIPD |

FIG. 6A-27

| ATOM | 971 | HG12 | VAL | 646 | 7.373 | 5.781 | -1.296 | 1.00 | 1.07 | RIPD |
|---|---|---|---|---|---|---|---|---|---|---|
| ATOM | 972 | HG13 | VAL | 646 | 7.813 | 6.739 | -2.710 | 1.00 | 1.24 | RIPD |
| ATOM | 973 | CG2 | VAL | 646 | 4.830 | 7.430 | -2.693 | 1.00 | 0.81 | RIPD |
| ATOM | 974 | HG21 | VAL | 646 | 3.961 | 7.009 | -2.209 | 1.00 | 1.45 | RIPD |
| ATOM | 975 | HG22 | VAL | 646 | 5.063 | 6.855 | -3.576 | 1.00 | 1.26 | RIPD |
| ATOM | 976 | HG23 | VAL | 646 | 4.627 | 8.453 | -2.972 | 1.00 | 1.12 | RIPD |
| ATOM | 977 | C | VAL | 646 | 6.699 | 7.092 | 0.657 | 1.00 | 0.47 | RIPD |
| ATOM | 978 | O | VAL | 646 | 7.105 | 6.061 | 1.156 | 1.00 | 0.42 | RIPD |
| ATOM | 979 | N | GLY | 647 | 7.254 | 8.242 | 0.932 | 1.00 | 0.50 | RIPD |
| ATOM | 980 | HN | GLY | 647 | 6.910 | 9.062 | 0.520 | 1.00 | 0.57 | RIPD |
| ATOM | 981 | CA | GLY | 647 | 8.408 | 8.307 | 1.873 | 1.00 | 0.49 | RIPD |
| ATOM | 982 | HA1 | GLY | 647 | 8.668 | 9.339 | 2.054 | 1.00 | 0.57 | RIPD |
| ATOM | 983 | HA2 | GLY | 647 | 9.255 | 7.793 | 1.439 | 1.00 | 0.49 | RIPD |
| ATOM | 984 | C | GLY | 647 | 8.029 | 7.641 | 3.196 | 1.00 | 0.44 | RIPD |
| ATOM | 985 | O | GLY | 647 | 8.781 | 6.864 | 3.749 | 1.00 | 0.44 | RIPD |
| ATOM | 986 | N | LYS | 648 | 6.865 | 7.938 | 3.708 | 1.00 | 0.44 | RIPD |
| ATOM | 987 | HN | LYS | 648 | 6.272 | 8.566 | 3.246 | 1.00 | 0.47 | RIPD |
| ATOM | 988 | CA | LYS | 648 | 6.440 | 7.318 | 4.994 | 1.00 | 0.45 | RIPD |
| ATOM | 989 | HA | LYS | 648 | 7.193 | 7.498 | 5.747 | 1.00 | 0.50 | RIPD |
| ATOM | 990 | CB | LYS | 648 | 5.112 | 7.932 | 5.443 | 1.00 | 0.50 | RIPD |
| ATOM | 991 | HB1 | LYS | 648 | 4.740 | 7.396 | 6.303 | 1.00 | 0.72 | RIPD |
| ATOM | 992 | HB2 | LYS | 648 | 4.394 | 7.865 | 4.638 | 1.00 | 0.93 | RIPD |
| ATOM | 993 | CG | LYS | 648 | 5.329 | 9.400 | 5.814 | 1.00 | 1.09 | RIPD |
| ATOM | 994 | HG1 | LYS | 648 | 5.292 | 10.007 | 4.922 | 1.00 | 1.74 | RIPD |
| ATOM | 995 | HG2 | LYS | 648 | 6.294 | 9.513 | 6.287 | 1.00 | 1.51 | RIPD |
| ATOM | 996 | CD | LYS | 648 | 4.231 | 9.851 | 6.780 | 1.00 | 1.44 | RIPD |
| ATOM | 997 | HD1 | LYS | 648 | 4.278 | 9.259 | 7.681 | 1.00 | 1.56 | RIPD |
| ATOM | 998 | HD2 | LYS | 648 | 3.265 | 9.721 | 6.313 | 1.00 | 1.87 | RIPD |
| ATOM | 999 | CE | LYS | 648 | 4.434 | 11.326 | 7.131 | 1.00 | 2.15 | RIPD |
| ATOM | 1000 | HE1 | LYS | 648 | 4.233 | 11.934 | 6.261 | 1.00 | 2.60 | RIPD |
| ATOM | 1001 | HE2 | LYS | 648 | 5.453 | 11.483 | 7.452 | 1.00 | 2.37 | RIPD |
| ATOM | 1002 | NZ | LYS | 648 | 3.503 | 11.708 | 8.231 | 1.00 | 2.80 | RIPD |
| ATOM | 1003 | HZ1 | LYS | 648 | 3.903 | 12.507 | 8.762 | 1.00 | 3.04 | RIPD |
| ATOM | 1004 | HZ2 | LYS | 648 | 3.370 | 10.897 | 8.869 | 1.00 | 3.29 | RIPD |
| ATOM | 1005 | HZ3 | LYS | 648 | 2.587 | 11.988 | 7.828 | 1.00 | 3.10 | RIPD |
| ATOM | 1006 | C | LYS | 648 | 6.267 | 5.811 | 4.795 | 1.00 | 0.41 | RIPD |

FIG. 6A-28

| ATOM | 1007 | O    | LYS | 648 | 6.448  | 5.030 | 5.708  | 1.00 | 0.45 | RIPD |
|------|------|------|-----|-----|--------|-------|--------|------|------|------|
| ATOM | 1008 | N    | LEU | 649 | 5.921  | 5.396 | 3.606  | 1.00 | 0.38 | RIPD |
| ATOM | 1009 | HN   | LEU | 649 | 5.782  | 6.042 | 2.883  | 1.00 | 0.39 | RIPD |
| ATOM | 1010 | CA   | LEU | 649 | 5.741  | 3.939 | 3.350  | 1.00 | 0.40 | RIPD |
| ATOM | 1011 | HA   | LEU | 649 | 4.968  | 3.552 | 3.996  | 1.00 | 0.44 | RIPD |
| ATOM | 1012 | CB   | LEU | 649 | 5.343  | 3.722 | 1.888  | 1.00 | 0.43 | RIPD |
| ATOM | 1013 | HB1  | LEU | 649 | 6.232  | 3.647 | 1.280  | 1.00 | 0.64 | RIPD |
| ATOM | 1014 | HB2  | LEU | 649 | 4.745  | 4.556 | 1.551  | 1.00 | 0.76 | RIPD |
| ATOM | 1015 | CG   | LEU | 649 | 4.535  | 2.429 | 1.764  | 1.00 | 0.52 | RIPD |
| ATOM | 1016 | HG   | LEU | 649 | 3.671  | 2.482 | 2.411  | 1.00 | 0.89 | RIPD |
| ATOM | 1017 | CD1  | LEU | 649 | 4.076  | 2.251 | 0.317  | 1.00 | 0.52 | RIPD |
| ATOM | 1018 | HD11 | LEU | 649 | 3.000  | 2.328 | 0.269  | 1.00 | 1.23 | RIPD |
| ATOM | 1019 | HD12 | LEU | 649 | 4.384  | 1.279 | -0.041 | 1.00 | 0.98 | RIPD |
| ATOM | 1020 | HD13 | LEU | 649 | 4.520  | 3.019 | -0.299 | 1.00 | 1.11 | RIPD |
| ATOM | 1021 | CD2  | LEU | 649 | 5.407  | 1.239 | 2.169  | 1.00 | 0.91 | RIPD |
| ATOM | 1022 | HD21 | LEU | 649 | 5.130  | 0.374 | 1.585  | 1.00 | 1.54 | RIPD |
| ATOM | 1023 | HD22 | LEU | 649 | 5.263  | 1.026 | 3.218  | 1.00 | 1.52 | RIPD |
| ATOM | 1024 | HD23 | LEU | 649 | 6.446  | 1.476 | 1.989  | 1.00 | 1.24 | RIPD |
| ATOM | 1025 | C    | LEU | 649 | 7.056  | 3.212 | 3.634  | 1.00 | 0.38 | RIPD |
| ATOM | 1026 | O    | LEU | 649 | 7.068  | 2.082 | 4.080  | 1.00 | 0.42 | RIPD |
| ATOM | 1027 | N    | ALA | 650 | 8.166  | 3.852 | 3.384  | 1.00 | 0.35 | RIPD |
| ATOM | 1028 | HN   | ALA | 650 | 8.136  | 4.765 | 3.028  | 1.00 | 0.34 | RIPD |
| ATOM | 1029 | CA   | ALA | 650 | 9.480  | 3.197 | 3.644  | 1.00 | 0.38 | RIPD |
| ATOM | 1030 | HA   | ALA | 650 | 9.611  | 2.370 | 2.963  | 1.00 | 0.41 | RIPD |
| ATOM | 1031 | CB   | ALA | 650 | 10.605 | 4.212 | 3.437  | 1.00 | 0.38 | RIPD |
| ATOM | 1032 | HB1  | ALA | 650 | 10.202 | 5.212 | 3.491  | 1.00 | 1.10 | RIPD |
| ATOM | 1033 | HB2  | ALA | 650 | 11.055 | 4.057 | 2.467  | 1.00 | 1.02 | RIPD |
| ATOM | 1034 | HB3  | ALA | 650 | 11.352 | 4.083 | 4.206  | 1.00 | 1.09 | RIPD |
| ATOM | 1035 | C    | ALA | 650 | 9.513  | 2.682 | 5.085  | 1.00 | 0.44 | RIPD |
| ATOM | 1036 | O    | ALA | 650 | 9.797  | 1.526 | 5.336  | 1.00 | 0.49 | RIPD |
| ATOM | 1037 | N    | GLN | 651 | 9.213  | 3.527 | 6.033  | 1.00 | 0.46 | RIPD |
| ATOM | 1038 | HN   | GLN | 651 | 8.979  | 4.452 | 5.809  | 1.00 | 0.44 | RIPD |
| ATOM | 1039 | CA   | GLN | 651 | 9.216  | 3.081 | 7.452  | 1.00 | 0.54 | RIPD |
| ATOM | 1040 | HA   | GLN | 651 | 10.213 | 2.773 | 7.733  | 1.00 | 0.58 | RIPD |
| ATOM | 1041 | CB   | GLN | 651 | 8.760  | 4.231 | 8.353  | 1.00 | 0.60 | RIPD |
| ATOM | 1042 | HB1  | GLN | 651 | 8.799  | 3.917 | 9.386  | 1.00 | 1.00 | RIPD |

FIG. 6A-29

| ATOM | 1043 | HB2 | GLN | 651 | 7.747 | 4.507 | 8.099 | 1.00 | 1.28 | RIPD |
|------|------|------|-----|-----|--------|--------|--------|------|------|------|
| ATOM | 1044 | CG | GLN | 651 | 9.684 | 5.434 | 8.155 | 1.00 | 1.34 | RIPD |
| ATOM | 1045 | HG1 | GLN | 651 | 9.659 | 5.741 | 7.120 | 1.00 | 2.03 | RIPD |
| ATOM | 1046 | HG2 | GLN | 651 | 10.694 | 5.161 | 8.426 | 1.00 | 1.88 | RIPD |
| ATOM | 1047 | CD | GLN | 651 | 9.213 | 6.591 | 9.038 | 1.00 | 1.41 | RIPD |
| ATOM | 1048 | OE1 | GLN | 651 | 8.046 | 6.931 | 9.040 | 1.00 | 1.07 | RIPD |
| ATOM | 1049 | NE2 | GLN | 651 | 10.075 | 7.212 | 9.795 | 1.00 | 2.38 | RIPD |
| ATOM | 1050 | HE21 | GLN | 651 | 11.016 | 6.938 | 9.793 | 1.00 | 3.08 | RIPD |
| ATOM | 1051 | HE22 | GLN | 651 | 9.782 | 7.954 | 10.364 | 1.00 | 2.49 | RIPD |
| ATOM | 1052 | C | GLN | 651 | 8.256 | 1.900 | 7.602 | 1.00 | 0.57 | RIPD |
| ATOM | 1053 | O | GLN | 651 | 8.463 | 1.015 | 8.407 | 1.00 | 0.65 | RIPD |
| ATOM | 1054 | N | ALA | 652 | 7.208 | 1.878 | 6.822 | 1.00 | 0.54 | RIPD |
| ATOM | 1055 | HN | ALA | 652 | 7.064 | 2.599 | 6.174 | 1.00 | 0.49 | RIPD |
| ATOM | 1056 | CA | ALA | 652 | 6.239 | 0.751 | 6.910 | 1.00 | 0.60 | RIPD |
| ATOM | 1057 | HA | ALA | 652 | 5.955 | 0.599 | 7.940 | 1.00 | 0.68 | RIPD |
| ATOM | 1058 | CB | ALA | 652 | 4.997 | 1.078 | 6.078 | 1.00 | 0.58 | RIPD |
| ATOM | 1059 | HB1 | ALA | 652 | 5.268 | 1.745 | 5.273 | 1.00 | 1.15 | RIPD |
| ATOM | 1060 | HB2 | ALA | 652 | 4.259 | 1.553 | 6.706 | 1.00 | 1.20 | RIPD |
| ATOM | 1061 | HB3 | ALA | 652 | 4.589 | 0.166 | 5.667 | 1.00 | 1.10 | RIPD |
| ATOM | 1062 | C | ALA | 652 | 6.899 | -0.517 | 6.369 | 1.00 | 0.62 | RIPD |
| ATOM | 1063 | O | ALA | 652 | 6.710 | -1.598 | 6.890 | 1.00 | 0.72 | RIPD |
| ATOM | 1064 | N | LEU | 653 | 7.683 | -0.392 | 5.330 | 1.00 | 0.55 | RIPD |
| ATOM | 1065 | HN | LEU | 653 | 7.828 | 0.490 | 4.928 | 1.00 | 0.48 | RIPD |
| ATOM | 1066 | CA | LEU | 653 | 8.362 | -1.591 | 4.763 | 1.00 | 0.59 | RIPD |
| ATOM | 1067 | HA | LEU | 653 | 7.623 | -2.285 | 4.393 | 1.00 | 0.63 | RIPD |
| ATOM | 1068 | CB | LEU | 653 | 9.288 | -1.166 | 3.620 | 1.00 | 0.52 | RIPD |
| ATOM | 1069 | HB1 | LEU | 653 | 9.791 | -2.035 | 3.223 | 1.00 | 0.59 | RIPD |
| ATOM | 1070 | HB2 | LEU | 653 | 10.020 | -0.464 | 3.992 | 1.00 | 0.50 | RIPD |
| ATOM | 1071 | CG | LEU | 653 | 8.466 | -0.505 | 2.511 | 1.00 | 0.45 | RIPD |
| ATOM | 1072 | HG | LEU | 653 | 7.704 | 0.121 | 2.952 | 1.00 | 0.47 | RIPD |
| ATOM | 1073 | CD1 | LEU | 653 | 9.384 | 0.348 | 1.634 | 1.00 | 0.45 | RIPD |
| ATOM | 1074 | HD11 | LEU | 653 | 10.273 | 0.607 | 2.189 | 1.00 | 1.06 | RIPD |
| ATOM | 1075 | HD12 | LEU | 653 | 8.866 | 1.249 | 1.342 | 1.00 | 1.11 | RIPD |
| ATOM | 1076 | HD13 | LEU | 653 | 9.660 | -0.211 | 0.752 | 1.00 | 1.01 | RIPD |
| ATOM | 1077 | CD2 | LEU | 653 | 7.808 | -1.586 | 1.652 | 1.00 | 0.51 | RIPD |
| ATOM | 1078 | HD21 | LEU | 653 | 6.798 | -1.289 | 1.412 | 1.00 | 1.10 | RIPD |

FIG. 6A-30

| | | | | | | | | | | |
|---|---|---|---|---|---|---|---|---|---|---|
| ATOM | 1079 | HD22 | LEU | 653 | 7.790 | -2.518 | 2.196 | 1.00 | 1.19 | RIPD |
| ATOM | 1080 | HD23 | LEU | 653 | 8.372 | -1.713 | 0.739 | 1.00 | 1.06 | RIPD |
| ATOM | 1081 | C | LEU | 653 | 9.188 | -2.260 | 5.862 | 1.00 | 0.70 | RIPD |
| ATOM | 1082 | O | LEU | 653 | 9.329 | -3.465 | 5.902 | 1.00 | 0.80 | RIPD |
| ATOM | 1083 | N | HIS | 654 | 9.731 | -1.482 | 6.759 | 1.00 | 0.70 | RIPD |
| ATOM | 1084 | HN | HIS | 654 | 9.601 | -0.512 | 6.710 | 1.00 | 0.64 | RIPD |
| ATOM | 1085 | CA | HIS | 654 | 10.544 | -2.070 | 7.860 | 1.00 | 0.83 | RIPD |
| ATOM | 1086 | HA | HIS | 654 | 11.189 | -2.838 | 7.460 | 1.00 | 0.87 | RIPD |
| ATOM | 1087 | CB | HIS | 654 | 11.395 | -0.975 | 8.507 | 1.00 | 0.84 | RIPD |
| ATOM | 1088 | HB1 | HIS | 654 | 10.910 | -0.627 | 9.406 | 1.00 | 1.20 | RIPD |
| ATOM | 1089 | HB2 | HIS | 654 | 11.509 | -0.153 | 7.816 | 1.00 | 1.06 | RIPD |
| ATOM | 1090 | CG | HIS | 654 | 12.748 | -1.533 | 8.852 | 1.00 | 1.50 | RIPD |
| ATOM | 1091 | ND1 | HIS | 654 | 13.474 | -2.313 | 7.965 | 1.00 | 2.10 | RIPD |
| ATOM | 1092 | HD1 | HIS | 654 | 13.199 | -2.571 | 7.061 | 1.00 | 2.38 | RIPD |
| ATOM | 1093 | CD2 | HIS | 654 | 13.518 | -1.436 | 9.983 | 1.00 | 2.46 | RIPD |
| ATOM | 1094 | HD2 | HIS | 654 | 13.246 | -0.893 | 10.876 | 1.00 | 2.98 | RIPD |
| ATOM | 1095 | CE1 | HIS | 654 | 14.626 | -2.651 | 8.573 | 1.00 | 2.88 | RIPD |
| ATOM | 1096 | HE1 | HIS | 654 | 15.394 | -3.260 | 8.119 | 1.00 | 3.56 | RIPD |
| ATOM | 1097 | NE2 | HIS | 654 | 14.704 | -2.142 | 9.805 | 1.00 | 3.12 | RIPD |
| ATOM | 1098 | C | HIS | 654 | 9.613 | -2.680 | 8.909 | 1.00 | 0.90 | RIPD |
| ATOM | 1099 | O | HIS | 654 | 9.837 | -3.773 | 9.391 | 1.00 | 1.03 | RIPD |
| ATOM | 1100 | N | GLN | 655 | 8.568 | -1.984 | 9.266 | 1.00 | 0.86 | RIPD |
| ATOM | 1101 | HN | GLN | 655 | 8.404 | -1.105 | 8.866 | 1.00 | 0.78 | RIPD |
| ATOM | 1102 | CA | GLN | 655 | 7.625 | -2.528 | 10.283 | 1.00 | 0.96 | RIPD |
| ATOM | 1103 | HA | GLN | 655 | 8.176 | -2.835 | 11.156 | 1.00 | 1.04 | RIPD |
| ATOM | 1104 | CB | GLN | 655 | 6.614 | -1.447 | 10.671 | 1.00 | 0.92 | RIPD |
| ATOM | 1105 | HB1 | GLN | 655 | 5.762 | -1.904 | 11.149 | 1.00 | 1.19 | RIPD |
| ATOM | 1106 | HB2 | GLN | 655 | 6.291 | -0.921 | 9.784 | 1.00 | 1.31 | RIPD |
| ATOM | 1107 | CG | GLN | 655 | 7.271 | -0.461 | 11.640 | 1.00 | 1.11 | RIPD |
| ATOM | 1108 | HG1 | GLN | 655 | 8.079 | 0.051 | 11.139 | 1.00 | 1.70 | RIPD |
| ATOM | 1109 | HG2 | GLN | 655 | 7.659 | -1.000 | 12.492 | 1.00 | 1.56 | RIPD |
| ATOM | 1110 | CD | GLN | 655 | 6.236 | 0.562 | 12.109 | 1.00 | 1.24 | RIPD |
| ATOM | 1111 | OE1 | GLN | 655 | 5.244 | 0.788 | 11.445 | 1.00 | 1.28 | RIPD |
| ATOM | 1112 | NE2 | GLN | 655 | 6.425 | 1.194 | 13.235 | 1.00 | 1.99 | RIPD |
| ATOM | 1113 | HE21 | GLN | 655 | 7.225 | 1.012 | 13.771 | 1.00 | 2.44 | RIPD |
| ATOM | 1114 | HE22 | GLN | 655 | 5.768 | 1.852 | 13.544 | 1.00 | 2.29 | RIPD |

FIG. 6A-31

| ATOM | 1115 | C   | GLN | 655 | 6.889  | -3.733  | 9.699  | 1.00 | 1.04 | RIPD |
|------|------|-----|-----|-----|--------|---------|--------|------|------|------|
| ATOM | 1116 | O   | GLN | 655 | 6.732  | -4.751  | 10.343 | 1.00 | 1.18 | RIPD |
| ATOM | 1117 | N   | CYS | 656 | 6.442  | -3.626  | 8.480  | 1.00 | 0.99 | RIPD |
| ATOM | 1118 | HN  | CYS | 656 | 6.585  | -2.797  | 7.980  | 1.00 | 0.88 | RIPD |
| ATOM | 1119 | CA  | CYS | 656 | 5.721  | -4.766  | 7.846  | 1.00 | 1.13 | RIPD |
| ATOM | 1120 | HA  | CYS | 656 | 4.873  | -5.042  | 8.456  | 1.00 | 1.55 | RIPD |
| ATOM | 1121 | CB  | CYS | 656 | 5.239  | -4.353  | 6.454  | 1.00 | 1.26 | RIPD |
| ATOM | 1122 | HB1 | CYS | 656 | 5.098  | -5.233  | 5.846  | 1.00 | 1.51 | RIPD |
| ATOM | 1123 | HB2 | CYS | 656 | 5.977  | -3.713  | 5.993  | 1.00 | 1.56 | RIPD |
| ATOM | 1124 | SG  | CYS | 656 | 3.671  | -3.459  | 6.595  | 1.00 | 2.55 | RIPD |
| ATOM | 1125 | HG  | CYS | 656 | 3.286  | -3.667  | 7.449  | 1.00 | 3.00 | RIPD |
| ATOM | 1126 | C   | CYS | 656 | 6.674  | -5.957  | 7.723  | 1.00 | 1.09 | RIPD |
| ATOM | 1127 | O   | CYS | 656 | 7.773  | -5.940  | 8.242  | 1.00 | 1.46 | RIPD |
| ATOM | 1128 | N   | SER | 657 | 6.268  | -6.990  | 7.037  | 1.00 | 1.57 | RIPD |
| ATOM | 1129 | HN  | SER | 657 | 5.380  | -6.987  | 6.623  | 1.00 | 2.13 | RIPD |
| ATOM | 1130 | CA  | SER | 657 | 7.158  | -8.174  | 6.881  | 1.00 | 1.75 | RIPD |
| ATOM | 1131 | HA  | SER | 657 | 8.061  | -8.017  | 7.455  | 1.00 | 1.88 | RIPD |
| ATOM | 1132 | CB  | SER | 657 | 6.442  | -9.424  | 7.399  | 1.00 | 2.88 | RIPD |
| ATOM | 1133 | HB1 | SER | 657 | 6.883  | -10.304 | 6.946  | 1.00 | 3.28 | RIPD |
| ATOM | 1134 | HB2 | SER | 657 | 5.398  | -9.376  | 7.140  | 1.00 | 3.40 | RIPD |
| ATOM | 1135 | OG  | SER | 657 | 6.570  | -9.488  | 8.813  | 1.00 | 3.41 | RIPD |
| ATOM | 1136 | HG  | SER | 657 | 7.499  | -9.606  | 9.022  | 1.00 | 3.85 | RIPD |
| ATOM | 1137 | C   | SER | 657 | 7.527  | -8.342  | 5.399  | 1.00 | 1.33 | RIPD |
| ATOM | 1138 | O   | SER | 657 | 8.447  | -7.714  | 4.912  | 1.00 | 2.09 | RIPD |
| ATOM | 1139 | N   | ARG | 658 | 6.821  | -9.172  | 4.670  | 1.00 | 1.00 | RIPD |
| ATOM | 1140 | HN  | ARG | 658 | 6.076  | -9.669  | 5.067  | 1.00 | 1.37 | RIPD |
| ATOM | 1141 | CA  | ARG | 658 | 7.148  | -9.358  | 3.227  | 1.00 | 1.49 | RIPD |
| ATOM | 1142 | HA  | ARG | 658 | 7.567  | -8.444  | 2.832  | 1.00 | 2.03 | RIPD |
| ATOM | 1143 | CB  | ARG | 658 | 8.163  | -10.493 | 3.074  | 1.00 | 2.43 | RIPD |
| ATOM | 1144 | HB1 | ARG | 658 | 8.233  | -10.775 | 2.034  | 1.00 | 2.85 | RIPD |
| ATOM | 1145 | HB2 | ARG | 658 | 7.841  | -11.344 | 3.658  | 1.00 | 2.78 | RIPD |
| ATOM | 1146 | CG  | ARG | 658 | 9.535  | -10.028 | 3.566  | 1.00 | 3.27 | RIPD |
| ATOM | 1147 | HG1 | ARG | 658 | 9.439  | -9.599  | 4.551  | 1.00 | 3.46 | RIPD |
| ATOM | 1148 | HG2 | ARG | 658 | 9.929  | -9.287  | 2.886  | 1.00 | 3.49 | RIPD |
| ATOM | 1149 | CD  | ARG | 658 | 10.487 | -11.223 | 3.627  | 1.00 | 4.26 | RIPD |
| ATOM | 1150 | HD1 | ARG | 658 | 11.377 | -11.003 | 3.056  | 1.00 | 4.60 | RIPD |

FIG. 6A-32

| ATOM | 1151 | HD2 | ARG | 658 | 10.001 | -12.094 | 3.214 | 1.00 | 4.59 | RIPD |
|------|------|------|-----|-----|--------|---------|-------|------|------|------|
| ATOM | 1152 | NE | ARG | 658 | 10.859 | -11.484 | 5.046 | 1.00 | 4.88 | RIPD |
| ATOM | 1153 | HE | ARG | 658 | 11.388 | -10.825 | 5.541 | 1.00 | 4.95 | RIPD |
| ATOM | 1154 | CZ | ARG | 658 | 10.483 | -12.589 | 5.630 | 1.00 | 5.66 | RIPD |
| ATOM | 1155 | NH1 | ARG | 658 | 11.223 | -13.114 | 6.568 | 1.00 | 6.15 | RIPD |
| ATOM | 1156 | HH11 | ARG | 658 | 12.078 | -12.670 | 6.837 | 1.00 | 6.02 | RIPD |
| ATOM | 1157 | HH12 | ARG | 658 | 10.936 | -13.960 | 7.017 | 1.00 | 6.84 | RIPD |
| ATOM | 1158 | NH2 | ARG | 658 | 9.366 | -13.168 | 5.282 | 1.00 | 6.24 | RIPD |
| ATOM | 1159 | HH21 | ARG | 658 | 8.796 | -12.766 | 4.566 | 1.00 | 6.16 | RIPD |
| ATOM | 1160 | HH22 | ARG | 658 | 9.080 | -14.014 | 5.731 | 1.00 | 6.93 | RIPD |
| ATOM | 1161 | C | ARG | 658 | 5.876 | -9.714 | 2.456 | 1.00 | 1.16 | RIPD |
| ATOM | 1162 | O | ARG | 658 | 5.302 | -8.891 | 1.772 | 1.00 | 1.64 | RIPD |
| ATOM | 1163 | N | ILE | 659 | 5.432 | -10.938 | 2.561 | 1.00 | 1.06 | RIPD |
| ATOM | 1164 | HN | ILE | 659 | 5.910 | -11.586 | 3.119 | 1.00 | 1.49 | RIPD |
| ATOM | 1165 | CA | ILE | 659 | 4.197 | -11.349 | 1.833 | 1.00 | 1.11 | RIPD |
| ATOM | 1166 | HA | ILE | 659 | 4.350 | -11.228 | 0.771 | 1.00 | 1.29 | RIPD |
| ATOM | 1167 | CB | ILE | 659 | 3.883 | -12.815 | 2.140 | 1.00 | 1.48 | RIPD |
| ATOM | 1168 | HB | ILE | 659 | 3.653 | -12.922 | 3.190 | 1.00 | 1.70 | RIPD |
| ATOM | 1169 | CG1 | ILE | 659 | 5.093 | -13.685 | 1.788 | 1.00 | 2.03 | RIPD |
| ATOM | 1170 | HG11 | ILE | 659 | 4.861 | -14.721 | 1.984 | 1.00 | 2.35 | RIPD |
| ATOM | 1171 | HG12 | ILE | 659 | 5.939 | -13.386 | 2.389 | 1.00 | 2.45 | RIPD |
| ATOM | 1172 | CG2 | ILE | 659 | 2.679 | -13.263 | 1.308 | 1.00 | 2.03 | RIPD |
| ATOM | 1173 | HG21 | ILE | 659 | 2.559 | -14.333 | 1.395 | 1.00 | 2.53 | RIPD |
| ATOM | 1174 | HG22 | ILE | 659 | 2.840 | -13.002 | 0.273 | 1.00 | 2.26 | RIPD |
| ATOM | 1175 | HG23 | ILE | 659 | 1.788 | -12.770 | 1.669 | 1.00 | 2.51 | RIPD |
| ATOM | 1176 | CD1 | ILE | 659 | 5.432 | -13.514 | 0.306 | 1.00 | 2.76 | RIPD |
| ATOM | 1177 | HD11 | ILE | 659 | 4.528 | -13.577 | -0.280 | 1.00 | 3.00 | RIPD |
| ATOM | 1178 | HD12 | ILE | 659 | 6.114 | -14.293 | 0.001 | 1.00 | 3.28 | RIPD |
| ATOM | 1179 | HD13 | ILE | 659 | 5.895 | -12.550 | 0.152 | 1.00 | 3.22 | RIPD |
| ATOM | 1180 | C | ILE | 659 | 3.028 | -10.472 | 2.283 | 1.00 | 1.00 | RIPD |
| ATOM | 1181 | O | ILE | 659 | 2.208 | -10.058 | 1.488 | 1.00 | 1.05 | RIPD |
| ATOM | 1182 | N | ASP | 660 | 2.945 | -10.182 | 3.554 | 1.00 | 1.06 | RIPD |
| ATOM | 1183 | HN | ASP | 660 | 3.618 | -10.525 | 4.179 | 1.00 | 1.15 | RIPD |
| ATOM | 1184 | CA | ASP | 660 | 1.830 | -9.329 | 4.054 | 1.00 | 1.18 | RIPD |
| ATOM | 1185 | HA | ASP | 660 | 0.891 | -9.845 | 3.915 | 1.00 | 1.33 | RIPD |
| ATOM | 1186 | CB | ASP | 660 | 2.037 | -9.038 | 5.542 | 1.00 | 1.44 | RIPD |

FIG. 6A-33

| | | | | | | | | | |
|---|---|---|---|---|---|---|---|---|---|
| ATOM | 1187 | HB1 | ASP | 660 | 1.806 | -8.003 | 5.743 | 1.00 | 1.92 | RIPD |
| ATOM | 1188 | HB2 | ASP | 660 | 3.066 | -9.235 | 5.807 | 1.00 | 1.77 | RIPD |
| ATOM | 1189 | CG | ASP | 660 | 1.116 | -9.933 | 6.373 | 1.00 | 1.91 | RIPD |
| ATOM | 1190 | OD1 | ASP | 660 | 0.012 | -10.194 | 5.923 | 1.00 | 2.53 | RIPD |
| ATOM | 1191 | OD2 | ASP | 660 | 1.529 | -10.342 | 7.446 | 1.00 | 2.48 | RIPD |
| ATOM | 1192 | C | ASP | 660 | 1.809 | -8.012 | 3.275 | 1.00 | 0.97 | RIPD |
| ATOM | 1193 | O | ASP | 660 | 0.795 | -7.348 | 3.185 | 1.00 | 0.98 | RIPD |
| ATOM | 1194 | N | LEU | 661 | 2.922 | -7.628 | 2.710 | 1.00 | 0.87 | RIPD |
| ATOM | 1195 | HN | LEU | 661 | 3.730 | -8.177 | 2.795 | 1.00 | 0.90 | RIPD |
| ATOM | 1196 | CA | LEU | 661 | 2.965 | -6.355 | 1.939 | 1.00 | 0.82 | RIPD |
| ATOM | 1197 | HA | LEU | 661 | 2.423 | -5.590 | 2.476 | 1.00 | 0.98 | RIPD |
| ATOM | 1198 | CB | LEU | 661 | 4.420 | -5.916 | 1.759 | 1.00 | 0.85 | RIPD |
| ATOM | 1199 | HB1 | LEU | 661 | 4.826 | -6.370 | 0.868 | 1.00 | 1.04 | RIPD |
| ATOM | 1200 | HB2 | LEU | 661 | 4.998 | -6.226 | 2.618 | 1.00 | 1.27 | RIPD |
| ATOM | 1201 | CG | LEU | 661 | 4.481 | -4.394 | 1.625 | 1.00 | 1.10 | RIPD |
| ATOM | 1202 | HG | LEU | 661 | 3.725 | -4.063 | 0.927 | 1.00 | 1.75 | RIPD |
| ATOM | 1203 | CD1 | LEU | 661 | 4.228 | -3.752 | 2.990 | 1.00 | 1.58 | RIPD |
| ATOM | 1204 | HD11 | LEU | 661 | 3.477 | -2.982 | 2.893 | 1.00 | 2.05 | RIPD |
| ATOM | 1205 | HD12 | LEU | 661 | 5.145 | -3.316 | 3.358 | 1.00 | 2.10 | RIPD |
| ATOM | 1206 | HD13 | LEU | 661 | 3.884 | -4.505 | 3.684 | 1.00 | 1.88 | RIPD |
| ATOM | 1207 | CD2 | LEU | 661 | 5.864 | -3.982 | 1.118 | 1.00 | 1.44 | RIPD |
| ATOM | 1208 | HD21 | LEU | 661 | 5.868 | -2.923 | 0.904 | 1.00 | 2.11 | RIPD |
| ATOM | 1209 | HD22 | LEU | 661 | 6.097 | -4.532 | 0.219 | 1.00 | 1.82 | RIPD |
| ATOM | 1210 | HD23 | LEU | 661 | 6.604 | -4.198 | 1.875 | 1.00 | 1.71 | RIPD |
| ATOM | 1211 | C | LEU | 661 | 2.324 | -6.566 | 0.565 | 1.00 | 0.64 | RIPD |
| ATOM | 1212 | O | LEU | 661 | 1.426 | -5.849 | 0.172 | 1.00 | 0.69 | RIPD |
| ATOM | 1213 | N | LEU | 662 | 2.778 | -7.542 | -0.172 | 1.00 | 0.54 | RIPD |
| ATOM | 1214 | HN | LEU | 662 | 3.505 | -8.110 | 0.160 | 1.00 | 0.59 | RIPD |
| ATOM | 1215 | CA | LEU | 662 | 2.193 | -7.792 | -1.521 | 1.00 | 0.51 | RIPD |
| ATOM | 1216 | HA | LEU | 662 | 2.411 | -6.954 | -2.166 | 1.00 | 0.56 | RIPD |
| ATOM | 1217 | CB | LEU | 662 | 2.800 | -9.064 | -2.116 | 1.00 | 0.65 | RIPD |
| ATOM | 1218 | HB1 | LEU | 662 | 2.316 | -9.289 | -3.054 | 1.00 | 1.15 | RIPD |
| ATOM | 1219 | HB2 | LEU | 662 | 2.657 | -9.886 | -1.430 | 1.00 | 1.00 | RIPD |
| ATOM | 1220 | CG | LEU | 662 | 4.296 | -8.852 | -2.355 | 1.00 | 1.14 | RIPD |
| ATOM | 1221 | HG | LEU | 662 | 4.760 | -8.500 | -1.445 | 1.00 | 1.80 | RIPD |
| ATOM | 1222 | CD1 | LEU | 662 | 4.939 | -10.175 | -2.774 | 1.00 | 1.53 | RIPD |

FIG. 6A-34

| ATOM | 1223 | HD11 | LEU | 662 | 4.994 | -10.222 | -3.852 | 1.00 | 1.86 | RIPD |
|---|---|---|---|---|---|---|---|---|---|---|
| ATOM | 1224 | HD12 | LEU | 662 | 4.342 | -10.997 | -2.408 | 1.00 | 1.98 | RIPD |
| ATOM | 1225 | HD13 | LEU | 662 | 5.934 | -10.240 | -2.359 | 1.00 | 2.09 | RIPD |
| ATOM | 1226 | CD2 | LEU | 662 | 4.494 | -7.818 | -3.465 | 1.00 | 1.78 | RIPD |
| ATOM | 1227 | HD21 | LEU | 662 | 4.611 | -6.837 | -3.027 | 1.00 | 2.34 | RIPD |
| ATOM | 1228 | HD22 | LEU | 662 | 3.633 | -7.820 | -4.118 | 1.00 | 2.16 | RIPD |
| ATOM | 1229 | HD23 | LEU | 662 | 5.378 | -8.066 | -4.034 | 1.00 | 2.21 | RIPD |
| ATOM | 1230 | C | LEU | 662 | 0.676 | -7.960 | -1.403 | 1.00 | 0.52 | RIPD |
| ATOM | 1231 | O | LEU | 662 | -0.083 | -7.363 | -2.141 | 1.00 | 0.53 | RIPD |
| ATOM | 1232 | N | SER | 663 | 0.225 | -8.768 | -0.483 | 1.00 | 0.64 | RIPD |
| ATOM | 1233 | HN | SER | 663 | 0.851 | -9.242 | 0.104 | 1.00 | 0.70 | RIPD |
| ATOM | 1234 | CA | SER | 663 | -1.243 | -8.969 | -0.326 | 1.00 | 0.79 | RIPD |
| ATOM | 1235 | HA | SER | 663 | -1.638 | -9.439 | -1.214 | 1.00 | 0.80 | RIPD |
| ATOM | 1236 | CB | SER | 663 | -1.512 | -9.861 | 0.886 | 1.00 | 1.03 | RIPD |
| ATOM | 1237 | HB1 | SER | 663 | -2.286 | -10.576 | 0.639 | 1.00 | 1.40 | RIPD |
| ATOM | 1238 | HB2 | SER | 663 | -1.838 | -9.256 | 1.716 | 1.00 | 1.52 | RIPD |
| ATOM | 1239 | OG | SER | 663 | -0.317 | -10.542 | 1.243 | 1.00 | 1.75 | RIPD |
| ATOM | 1240 | HG | SER | 663 | -0.438 | -10.914 | 2.120 | 1.00 | 2.06 | RIPD |
| ATOM | 1241 | C | SER | 663 | -1.922 | -7.613 | -0.123 | 1.00 | 0.81 | RIPD |
| ATOM | 1242 | O | SER | 663 | -2.873 | -7.276 | -0.800 | 1.00 | 0.86 | RIPD |
| ATOM | 1243 | N | SER | 664 | -1.439 | -6.831 | 0.803 | 1.00 | 0.86 | RIPD |
| ATOM | 1244 | HN | SER | 664 | -0.669 | -7.119 | 1.337 | 1.00 | 0.85 | RIPD |
| ATOM | 1245 | CA | SER | 664 | -2.057 | -5.498 | 1.046 | 1.00 | 1.03 | RIPD |
| ATOM | 1246 | HA | SER | 664 | -3.081 | -5.629 | 1.362 | 1.00 | 1.17 | RIPD |
| ATOM | 1247 | CB | SER | 664 | -1.280 | -4.761 | 2.138 | 1.00 | 1.19 | RIPD |
| ATOM | 1248 | HB1 | SER | 664 | -1.313 | -5.336 | 3.053 | 1.00 | 1.63 | RIPD |
| ATOM | 1249 | HB2 | SER | 664 | -1.724 | -3.795 | 2.308 | 1.00 | 1.58 | RIPD |
| ATOM | 1250 | OG | SER | 664 | 0.067 | -4.587 | 1.721 | 1.00 | 1.72 | RIPD |
| ATOM | 1251 | HG | SER | 664 | 0.541 | -5.402 | 1.903 | 1.00 | 2.04 | RIPD |
| ATOM | 1252 | C | SER | 664 | -2.024 | -4.678 | -0.244 | 1.00 | 0.93 | RIPD |
| ATOM | 1253 | O | SER | 664 | -2.979 | -4.013 | -0.585 | 1.00 | 1.07 | RIPD |
| ATOM | 1254 | N | LEU | 665 | -0.933 | -4.719 | -0.965 | 1.00 | 0.77 | RIPD |
| ATOM | 1255 | HN | LEU | 665 | -0.173 | -5.264 | -0.670 | 1.00 | 0.68 | RIPD |
| ATOM | 1256 | CA | LEU | 665 | -0.837 | -3.935 | -2.236 | 1.00 | 0.81 | RIPD |
| ATOM | 1257 | HA | LEU | 665 | -0.745 | -2.885 | -2.002 | 1.00 | 0.99 | RIPD |

FIG. 6A-35

| | | | | | | | | | |
|---|---|---|---|---|---|---|---|---|---|
| ATOM | 1258 | CB | LEU | 665 | 0.392 | -4.388 | -3.025 | 1.00 | 0.78 | RIPD |
| ATOM | 1259 | HB1 | LEU | 665 | 0.356 | -3.966 | -4.019 | 1.00 | 0.92 | RIPD |
| ATOM | 1260 | HB2 | LEU | 665 | 0.400 | -5.466 | -3.092 | 1.00 | 0.66 | RIPD |
| ATOM | 1261 | CG | LEU | 665 | 1.658 | -3.911 | -2.317 | 1.00 | 0.88 | RIPD |
| ATOM | 1262 | HG | LEU | 665 | 1.643 | -4.240 | -1.289 | 1.00 | 0.80 | RIPD |
| ATOM | 1263 | CD1 | LEU | 665 | 2.885 | -4.495 | -3.020 | 1.00 | 0.97 | RIPD |
| ATOM | 1264 | HD11 | LEU | 665 | 3.489 | -5.032 | -2.304 | 1.00 | 1.38 | RIPD |
| ATOM | 1265 | HD12 | LEU | 665 | 3.467 | -3.695 | -3.453 | 1.00 | 1.32 | RIPD |
| ATOM | 1266 | HD13 | LEU | 665 | 2.565 | -5.170 | -3.800 | 1.00 | 1.58 | RIPD |
| ATOM | 1267 | CD2 | LEU | 665 | 1.721 | -2.382 | -2.367 | 1.00 | 1.16 | RIPD |
| ATOM | 1268 | HD21 | LEU | 665 | 1.056 | -2.020 | -3.136 | 1.00 | 1.54 | RIPD |
| ATOM | 1269 | HD22 | LEU | 665 | 2.731 | -2.070 | -2.587 | 1.00 | 1.56 | RIPD |
| ATOM | 1270 | HD23 | LEU | 665 | 1.420 | -1.979 | -1.411 | 1.00 | 1.61 | RIPD |
| ATOM | 1271 | C | LEU | 665 | -2.092 | -4.158 | -3.086 | 1.00 | 0.78 | RIPD |
| ATOM | 1272 | O | LEU | 665 | -2.669 | -3.228 | -3.613 | 1.00 | 0.92 | RIPD |
| ATOM | 1273 | N | ILE | 666 | -2.520 | -5.382 | -3.219 | 1.00 | 0.69 | RIPD |
| ATOM | 1274 | HN | ILE | 666 | -2.044 | -6.119 | -2.782 | 1.00 | 0.63 | RIPD |
| ATOM | 1275 | CA | ILE | 666 | -3.740 | -5.660 | -4.027 | 1.00 | 0.80 | RIPD |
| ATOM | 1276 | HA | ILE | 666 | -4.263 | -4.732 | -4.211 | 1.00 | 0.94 | RIPD |
| ATOM | 1277 | CB | ILE | 666 | -3.332 | -6.288 | -5.369 | 1.00 | 1.04 | RIPD |
| ATOM | 1278 | HB | ILE | 666 | -2.586 | -5.663 | -5.839 | 1.00 | 1.53 | RIPD |
| ATOM | 1279 | CG1 | ILE | 666 | -4.556 | -6.394 | -6.288 | 1.00 | 1.80 | RIPD |
| ATOM | 1280 | HG11 | ILE | 666 | -5.274 | -7.076 | -5.859 | 1.00 | 2.43 | RIPD |
| ATOM | 1281 | HG12 | ILE | 666 | -4.246 | -6.763 | -7.255 | 1.00 | 2.35 | RIPD |
| ATOM | 1282 | CG2 | ILE | 666 | -2.743 | -7.682 | -5.137 | 1.00 | 1.45 | RIPD |
| ATOM | 1283 | HG21 | ILE | 666 | -3.478 | -8.430 | -5.392 | 1.00 | 1.71 | RIPD |
| ATOM | 1284 | HG22 | ILE | 666 | -2.466 | -7.788 | -4.099 | 1.00 | 2.02 | RIPD |
| ATOM | 1285 | HG23 | ILE | 666 | -1.869 | -7.811 | -5.758 | 1.00 | 2.05 | RIPD |
| ATOM | 1286 | CD1 | ILE | 666 | -5.201 | -5.016 | -6.453 | 1.00 | 1.86 | RIPD |
| ATOM | 1287 | HD11 | ILE | 666 | -6.124 | -4.982 | -5.894 | 1.00 | 2.30 | RIPD |
| ATOM | 1288 | HD12 | ILE | 666 | -5.407 | -4.837 | -7.499 | 1.00 | 1.98 | RIPD |
| ATOM | 1289 | HD13 | ILE | 666 | -4.528 | -4.257 | -6.084 | 1.00 | 2.26 | RIPD |
| ATOM | 1290 | C | ILE | 666 | -4.654 | -6.607 | -3.244 | 1.00 | 0.72 | RIPD |
| ATOM | 1291 | O | ILE | 666 | -5.143 | -7.592 | -3.760 | 1.00 | 0.83 | RIPD |
| ATOM | 1292 | N | TYR | 667 | -4.884 | -6.311 | -1.993 | 1.00 | 0.73 | RIPD |
| ATOM | 1293 | HN | TYR | 667 | -4.475 | -5.512 | -1.599 | 1.00 | 0.82 | RIPD |

FIG. 6A-36

| ATOM | 1294 | CA   | TYR | 667 | -5.760  | -7.181 | -1.161 | 1.00 | 0.83 | RIPD |
|------|------|------|-----|-----|---------|--------|--------|------|------|------|
| ATOM | 1295 | HA   | TYR | 667 | -5.531  | -8.217 | -1.362 | 1.00 | 0.91 | RIPD |
| ATOM | 1296 | CB   | TYR | 667 | -5.491  | -6.876 | 0.328  | 1.00 | 1.15 | RIPD |
| ATOM | 1297 | HB1  | TYR | 667 | -5.450  | -5.805 | 0.465  | 1.00 | 1.41 | RIPD |
| ATOM | 1298 | HB2  | TYR | 667 | -4.540  | -7.302 | 0.608  | 1.00 | 1.42 | RIPD |
| ATOM | 1299 | CG   | TYR | 667 | -6.573  | -7.452 | 1.228  | 1.00 | 1.45 | RIPD |
| ATOM | 1300 | CD1  | TYR | 667 | -7.304  | -8.586 | 0.841  | 1.00 | 1.87 | RIPD |
| ATOM | 1301 | HD1  | TYR | 667 | -7.101  | -9.062 | -0.107 | 1.00 | 2.17 | RIPD |
| ATOM | 1302 | CD2  | TYR | 667 | -6.841  | -6.840 | 2.459  | 1.00 | 2.02 | RIPD |
| ATOM | 1303 | HD2  | TYR | 667 | -6.279  | -5.968 | 2.761  | 1.00 | 2.30 | RIPD |
| ATOM | 1304 | CE1  | TYR | 667 | -8.298  | -9.100 | 1.684  | 1.00 | 2.39 | RIPD |
| ATOM | 1305 | HE1  | TYR | 667 | -8.863  | -9.969 | 1.385  | 1.00 | 2.86 | RIPD |
| ATOM | 1306 | CE2  | TYR | 667 | -7.833  | -7.356 | 3.300  | 1.00 | 2.63 | RIPD |
| ATOM | 1307 | HE2  | TYR | 667 | -8.038  | -6.881 | 4.249  | 1.00 | 3.28 | RIPD |
| ATOM | 1308 | CZ   | TYR | 667 | -8.562  | -8.485 | 2.912  | 1.00 | 2.67 | RIPD |
| ATOM | 1309 | OH   | TYR | 667 | -9.541  | -8.992 | 3.741  | 1.00 | 3.36 | RIPD |
| ATOM | 1310 | HH   | TYR | 667 | -10.220 | -9.387 | 3.190  | 1.00 | 3.58 | RIPD |
| ATOM | 1311 | C    | TYR | 667 | -7.227  | -6.906 | -1.511 | 1.00 | 0.92 | RIPD |
| ATOM | 1312 | O    | TYR | 667 | -7.713  | -5.801 | -1.377 | 1.00 | 1.27 | RIPD |
| ATOM | 1313 | N    | VAL | 668 | -7.936  | -7.912 | -1.946 | 1.00 | 1.25 | RIPD |
| ATOM | 1314 | HN   | VAL | 668 | -7.525  | -8.797 | -2.036 | 1.00 | 1.63 | RIPD |
| ATOM | 1315 | CA   | VAL | 668 | -9.372  | -7.722 | -2.288 | 1.00 | 1.47 | RIPD |
| ATOM | 1316 | HA   | VAL | 668 | -9.587  | -6.667 | -2.379 | 1.00 | 1.54 | RIPD |
| ATOM | 1317 | CB   | VAL | 668 | -9.687  | -8.427 | -3.609 | 1.00 | 1.99 | RIPD |
| ATOM | 1318 | HB   | VAL | 668 | -9.483  | -9.483 | -3.511 | 1.00 | 2.41 | RIPD |
| ATOM | 1319 | CG1  | VAL | 668 | -11.163 | -8.223 | -3.959 | 1.00 | 2.57 | RIPD |
| ATOM | 1320 | HG11 | VAL | 668 | -11.708 | -9.136 | -3.765 | 1.00 | 2.90 | RIPD |
| ATOM | 1321 | HG12 | VAL | 668 | -11.253 | -7.965 | -5.004 | 1.00 | 3.10 | RIPD |
| ATOM | 1322 | HG13 | VAL | 668 | -11.569 | -7.426 | -3.354 | 1.00 | 2.89 | RIPD |
| ATOM | 1323 | CG2  | VAL | 668 | -8.815  | -7.838 | -4.720 | 1.00 | 2.49 | RIPD |
| ATOM | 1324 | HG21 | VAL | 668 | -9.147  | -8.215 | -5.676 | 1.00 | 2.83 | RIPD |
| ATOM | 1325 | HG22 | VAL | 668 | -7.786  | -8.121 | -4.559 | 1.00 | 2.91 | RIPD |
| ATOM | 1326 | HG23 | VAL | 668 | -8.898  | -6.761 | -4.710 | 1.00 | 2.84 | RIPD |
| ATOM | 1327 | C    | VAL | 668 | -10.223 | -8.325 | -1.171 | 1.00 | 1.64 | RIPD |
| ATOM | 1328 | O    | VAL | 668 | -10.544 | -9.497 | -1.185 | 1.00 | 2.04 | RIPD |
| ATOM | 1329 | N    | SER | 669 | -10.580 | -7.537 | -0.196 | 1.00 | 1.73 | RIPD |

FIG. 6A-37

| ATOM | 1330 | HN | SER | 669 | -10.302 | -6.597 | -0.200 | 1.00 | 1.75 | RIPD |
|---|---|---|---|---|---|---|---|---|---|---|
| ATOM | 1331 | CA | SER | 669 | -11.396 | -8.066 | 0.931 | 1.00 | 2.19 | RIPD |
| ATOM | 1332 | HA | SER | 669 | -10.852 | -8.860 | 1.421 | 1.00 | 2.56 | RIPD |
| ATOM | 1333 | CB | SER | 669 | -11.660 | -6.946 | 1.935 | 1.00 | 2.55 | RIPD |
| ATOM | 1334 | HB1 | SER | 669 | -11.822 | -6.019 | 1.402 | 1.00 | 2.88 | RIPD |
| ATOM | 1335 | HB2 | SER | 669 | -10.808 | -6.838 | 2.586 | 1.00 | 2.98 | RIPD |
| ATOM | 1336 | OG | SER | 669 | -12.805 | -7.268 | 2.713 | 1.00 | 2.75 | RIPD |
| ATOM | 1337 | HG | SER | 669 | -12.635 | -8.101 | 3.160 | 1.00 | 3.07 | RIPD |
| ATOM | 1338 | C | SER | 669 | -12.727 | -8.617 | 0.407 | 1.00 | 2.37 | RIPD |
| ATOM | 1339 | O | SER | 669 | -13.406 | -9.357 | 1.090 | 1.00 | 3.01 | RIPD |
| ATOM | 1340 | N | GLN | 670 | -13.107 | -8.273 | -0.796 | 1.00 | 2.37 | RIPD |
| ATOM | 1341 | HN | GLN | 670 | -12.549 | -7.678 | -1.337 | 1.00 | 2.47 | RIPD |
| ATOM | 1342 | CA | GLN | 670 | -14.390 | -8.796 | -1.345 | 1.00 | 2.83 | RIPD |
| ATOM | 1343 | HA | GLN | 670 | -15.197 | -8.557 | -0.668 | 1.00 | 3.07 | RIPD |
| ATOM | 1344 | CB | GLN | 670 | -14.663 | -8.163 | -2.712 | 1.00 | 3.02 | RIPD |
| ATOM | 1345 | HB1 | GLN | 670 | -13.981 | -8.571 | -3.442 | 1.00 | 3.33 | RIPD |
| ATOM | 1346 | HB2 | GLN | 670 | -14.523 | -7.093 | -2.646 | 1.00 | 3.42 | RIPD |
| ATOM | 1347 | CG | GLN | 670 | -16.101 | -8.466 | -3.137 | 1.00 | 3.18 | RIPD |
| ATOM | 1348 | HG1 | GLN | 670 | -16.589 | -7.550 | -3.434 | 1.00 | 3.30 | RIPD |
| ATOM | 1349 | HG2 | GLN | 670 | -16.636 | -8.906 | -2.307 | 1.00 | 3.31 | RIPD |
| ATOM | 1350 | CD | GLN | 670 | -16.093 | -9.442 | -4.315 | 1.00 | 3.92 | RIPD |
| ATOM | 1351 | OE1 | GLN | 670 | -15.210 | -9.399 | -5.148 | 1.00 | 4.19 | RIPD |
| ATOM | 1352 | NE2 | GLN | 670 | -17.047 | -10.327 | -4.420 | 1.00 | 4.64 | RIPD |
| ATOM | 1353 | HE21 | GLN | 670 | -17.760 | -10.362 | -3.749 | 1.00 | 4.80 | RIPD |
| ATOM | 1354 | HE22 | GLN | 670 | -17.050 | -10.957 | -5.171 | 1.00 | 5.21 | RIPD |
| ATOM | 1355 | C | GLN | 670 | -14.285 | -10.315 | -1.498 | 1.00 | 3.60 | RIPD |
| ATOM | 1356 | O | GLN | 670 | -14.026 | -10.824 | -2.572 | 1.00 | 4.11 | RIPD |
| ATOM | 1357 | N | ASN | 671 | -14.474 | -11.043 | -0.431 | 1.00 | 4.21 | RIPD |
| ATOM | 1358 | HN | ASN | 671 | -14.676 | -10.611 | 0.425 | 1.00 | 4.21 | RIPD |
| ATOM | 1359 | CA | ASN | 671 | -14.376 | -12.526 | -0.511 | 1.00 | 5.33 | RIPD |
| ATOM | 1360 | HA | ASN | 671 | -13.370 | -12.803 | -0.788 | 1.00 | 5.73 | RIPD |
| ATOM | 1361 | CB | ASN | 671 | -14.711 | -13.131 | 0.853 | 1.00 | 6.14 | RIPD |
| ATOM | 1362 | HB1 | ASN | 671 | -15.226 | -14.069 | 0.715 | 1.00 | 6.75 | RIPD |
| ATOM | 1363 | HB2 | ASN | 671 | -15.343 | -12.449 | 1.404 | 1.00 | 6.27 | RIPD |
| ATOM | 1364 | CG | ASN | 671 | -13.416 | -13.373 | 1.630 | 1.00 | 6.39 | RIPD |
| ATOM | 1365 | OD1 | ASN | 671 | -12.430 | -13.810 | 1.071 | 1.00 | 6.30 | RIPD |

FIG. 6A-38

| ATOM | 1366 | ND2 | ASN | 671 | -13.375 | -13.103 | 2.906 | 1.00 | 7.06 | RIPD |
|------|------|------|-----|-----|---------|---------|--------|------|------|------|
| ATOM | 1367 | HD21 | ASN | 671 | -14.168 | -12.750 | 3.358 | 1.00 | 7.36 | RIPD |
| ATOM | 1368 | HD22 | ASN | 671 | -12.548 | -13.252 | 3.412 | 1.00 | 7.43 | RIPD |
| ATOM | 1369 | C | ASN | 671 | -15.354 | -13.052 | -1.564 | 1.00 | 5.64 | RIPD |
| ATOM | 1370 | O | ASN | 671 | -14.992 | -13.277 | -2.701 | 1.00 | 6.08 | RIPD |
| ATOM | 1371 | N | HIS | 672 | -16.590 | -13.250 | -1.198 | 1.00 | 5.80 | RIPD |
| ATOM | 1372 | HN | HIS | 672 | -16.866 | -13.064 | -0.276 | 1.00 | 5.66 | RIPD |
| ATOM | 1373 | CA | HIS | 672 | -17.583 | -13.761 | -2.186 | 1.00 | 6.56 | RIPD |
| ATOM | 1374 | HA | HIS | 672 | -17.189 | -13.639 | -3.184 | 1.00 | 6.86 | RIPD |
| ATOM | 1375 | CB | HIS | 672 | -17.855 | -15.243 | -1.922 | 1.00 | 6.88 | RIPD |
| ATOM | 1376 | HB1 | HIS | 672 | -18.914 | -15.391 | -1.767 | 1.00 | 7.25 | RIPD |
| ATOM | 1377 | HB2 | HIS | 672 | -17.314 | -15.558 | -1.042 | 1.00 | 7.00 | RIPD |
| ATOM | 1378 | CG | HIS | 672 | -17.406 | -16.056 | -3.105 | 1.00 | 7.00 | RIPD |
| ATOM | 1379 | ND1 | HIS | 672 | -18.259 | -16.365 | -4.152 | 1.00 | 7.19 | RIPD |
| ATOM | 1380 | HD1 | HIS | 672 | -19.199 | -16.099 | -4.231 | 1.00 | 7.27 | RIPD |
| ATOM | 1381 | CD2 | HIS | 672 | -16.200 | -16.630 | -3.422 | 1.00 | 7.33 | RIPD |
| ATOM | 1382 | HD2 | HIS | 672 | -15.308 | -16.580 | -2.815 | 1.00 | 7.53 | RIPD |
| ATOM | 1383 | CE1 | HIS | 672 | -17.561 | -17.095 | -5.042 | 1.00 | 7.59 | RIPD |
| ATOM | 1384 | HE1 | HIS | 672 | -17.971 | -17.480 | -5.963 | 1.00 | 8.00 | RIPD |
| ATOM | 1385 | NE2 | HIS | 672 | -16.301 | -17.286 | -4.645 | 1.00 | 7.68 | RIPD |
| ATOM | 1386 | C | HIS | 672 | -18.888 | -12.974 | -2.055 | 1.00 | 7.09 | RIPD |
| ATOM | 1387 | OT1 | HIS | 672 | -19.241 | -12.632 | -0.939 | 1.00 | 7.54 | RIPD |
| ATOM | 1388 | OT2 | HIS | 672 | -19.514 | -12.731 | -3.074 | 1.00 | 7.31 | RIPD |

SEQUENCE LISTING

```
<160> NUMBER OF SEQ ID NOS: 3

<210> SEQ ID NO 1
<211> LENGTH: 100
<212> TYPE: PRT
<213> ORGANISM: Homo sapiens
<220> FEATURE:
<221> NAME/KEY: MISC_FEATURE
<223> OTHER INFORMATION: RIP DD

<400> SEQUENCE: 1

Met Ala Ile Phe Asp Asn Thr Thr Ser Leu Thr Asp Lys His Leu Asp
1               5                  10                  15

Pro Ile Arg Glu Asn Leu Gly Lys His Trp Lys Asn Cys Ala Arg Lys
            20                  25                  30

Leu Gly Phe Thr Gln Ser Gln Ile Asp Glu Ile Asp His Asp Tyr Glu
        35                  40                  45

Arg Asp Gly Leu Lys Glu Lys Val Tyr Gln Met Leu Gln Lys Trp Val
    50                  55                  60

Met Arg Glu Gly Ile Lys Gly Ala Thr Val Gly Lys Leu Ala Gln Ala
65                  70                  75                  80

Leu His Gln Cys Ser Arg Ile Asp Leu Leu Ser Ser Leu Ile Tyr Val
                85                  90                  95

Ser Gln Asn His
            100

<210> SEQ ID NO 2
<211> LENGTH: 104
<212> TYPE: PRT
<213> ORGANISM: Homo sapiens
<220> FEATURE:
<221> NAME/KEY: MISC_FEATURE
<223> OTHER INFORMATION: FAS DD

<400> SEQUENCE: 2

Met Glu Thr Val Ala Ile Asn Leu Ser Asp Val Asp Leu Ser Lys Tyr
1               5                  10                  15

Ile Thr Thr Ile Ala Gly Val Met Thr Leu Ser Gln Val Lys Gly Phe
            20                  25                  30
```

-continued

```
Val Arg Lys Asn Gly Val Asn Glu Ala Lys Ile Asp Glu Ile Lys Asn
        35              40              45

Asp Asn Val Gln Asp Thr Ala Glu Gln Lys Val Gln Leu Leu Arg Asn
        50              55              60

Trp His Gln Leu His Gly Lys Lys Glu Ala Tyr Asp Thr Leu Ile Lys
65              70              75              80

Asp Leu Lys Lys Ala Asn Leu Cys Thr Leu Ala Glu Lys Ile Gln Thr
            85              90              95

Ile Ile Leu Lys Asp Ile Thr Ser
            100

<210> SEQ ID NO 3
<211> LENGTH: 99
<212> TYPE: PRT
<213> ORGANISM: Homo sapiens
<220> FEATURE:
<221> NAME/KEY: MISC_FEATURE
<223> OTHER INFORMATION: RIP DD

<400> SEQUENCE: 3

Met Ala Ile Phe Asp Asn Thr Thr Ser Leu Thr Asp Lys His Leu Asp
1               5               10              15

Pro Ile Arg Glu Asn Leu Gly Lys His Trp Lys Asn Cys Ala Arg Lys
            20              25              30

Leu Gly Phe Thr Gln Ser Gln Ile Asp Glu Ile Asp His Asp Tyr Glu
        35              40              45

Arg Asp Gly Leu Lys Glu Lys Val Tyr Gln Met Leu Gln Lys Trp Val
        50              55              60

Met Arg Glu Gly Ile Lys Gly Ala Thr Val Gly Lys Leu Ala Gln Ala
65              70              75              80

Leu His Gln Cys Ser Arg Ile Asp Leu Leu Ser Ser Leu Ile Tyr Val
            85              90              95

Ser Gln Asn
```

SOLUTION STRUCTURE OF RIP DD AND USES THEREOF

CROSS REFERENCE TO RELATED APPLICATIONS

This application claims the benefit of U.S. Provisional Application No. 60/356,391, filed Feb. 11, 2002.

FIELD OF THE INVENTION

The present invention relates to the three dimensional solution structure of receptor interacting protein death domain (RIP DD), as well as the identification of various active site structures of RIP DD. These structures are critical for the design and selection of potent and selective inhibitors of TNF signaling pathways.

BACKGROUND OF THE INVENTION

Activation of the Tumor Necrosis Factor Receptor-1 (TNFR-1) by the ligand TNF initiates two major intracellular signaling pathways that lead to the activation of the transcription factor NFκB (Tartaglia & Goeddel, 1992) and the induction of cell death (Grell et al., 1993; Tartaglia et al., 1993). Interaction of a TNF trimer with a TNFR-1 trimer induces intracellular self-association of the TNFR-1 death domain (DD) (Smith et al., 1994) (Chan et al., 2000) allowing for the recruitment of an adaptor protein named TNFR-Associated Death Domain protein (TRADD) through a death domain/death domain interaction. TRADD (Hsu et al., 1995) recruits the signaling molecule TNFR-Associated Factor-2 (TRAF-2) (Hsu et al., 1996b) through interactions with the N-terminal domain. On the other hand, Fas Associated Death Domain protein (FADD) (Hsu et al., 1996b) and the Receptor Interacting Protein (RIP) (Hsu et al., 1996a) are recruited to the TNFR-1 signaling complex through death domain interactions with TRADD.

RIP is required for activation of the transcription factor NFκB by TNF (Kelliher et al., 1998) and is a structurally unique protein containing both a kinase domain and a death domain (Stanger et al., 1995). Overall, the protein contains 671 residues and three domains consisting of a 300 residue N-terminal serine/threonine kinase domain, a 272 residue intermediate region, and a 99 residue death domain. Deletion mutagenesis studies have shown that the N-terminal region of RIP is involved in binding to TRAF-2 and that the intermediate region of RIP is the critical domain for activation of the transcription factor NFκB (Hsu et al., 1996a). The deletion mutagenesis studies also showed that RIP DD binds to TRADD DD allowing for the recruitment of RIP to the TNFR-1 signaling complex. Importantly, it has been shown that RIP DD can block TNF-mediated NFκB and JNK activation, probably by competing with endogenous RIP for interaction with the TNFR-1/TRADD complex (Hsu et al., 1996a). RIP was also found to interact with RAIDD, which is another adaptor molecule in the ICH-1 pathway, through a death domain/death domain interaction (Duan & Dixit, 1997).

Structural studies, especially by NMR, on death domain proteins at physiological pH have been complicated by the tendency of the proteins to self-associate and form large molecular weight aggregates. This is also the case for the Death Effector Domains (DED) and the Caspase Recruiting Domains (CARD) which are structurally related to the death domains. Therefore, structural studies of the death domain superfamily of proteins requires relatively low ($\leq 4$) or high ($\geq 8$) pH to minimize the natural tendency of self aggregation. This was the case for FAS DD (Huang et al., 1996), FADD DED (Eberstadt et al., 1998), FADD DD (Jeong et al., 1999), RAIDD CARD (Chou et al., 1998), TNFR-1 DD (Telliez et al., 2000), and in the current study of the RIP DD. In addition, single point mutants which alter protein solubility were necessary for the structural studies of the FADD DED (Chou et al., 1998) and TNFR-1 DD (Telliez et al., 2000). To date, the structures of several death domains have been solved: FAS DD (Huang et al., 1996), p75 neurotrophin DD (Liepinsh et al., 1997), FADD DD (Jeong et al., 1999), a complex structure of the Tube DD with the Pelle DD (xiao et al., 1999) and TNFR-1 DD (Sukits, et al., 2001). In addition, one death effector domain structure (FADD DED) (Eberstadt et al., 1998), and three CARD domain structures: RAIDD CARD (Chou et al., 1998), APAF-1 (Zhou et al., 1999) (Qin et al., 1999), and the complex between APAF-1 and procaspase-9 (Zhou et al., 1999) have been solved. All the structures have the same general fold consisting of a core of six α-helices arranged in an anti-parallel fashion, where the lengths and orientations of the helices are slightly different in the various structures.

SUMMARY OF THE INVENTION

The present invention relates to the three dimensional structure of a receptor interacting protein death domain (RIP DD), and more specifically, to the solution structure of RIP DD, as determined using spectroscopy and various computer modeling techniques.

Particularly, the invention is further directed to the identification, characterization and three dimensional structure of an active site of RIP DD that provides an attractive target for the rational design of potent and selective inhibitors of TNF signaling pathways.

Accordingly, the present invention provides a solution comprising a receptor interacting protein death domain (RIP DD). The three dimensional solution structure of RIP DD is provided by the relative atomic structural coordinates of FIG. 6, as obtained from spectroscopy data.

Also provided by the present invention is an active site of a TRADD DD binding protein or peptide, preferably of RIP DD, wherein said active site is characterized by a three dimensional structure comprising the relative structural coordinates of amino acid residues D613, H617, D618, R621, K625, E626 and K627 according to FIG. 6, ± a root mean square deviation from the conserved backbone atoms of said amino acids of not more than 1.5 Å.

Also provided for by the present invention is an active site of a TRADD DD binding protein or peptide, preferably of RIP DD, wherein said active site is characterized by a three dimensional structure comprising the relative structural coordinates of amino acid residues K599 and R603 according to FIG. 6, ± a root mean square deviation from the conserved backbone atoms of said amino acids of not more than 1.5 Å.

The solution coordinates of RIP DD or portions thereof (such as the TRADD DD binding site or other active sites), as provided by this invention may be stored in a machine-readable form on a machine-readable storage medium, e.g. a computer hard drive, diskette, DAT tape, etc., for display as a three-dimensional shape or for other uses involving computer-assisted manipulation of, or computation based on, the structural coordinates or the three-dimensional structures they define. By way of example, the data defining the three dimensional structure of RIP DD as set forth in FIG. 6 may be stored in a machine-readable storage medium, and may be displayed as a graphical three-dimensional representation of the relevant structural coordinates, typically using a computer capable of reading the data from said storage medium and programmed with instructions for creating the representation from such data.

Accordingly, the present invention provides a machine, such as a computer, programmed in memory with the coordinates of RIP DD or portions thereof, together with a program capable of converting the coordinates into a three dimensional graphical representation of the structural coordinates on a display connected to the machine. A machine having a memory containing such data aids in the rational design or selection of inhibitors of RIP DD binding or activity, including the evaluation of the ability of a particular chemical entity to favorably associate with RIP DD as disclosed herein, as well as in the modeling of compounds, proteins, complexes, etc. related by structural or sequence homology to RIP DD.

The present invention is additionally directed to a method of determining the three dimensional structure of a molecule or molecular complex whose structure is unknown, comprising the steps of first obtaining crystals or a solution of the molecule or molecular complex whose structure is unknown, and then generating X-ray diffraction data from the crystallized molecule or molecular complex and/or generating NMR data from the solution of the molecule or molecular complex. The generated diffraction or spectroscopy data from the molecule or molecular complex can then be compared with the solution coordinates or three dimensional structure of RIP DD as disclosed herein, and the three dimensional structure of the unknown molecule or molecular complex conformed to the RIP DD structure using standard techniques such as molecular replacement analysis, 2D, 3D and 4D isotope filtering, editing and triple resonance NMR techniques, and computer homology modeling. Alternatively, a three dimensional model of the unknown molecule may be generated by generating a sequence alignment between RIP DD and the unknown molecule, based on any or all of amino acid sequence identity, secondary structure elements or tertiary folds, and then generating by computer modeling a three dimensional structure for the molecule using the three dimensional structure of, and sequence alignment with, RIP DD.

The present invention further provides a method for identifying an agent that interacts with RIP DD, comprising the steps of determining an active site of RIP DD using the three dimensional RIP DD structure, and then performing computer fitting analyses to identify an agent which interacts with the identified active site. Once the agent has been identified, it may be contacted with RIP DD (using RIP DD or a molecule comprising RIP DD such as RIP), and the effect the agent has on RIP DD may then be assessed. In addition, the agent may be contacted with RIP DD (using RIP DD or a molecule comprising RIP DD such as RIP) in the presence of a TRADD DD binding molecule (including but not limited to TRADD DD), and the effect the agent has on binding between RIP DD and the TRADD DD binding molecule may then be assessed.

Also provided is a method for identifying a potential inhibitor of RIP DD, comprising the steps of using a three dimensional structure of RIP DD as defined by the relative structural coordinates of amino acids encoding RIP DD to design or select a potential inhibitor, and obtaining or synthesizing said potential inhibitor. The inhibitor may be selected by screening an appropriate database, may designed de novo by analyzing the steric configurations and charge potentials of an empty RIP DD active site in conjunction with the appropriate software programs, or may be designed using characteristics of known inhibitors to create "hybrid" inhibitors. The inhibitor may then be contacted with RIP DD alone (using RIP DD or a molecule comprising RIP DD such as RIP), or in the presence of a RIP DD binding molecule such as TRADD DD, and the effect of the inhibitor on RIP DD alone or binding between RIP DD and the RIP DD binding molecule may be assessed. It is also within the confines of the present invention that a potential inhibitor may be designed or selected by identifying chemical entities or fragments capable of associating with RIP DD; and assembling the identified chemical entities or fragments into a single molecule to provide the structure of the potential inhibitor.

Finally, the present invention provides agents or inhibitors designed or selected using the methods disclosed herein. Additional objects of the present invention will be apparent from the description which follows.

BRIEF DESCRIPTION OF THE FIGURES

FIG. 6 lists the atomic structure coordinates for the restrained minimized mean structure of RIP DD as derived by multidimensional NMR spectroscopy. "Atom type" refers to the atom whose coordinates are being measured. "Residue" refers to the type of residue of which each measured atom is a part—i.e., amino acid, cofactor, ligand or solvent. The "x, y and z" coordinates indicate the Cartesian coordinates of each measured atom's location (Å). All non-protein atoms are listed as HETATM instead of atoms using PDB conventions.

DETAILED DESCRIPTION OF THE INVENTION

Figure 1:
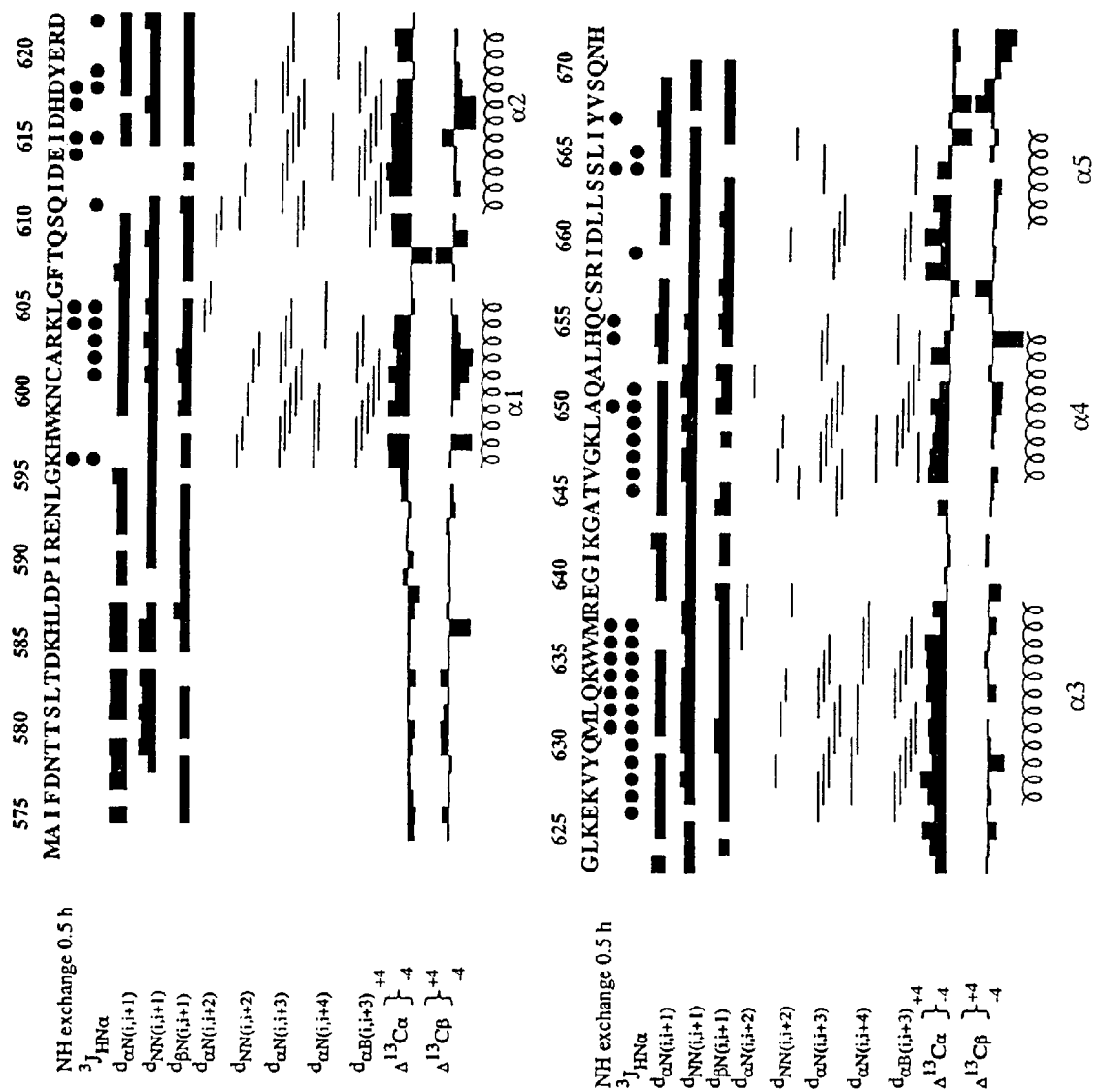
FIG. 1. Summary of H-D exchange, $^3J_{HNH\alpha}$ scalar coupling information, sequential NOEs ($d_{\alpha N}$, $d_{NN}$, $d_{\beta N}$), medium range NOEs ($d_{\alpha N(i,i+2)}$, $d_{NN(i,i+2)}$, $d_{\alpha N(i,i+3)}$, $d_{\alpha N(i,i+4)}$, $d_{\alpha\beta(i,i+3)}$), and the $\Delta^{13}C_\alpha$ and $\Delta^{13}C_\beta$ chemical shift index. Residues that didn't exhibit NH exchange with $D_2O$ within 30 minutes are designated with an (●). The residues having a $^3J_{HNH\alpha}$ less than 5 Hz are designated with an (●). The intensities of the NOEs are represented by the thickness of the lines. The values of the $\Delta^{13}C_\alpha$ and $\Delta^{13}C_\beta$ are represented by the intensity of the blocks. The secondary structure is indicated at the bottom. Top row: amino acid sequence of RIP death domain (SEQ ID NO:1).

As used herein, the following terms and phrases shall have the meanings set forth below:

Unless otherwise noted, "RIP DD" includes both the death domain of RIP as encoded by the amino acid sequence of FIG. 1 (SEQ ID NO:1) (including conservative substitutions thereof), as well as "RIP DD analogues", defined herein as proteins or peptides comprising a TRADD DD or TRADD DD-like binding site and include an active site characterized by a three dimensional structure comprising (i) the relative structural coordinates of amino acid residues D613, H617, D618, R621, K625, E626 and K627 according to FIG. 6, or (ii) the relative structural coordinates of amino acid residues K599 and R603 according to FIG. 6, in each case, ± a root mean square deviation from the conserved backbone atoms of said amino acids of not more than 1.5 Å, more preferably not more than 1.0 Å, and most preferably not more than 0.5 Å.

Unless otherwise indicated, "protein" or "molecule" shall include a protein, protein domain, polypeptide or peptide.

"Structural coordinates" are the Cartesian coordinates corresponding to an atom's spatial relationship to other atoms in a molecule or molecular complex. Structural coordinates may be obtained using x-ray crystallography techniques or NMR techniques, or may be derived using molecular replacement analysis or homology modeling. Various software programs allow for the graphical representation of a set of structural coordinates to obtain a three dimensional representation of a molecule or molecular complex. The structural coordinates of the present invention may be modified from the original set provided in FIG. 6 by mathematical manipulation, such as by inversion or integer additions or subtractions. As such, it is recognized that the structural coordinates of the present invention are relative, and are in no way specifically limited by the actual x, y, z coordinates of FIG. 6.

An "agent" shall include a protein, polypeptide, peptide, nucleic acid, including DNA or RNA, molecule, compound or drug.

"Root mean square deviation" is the square root of the arithmetic mean of the squares of the deviations from the mean, and is a way of expressing deviation or variation from the structural coordinates described herein. The present invention includes all embodiments comprising conservative substitutions of the noted amino acid residues resulting in same structural coordinates within the stated root mean square deviation.

It will be obvious to the skilled practitioner that the numbering of the amino acid residues in the various isoforms of RIP DD covered by the present invention may be different than that set forth herein, or may contain certain conservative amino acid substitutions that yield the same three dimensional or solution structures as those defined by FIG. 6 herein. Corresponding amino acids and conservative substitutions in other isoforms or analogues are easily identified by visual inspection of the relevant amino acid sequences or by using commercially available homology software programs.

"Conservative substitutions" are those amino acid substitutions which are functionally equivalent to the substituted amino acid residue, either by way of having similar polarity, steric arrangement, or by belonging to the same class as the substituted residue (e.g., hydrophobic, acidic or basic), and includes substitutions having an inconsequential effect on the three dimensional structure of RIP DD with respect to the use of said structure for the identification and design of RIP DD or RIP DD complex inhibitors, for molecular replacement analyses and/or for homology modeling.

An "active site" refers to a region of a molecule or molecular complex that, as a result of its shape and charge potential, favorably interacts or associates with another agent (including, without limitation, a protein, polypeptide, peptide, nucleic acid, including DNA or RNA, molecule, compound, antibiotic or drug) via various covalent and/or non-covalent binding forces. As such, an active site of the present invention may include, for example, the actual site of TRADD DD binding with RIP DD, as well as accessory binding sites adjacent to the actual site of TRADD DD binding that nonetheless may affect RIP DD upon interaction or association with a particular agent, either by direct interference with the actual site of TRADD DD binding or by indirectly affecting the steric conformation or charge potential of RIP DD and thereby preventing or reducing TRADD DD binding to RIP DD at the actual site of TRADD DD binding. As used herein, "active site" also includes the RIP DD site of self association, as well as other binding sites present on RIP DD.

A "RIP DD complex" refers to a co-complex of a molecule comprising the RIP DD region in bound association with a protein, polypeptide, peptide, nucleic acid, including DNA or RNA, small molecule, compound or drug, either by covalent or non-covalent binding forces. A non-limiting example of a RIP DD complex includes RIP, RIP DD or a RIP DD analogue bound to TRADD DD.

The present invention relates to the three dimensional structure of RIP DD or of a RIP DD analogue, and more specifically, to the solution structure of RIP DD as determined using multidimensional NMR spectroscopy and various computer modeling techniques. The solution coordinates of RIP DD (disclosed herein at FIG. 6) are useful for a number of applications, including, but not limited to, the characterization of a three dimensional structure of RIP DD, as well as the visualization, identification and characterization of RIP DD active sites, including the site of TRADD DD binding to RIP DD. The active site structures may then be used to predict the orientation and binding affinity of a designed or selected inhibitor of RIP DD, a RIP DD analogue or of a RIP DD complex. Accordingly, the invention is particularly directed to the three dimensional structure of a RIP DD active site, including but not limited to the TRADD DD binding site.

As used herein, the RIP DD in solution comprises amino acid residues 588-671 of RIP, and more preferably, the amino acid residues 588-671 set forth in FIG. 1, or conservative substitutions thereof. Preferably, the RIP DD in solution is either unlabeled, $^{15}N$ enriched or $^{15}N,^{13}C$ enriched, and is preferably biologically active. In addition, the secondary structure of the RIP DD in the solutions of the present invention comprises five alpha (α) helices. In this regard, α1 comprises amino acid residues K596-L605 of RIP DD, α2 comprises amino acid residues Q609-D622 of RIP DD, α3 comprises amino acid residues V628-E639 of RIP DD, α4 comprises amino acid residues T645-Q655 of RIP DD and α5 comprises amino acid residues I659-L665 of RIP DD.

The protein or peptide used in the solution of the present invention includes RIP DD, as well as RIP DD analogues, where said protein or peptide preferably comprises an active site characterized by a three dimensional structure comprising (i) the relative structural coordinates of amino acid residues D613, H617, D618, R621, K625, E626 and K627 according to FIG. 6, or (ii) the relative structural coordinates of amino acid residues K599 and R603 according to FIG. 6, in each case, ± a root mean square deviation from the conserved backbone atoms of said amino acids of not more than 1.5 Å, more preferably not more than 1.0 Å, and most preferably not more than 0.5 Å. In the most preferred embodiment, the protein or peptide used in the solution of the present invention is characterized by a three dimensional structure comprising the complete structural coordinates of the amino acids according to FIG. 8, ± a root mean square deviation from the conserved backbone atoms of said amino acids of not more than 1.5 Å (or more preferably, not more than 1.0 Å, and most preferably, not more than 0.5 Å).

Molecular modeling methods known in the art may be used to identify an active site or binding pocket of RIP DD, a RIP DD complex, or of a RIP DD analogue. Specifically, the solution structural coordinates provided by the present invention may be used to characterize a three dimensional structure of the RIP DD molecule, molecular complex or RIP DD analogue. From such a structure, putative active sites may be computationally visualized, identified and characterized based on the surface structure of the molecule, surface charge, steric arrangement, the presence of reactive amino acids, regions of hydrophobicity or hydrophilicity, etc. Such putative active sites may be further refined using chemical shift perturbations of spectra generated from various and distinct RIP DD complexes, competitive and non-competitive inhibition experiments, and/or by the generation and characterization of RIP DD or ligand mutants to identify critical residues or characteristics of the active site.

The identification of putative active sites of a molecule or molecular complex is of great importance, as most often the biological activity of a molecule or molecular complex results from the interaction between an agent and one or more active sites of the molecule or molecular complex. Accordingly, the active sites of a molecule or molecular complex are the best targets to use in the design or selection of inhibitors that affect the activity of the molecule or molecular complex.

The present invention is directed to an active site of RIP DD, a RIP DD complex or of a RIP DD analogue, that, as a result of its shape, reactivity, charge potential, etc., favorably interacts or associates with another agent (including, without limitation, a protein, polypeptide, peptide, nucleic acid, including DNA or RNA, molecule, compound, antibiotic or drug). Preferably, the present invention is directed to an active site of a TRADD DD binding protein or peptide, and preferably RIP DD, that is characterized by the three dimensional structure comprising the relative structural coordinates of amino acid residues D613, H617, D618, R621, K625, E626 and K627 according to FIG. 6, ± a root mean square deviation from the conserved backbone atoms of said amino acids of not more than 1.5 Å, preferably not more than 1.0 Å, and most preferably not more than 0.5 Å.

In another embodiment, the active site of a TRADD DD binding protein or peptide, and preferably RIP DD, is characterized by the three dimensional structure comprising the relative structural coordinates of amino acid residues K599 and R603 according to FIG. 6, ± a root mean square deviation from the conserved backbone atoms of said amino acids of not more than 1.5 Å, preferably not more than 1.0 Å, and most preferably not more than 0.5 Å.

In order to use the structural coordinates generated for a solution structure of the present invention as set forth in FIG. 6, it is often necessary to display the relevant coordinates as, or convert them to, a three dimensional shape or graphical representation, or to otherwise manipulate them. For example, a three dimensional representation of the structural coordinates is often used in rational drug design, molecular replacement analysis, homology modeling, and mutation analysis. This is typically accomplished using any of a wide variety of commercially available software programs capable of generating three dimensional graphical representations of molecules or portions thereof from a set of structural coordinates. Examples of said commercially available software programs include, without limitation, the following: GRID (Oxford University, Oxford, UK); MCSS (Molecular Simulations, San Diego, Calif.); AUTODOCK (Scripps Research Institute, La Jolla, Calif.); DOCK (University of California, San Francisco, Calif.); Flo99 (Thistlesoft, Morris Township, N.J.); Ludi (Molecular Simulations, San Diego, Calif.); QUANTA (Molecular Simulations, San Diego, Calif.); Insight (Molecular Simulations, San Diego, Calif.); SYBYL (TRIPOS, Inc., St. Louis. Mo.); and LEAP-FROG (TRIPOS, Inc., St. Louis, Mo.).

For storage, transfer and use with such programs, a machine, such as a computer, is provided for that produces a three dimensional representation of the RIP DD, a portion thereof (such as an active site or a binding site), a RIP DD molecular complex, or a RIP DD analogue. The machine of the present invention comprises a machine-readable data storage medium comprising a data storage material encoded with machine-readable data. Machine-readable storage media comprising data storage material include conventional computer hard drives, floppy disks, DAT tape, CD-ROM, and other magnetic, magneto-optical, optical, floptical and other media which may be adapted for use with a computer. The machine of the present invention also comprises a working memory for storing instructions for processing the machine-readable data, as well as a central processing unit (CPU) coupled to the working memory and to the machine-readable data storage medium for the purpose of processing the machine-readable data into the desired three dimensional representation. Finally, the machine of the present invention further comprises a display connected to the CPU so that the three dimensional representation may be visualized by the user. Accordingly, when used with a machine programmed with instructions for using said data, e.g., a computer loaded with one or more programs of the sort identified above, the machine provided for herein is capable of displaying a graphical three-dimensional representation of any of the molecules or molecular complexes, or portions of molecules of molecular complexes, described herein.

In one embodiment of the invention, the machine-readable data comprises the relative structural coordinates of amino acid residues D613, H617, D618, R621, K625, E626 and K627 according to FIG. 6, ± a root mean square deviation from the conserved backbone atoms of said amino acids of not more than 1.5 Å, or preferably, not more than 1.0 Å, or more preferably not more than 0.5 Å. In an alternate embodiment, the machine-readable data further comprises the relative structural coordinates of amino acid residues K599 and R603 according to FIG. 6, ± a root mean square deviation from the conserved backbone atoms of said amino acids of not more than 1.5 Å, preferably not more than 1.0 Å, and most preferably not more than 0.5 Å.

The structural coordinates of the present invention permit the use of various molecular design and analysis techniques in order to (i) solve the three dimensional structures of related molecules, molecular complexes or RIP DD analogues, and (ii) to design, select, and synthesize chemical agents capable of favorably associating or interacting with an active site of an RIP DD molecule, molecular complex or RIP DD analogue, wherein, said chemical agents potentially act as inhibitors of RIP DD or RIP DD complex binding to a number of binding proteins, including, but not limited to, TRADD DD.

More specifically, the present invention provides a method for determining the molecular structure of a molecule or molecular complex whose structure is unknown, comprising the steps of obtaining a solution of the molecule or molecular complex whose structure is unknown, and then generating NMR data from the solution of the molecule or molecular complex. The NMR data from the molecule or molecular complex whose structure is unknown is then compared to the solution structure data obtained from the RIP DD solutions of the present invention. Then, 2D, 3D and 4D isotope filtering, editing and triple resonance NMR techniques are used to conform the three dimensional structure determined from the RIP DD solution of the present invention to the NMR data from the solution molecule or molecular complex. Alternatively, molecular replacement may be used to conform the RIP DD solution structure of the present invention to x-ray diffraction data from crystals of the unknown molecule or molecular complex.

Molecular replacement uses a molecule having a known structure as a starting point to model the structure of an unknown crystalline sample. This technique is based on the principle that two molecules which have similar structures, orientations and positions will diffract x-rays similarly. A corresponding approach to molecular replacement is applicable to modeling an unknown solution structure using NMR technology. The NMR spectra and resulting analysis of the NMR data for two similar structures will be essentially identical for regions of the proteins that are structurally conserved, where the NMR analysis consists of obtaining the NMR resonance assignments and the structural constraint assignments, which may contain hydrogen bond, distance, dihedral angle, coupling constant, chemical shift and dipolar coupling constant constraints. The observed differences in the NMR spectra of the two structures will highlight the differences between the two structures and identify the corresponding differences in the structural constraints. The structure determination process for the unknown structure is then based on modifying the NMR constraints from the known structure to be consistent with the observed spectral differences between the NMR spectra.

Accordingly, in one non-limiting embodiment of the invention, the resonance assignments for the RIP DD solution provide the starting point for resonance assignments of RIP DD in a new RIP DD: "unsolved agent" complex. Chemical shift perturbances in two dimensional $^{15}$N/$^{1}$H spectra can be observed and compared between the RIP DD solution and the new RIP DD:agent complex. In this way, the affected residues may be correlated with the three dimensional structure of RIP DD as provided by the relevant structural coordinates of FIG. 6. This effectively identifies the region of the RIP DD:agent complex that has incurred a structural change relative to the native RIP DD structure. The $^{1}$H, $^{15}$N, $^{13}$C and $^{13}$CO NMR resonance assignments corresponding to both the sequential backbone and side-chain amino acid assignments of RIP DD may then be obtained and the three dimensional structure of the new RIP DD:agent complex may be generated using standard 2D, 3D and 4D triple resonance NMR techniques and NMR assignment methodology, using the RIP DD solution structure, resonance assignments and structural constraints as a reference. Various computer fitting analyses of the new agent with the three dimensional model of RIP DD may be performed in order to generate an initial three dimensional model of the new agent complexed with RIP DD, and the resulting three dimensional model may be refined using standard experimental constraints and energy minimization techniques in order to position and orient the new agent in association with the three dimensional structure of RIP DD.

The present invention further provides that the structural coordinates of the present invention may be used with standard homology modeling techniques in order to determine the unknown three-dimensional structure of a molecule or molecular complex. Homology modeling involves constructing a model of an unknown structure using structural coordinates of one or more related protein molecules, molecular complexes or parts thereof (i.e., active sites). Homology modeling may be conducted by fitting common or homologous portions of the protein whose three dimensional structure is to be solved to the three dimensional structure of homologous structural elements in the known molecule, specifically using the relevant (i.e., homologous) structural coordinates provided by FIG. 6 herein. Homology may be determined using amino acid sequence identity, homologous secondary structure elements, and/or homologous tertiary folds. Homology modeling can include rebuilding part or all of a three dimensional structure with replacement of amino acids (or other components) by those of the related structure to be solved.

Accordingly, a three dimensional structure for the unknown molecule or molecular complex may be generated using the three dimensional structure of the RIP DD molecule of the present invention, refined using a number of techniques well known in the art, and then used in the same fashion as the structural coordinates of the present invention, for instance, in applications involving molecular replacement analysis, homology modeling, and rational drug design.

Determination of the three dimensional structure of RIP DD, its TRADD DD binding active site, and other binding sites, is critical to the rational identification and/or design of agents that may act as inhibitors of RIP DD, such as inhibitors of TRADD DD binding to RIP DD. This is advantageous over conventional drug assay techniques, in which the only way to identify such an agent is to screen thousands of test compounds until an agent having the desired inhibitory effect on a target compound is identified. Necessarily, such conventional screening methods are expensive, time consuming, and do not elucidate the method of action of the identified agent on the target compound.

However, advancing X-ray, spectroscopic and computer modeling technologies allow researchers to visualize the three dimensional structure of a targeted compound (i.e., of RIP DD). Using such a three dimensional structure, researchers identify putative binding sites and then identify or design agents to interact with these binding sites. These agents are then screened for an inhibitory effect upon the target molecule. In this manner, not only are the number of agents to be screened for the desired activity greatly reduced, but the mechanism of action on the target compound is better understood.

Accordingly, the present invention further provides a method for identifying a potential inhibitor of RIP DD, a RIP DD analogue or of a RIP DD complex, comprising the steps of using a three dimensional structure of RIP DD as defined by the relative structural coordinates of FIG. 6 to design or select a potential inhibitor of RIP DD activity, and synthesizing or obtaining said potential inhibitor. The inhibitor may be selected by screening an appropriate database, may be designed de novo by analyzing the steric configurations and charge potentials of an empty RIP DD or RIP DD complex active site in conjunction with the appropriate software programs, or may be designed using characteristics of known inhibitors of protein binding to RIP DD or RIP DD complexes in order to create "hybrid" inhibitors.

An agent that interacts or associates with an active site of RIP DD, a RIP DD complex or a RIP DD analogue may be identified by determining an active site from the three dimensional structure of RIP DD, and performing computer fitting analyses to identify an agent which interacts or associates with said active site. Computer fitting analyses utilize various computer software programs that evaluate the "fit" between the putative active site and the identified agent, by (a) generating a three dimensional model of the putative active site of a molecule or molecular complex using homology modeling or the atomic structural coordinates of the active site, and (b) determining the degree of association between the putative active site and the identified agent. The degree of association may be determined computationally by any number of commercially available software programs, or may be determined experimentally using standard binding assays.

Three dimensional models of the putative active site may be generated using any one of a number of methods known in the art, and include, but are not limited to, homology modeling as well as computer analysis of raw structural coordinate data generated using crystallographic or spectroscopy techniques. Computer programs used to generate such three dimensional models and/or perform the necessary fitting analyses include, but are not limited to: GRID (Oxford University, Oxford, UK), MCSS (Molecular Simulations, San Diego, Calif.), AUTODOCK (Scripps Research Institute, La Jolla, Calif.), DOCK (University of California, San Francisco, Calif.), Flo99 (Thistlesoft, Morris Township, N.J.), Ludi (Molecular Simulations, San Diego, Calif.), QUANTA (Molecular Simulations, San Diego, Calif.), Insight (Molecular Simulations, San Diego, Calif.), SYBYL (TRIPOS, Inc., St. Louis. Mo.) and LEAPFROG (TRIPOS, Inc., St. Louis, Mo.).

In a preferred method of the present invention, the active site preferably comprises amino acid residues D613, H617, D618, R621, K625, E626 and K627 (or conservative substitutions thereof) according to FIG. 6, or amino acid residues K599 and R603 (or conservative substitutions thereof) according to FIG. 6.

In the more preferred embodiment, the method of the present invention includes the use of an active site characterized by the three dimensional structure comprising the relative structural coordinates of amino acid residues D613, H617, D618, R621, K625, E626 and K627 according to FIG. 6, ± a root mean square deviation from the conserved backbone atoms of said amino acids of not more than 1.5 Å, preferably not more than 1.0 Å, and most preferably not more than 0.5 Å. In another embodiment, the active site is characterized by the three dimensional structure comprising the relative structural coordinates of amino acid residues K599 and R603 according to FIG. 6, ± a root mean square deviation from the conserved backbone atoms of said amino acids of not more than 1.5 Å, preferably not more than 1.0 Å, and most preferably not more than 0.5 Å. It is understood that the method of the present invention includes additional embodiments comprising conservative substitutions of the noted amino acids which result in the same structural coordinates of the corresponding residues in FIG. 6 within the stated root mean square deviation.

The effect of such an agent identified by computer fitting analyses on RIP DD, RIP DD complex or RIP DD analogue activity may be further evaluated computationally, or experimentally by competitive binding experiments or by contacting the identified agent with RIP DD (or a RIP DD complex or analogue or a molecule comprising RIP DD such as RIP) and measuring the effect of the agent on the target's biological activity. Standard enzymatic assays may be performed and the results analyzed to determine whether the agent is an inhibitor of RIP DD activity (i.e., the agent may reduce or prevent binding affinity between RIP DD and a relevant binding protein, such as TRADD DD. Further tests may be performed to evaluate the selectivity of the identified agent to RIP DD with regard to other RIP DD analogues or TRADD DD binding targets.

An agent designed or selected to interact with RIP DD preferably is capable of both physically and structurally associating with RIP DD via various covalent and/or non-covalent molecular interactions, and of assuming a three dimensional configuration and orientation that complements the relevant active site of RIP DD.

Accordingly, using these criteria, the structural coordinates of the RIP DD molecule as disclosed herein, and/or structural coordinates derived therefrom using molecular replacement or homology modeling, agents may be designed to increase either or both of the potency and selectivity of known inhibitors, either by modifying the structure of known inhibitors or by designing new agents de novo via computational inspection of the three dimensional configuration and electrostatic potential of a RIP DD active site.

Accordingly, in one embodiment of the invention, the structural coordinates of FIG. 6 of the present invention, or structural coordinates derived therefrom using molecular replacement or homology modeling techniques as discussed above, are used to screen a database for agents that may act as potential inhibitors of RIP DD activity. Specifically, the obtained structural coordinates of the present invention are read into a software package and the three dimensional structure is analyzed graphically. A number of computational software packages may be used for the analysis of structural coordinates, including, but not limited to, Sybyl (Tripos Associates), QUANTA and XPLOR (Brunger, A. T., (1994) *X-Plor* 3.851: *a system for X-ray Crystallography and NMR. Xplor Version* 3.851 New Haven, Conn.: Yale University Press). Additional software programs check for the correctness of the coordinates with regard to features such as bond and atom types. If necessary, the three dimensional structure is modified and then energy minimized using the appropriate software until all of the structural parameters are at their equilibrium/optimal values. The energy minimized structure is superimposed against the original structure to make sure there are no significant deviations between the original and the energy minimized coordinates.

The energy minimized coordinates of RIP DD bound to a "solved" inhibitor are then analyzed and the interactions between the solved ligand and RIP DD are identified. The final RIP DD structure is modified by graphically removing the solved inhibitor so that only RIP DD and a few residues of the solved agent are left for analysis of the binding site cavity. QSAR and SAR analysis and/or conformational analysis may be carried out to determine how other inhibitors compare to the solved inhibitor. The solved agent may be docked into the uncomplexed structure's binding site to be used as a template for data base searching, using software to create excluded volume and distance restrained queries for the searches. Structures qualifying as hits are then screened for activity using standard assays and other methods known in the art.

Further, once the specific interaction is determined between the solved inhibitor, docking studies with different inhibitors allow for the generation of initial models of new inhibitors bound to RIP DD. The integrity of these new models may be evaluated a number of ways, including constrained conformational analysis using molecular dynamics methods (i.e., where both RIP DD and the bound inhibitor are allowed to sample different three dimensional conformational states until the most favorable state is reached or found to exist between the protein and the bound agent). The final structure as proposed by the molecular dynamics analysis is analyzed visually to make sure that the model is in accord with known experimental SAR based on measured binding affinities. Once models are obtained of the original solved agent bound to RIP DD and computer models of other molecules bound to RIP DD, strategies are determined for designing modifications into the inhibitors to improve their activity and/or enhance their selectivity.

Once a RIP DD binding agent has been optimally selected or designed, as described above, substitutions may then be made in some of its atoms or side groups in order to improve or modify its selectivity and binding properties. Generally, initial substitutions are conservative, i.e., the replacement group will have approximately the same size, shape, hydrophobicity and charge as the original group. Such substituted chemical compounds may then be analyzed for efficiency of fit RIP DD by the same computer methods described in detail above.

Various molecular analysis and rational drug design techniques are further disclosed in U.S. Pat. Nos. 5,834,228, 5,939,528 and 5,865,116, as well as in PCT Application No. PCT/US98/16879, published as WO 99/09148, the contents of which are hereby incorporated by reference.

The present invention may be better understood by reference to the following non-limiting Examples. The following Examples are presented in order to more fully illustrate the preferred embodiments of the invention, and should in no way be construed as limiting the scope of the present invention.

EXAMPLE 1

1. Methods and Methods.

Cloning and site directed mutagenesis of RIP DD. The DNA sequence coding from amino acid 574 to 671 from hRIP (GenBank accession number U50062) was cloned in pRSETB (Invitrogen) after amplification by PCR. The primer at the 5' end introduces an initiation site with an NdeI site upstream of the methionine, and the primer at the 3' end introduces a His tag (6 histidine residues) after aa671. The sequence integrity was confirmed by sequencing analysis. Single point mutations (alanine substitutions) were introduced using a PCR-based site directed mutagenesis strategy and verified by sequencing analysis.

Protein expression and Purification. Wild-type and mutant recombinant RIP DD were prepared from *Escherichia Coli* strain BL21 (DE3) in either DM3 medium (for unlabeled protein) or DM3-minimal medium substituted with $^{15}N$ $(NH_4)_2SO_4$ (2 g/L) for $^{15}N$ labeled protein and $^{15}N$ $(NH_4)_2SO_4$ and $^{13}C$ glucose (2 g/L) for uniform double labeling ($^{15}N/^{13}C$). When cell growth reached an $OD_{595}$ of ~0.5 at room temperature, protein expression was induced by adding 0.5 mM isopropyl-1-thio-β-D-galactopyranoside for 4 hours. For the NMR samples, cells were lysed with the french press (1000 psi) in 50 mM Tris pH 8.3, 50 mM NaCl, 10 μg/mL leupeptin, 10 μg/mL aprotinin, 2 mM phenylmethylsulfonyl fluoride at 4° C. The lysates were centrifuged at 21000 g at 4° C. for 30 minutes. The majority of the RIP DD was insoluble and extracted from the pellet with a 50 mM acetate, 50 mM $MgSO_4$, 20 mM DTT, pH=4.5 buffer. The protein was purified using an anion exchange resin (Poros HQ, 50 mM acetate buffer, pH=5.2) as a flow through step followed by capture on a cation exchange resin (Poros HS). A salt gradient (0-1.5 M NaCl) was used to elute the RIP DD. The protein was further purified by gel filtration (G-2000 column) and the final NMR solution conditions were: 50 mM acetate, 250 mM NaCl, 20 mM DTT, pH=4.5.

For the mutant proteins, cells were lysed with the french press (1000 psi) in 50 mM Tris pH 7.5, 50 mM NaCl, 10 μg/mL leupeptin, 10 μg/mL aprotinin, 2 mM phenylmethylsulfonyl fluoride at 4° C. The lysates were centrifuged at 21000 g at 4° C. for 30 minutes. The soluble mutants (R603A, D613A, and E626A) were then incubated for 1 hour with Ni-NTA resin (Qiagen) at 4° C. The resin was washed twice in 50 mM Tris pH 7.5, 50 mM NaCl and twice in 50 mM Tris pH 7.5, 50 mM NaCl, 50 mM imidazole. The bound protein was eluted from the resin in 50 mM Tris pH 7.5, 50 mM NaCl, 250 mM imidazole, and 10 mM DTT was added to the eluate. The other mutants were predominately in the pellet fraction after lysis. The pellets were then washed twice in 50 mM Tris pH 8.5, 50 mM NaCl and the death domain proteins were extracted in 50 mM acetate pH 4.0, 50 mM $MgSO_4$, 10 mM DTT was then added to the extract.

NMR data collection. Data were collected at 36° C. on a Varian Unity Plus spectrometer operating at a nominal proton frequency of 600 MHz. The RIP DD concentration for NMR data collection was 0.75-1 mM unless stated otherwise. Backbone and sequential assignments were made utilizing the following pairs of triple resonance experiments: CBCA(CO)NH (Grzesiek & Bax, 1992), HNCACB (Muhandiram & Kay, 1994) and HBHA(CBCACO)NH (Grzesiek & Bax, 1993), HN(CACB)HA (Muhandiram & Kay, 1994). Sequential NOE's observed in the $^{15}N$- and $^{13}C$-edited NOESY-HSQC (Pascal et al., 1994) further confirmed the sequential assignments. Assignments were extended to the side-chain by utilizing the following experiments: C(CC)TOCSY-NNH (Grzesiek et al., 1993a), H(CC)TOCSY-NNH (Grzesiek et al., 1993a), and HCCH-TOCSY (Bax et al., 1990). Stereo-specific methylene assignments were made for five residues based upon the observed intensities in the following experiments HNHB (Archer et al., 1991), $^{15}N$-edited TOCSY-HSQC, and $^{15}N$-edited NOESY-HSQC (50 ms) (Clore & Gronenborn, 1994). Methyl groups for six out of eleven Leu residues and two out of four Val residues were stereo-specifically assigned using a combination of experiments: long range Cγ-C' (Grzesiek et al., 1993b) and long range CCJ (Bax et al., 1994; Bax et al., 1992), along with a $^{13}C$ edited NOESY-HSQC (70 ms). Data were processed with the program NMRPipe (Delaglio et al., 1995) and analyzed with the program PIPP (Garrett et al., 1991).

Structure calculations. NOE's were classified into three groups based upon intensity (1.8-2.7 Å, 1.8-3.3 Å, 1.8-5.0 Å) and pseudo atoms were corrected according to the center averaging method (Wuthrich et al., 1983). $^3J_{HNHA}$ was determined using both HNHA (Garrett et al., 1994; Vuister & Bax, 1993) and HMQC-J (Kay & Bax, 1990) experiments and for $^3J_{HNHA}$<5 Hz, the φ angle was restrained to the following range −30° to −90°, for $^3J_{HNHA}$ value in the range of 5.5-8 Hz the φ angle was restrained between −30° and −150°, and for a $^3J_{HNHA}$>9 Hz the range was −60° to −180°. The ψ torsion angle was obtained from the Talos (Cornilescu et al., 1999) program. A total of 55 ψ torsion angles were used in the helical regions and the restraint ranged from −10° to −110° and an additional 6 ψ torsion angles for non-helical regions were input and the restraint ranged from 60° to 180°. A total of 15 $\chi_1$ angles determined from the following HNHB, $^{15}$N-edited TOCSY-HSQC, and $^{15}$N-edited NOESY-HSQC (50 ms) experiments and seven $\chi_2$ angles determined from the long range Cγ-C' (Grzesiek et al., 1993b), long range CCJ (Bax et al., 1994; Bax et al., 1992), along with a $^{13}$C edited NOESY-HSQC (70 ms) were input and each angle had an error range of ±60°.

The RIP DD could not be lyophilized therefore slowly exchanging amide signals were identified from a 0.5 mM $^{15}$N-labeled sample that contained 50% H$_2$O/50% D$_2$O by monitoring the residual amide signal intensity in $^1$H-$^{15}$N HSQC spectra. Half of a RIP DD sample in H$_2$O was diluted into D$_2$O and $^1$H-$^{15}$N HSQC spectra were collected every 10 minutes for an hour and then once an hour for 24 hours. A 1 mM reference sample of RIP DD in 99.9% D$_2$O was diluted by a factor of two with a buffer containing 100% H$_2$O and a $^1$H-$^{15}$N HSQC spectrum was acquired to use as a reference for the signal intensity. Hydrogen bond constraints were input for the amide signals located in helical regions that didn't exchange in less than 30 minutes with D$_2$O. The structures were calculated using the hybrid distance geometry-dynamical simulated annealing method of Nilges (Nilges et al., 1988) using the program XPLOR (Brunger, 1994) adapted to incorporate a conformational database potential (Kuszewski et al., 1996; Kuszewski et al., 1997).

RIP DD binding assay. RIP DD binding to TRADD was determined by an enzyme-linked immunosorbent assay (ELISA). Ninety six well plates were coated overnight at 4° C. with 200 ng of MBP-TRADD, MBP-TNFR-1 DD, or MBP-IL1RacP (interleukin-1 receptor accessory protein) in coating buffer (25 mM MOPS pH 7.5, 150 mM NaCl, 10 mM DTT, 0.02% NaN$_3$). The plates were then incubated in blocking buffer (10 mM MOPS pH 7.5, 150 mM NaCl, 0.05% Tween 20, 0.1% Gelatin, 0.02% NaN$_3$) for one hour followed by one hour incubation with the different RIP DD proteins in binding buffer (100 mM Tris pH 7.5, 140 mM NaCl, 0.1 mM EDTA, 0.2% Triton X-100, 10 mM DTT). The plates were washed 4 times in 10 mM potassium phosphate buffer pH 7.4, 0.05% Tween 20. The bound His tagged proteins were then incubated for 30 minutes in 10 mM MOPS pH 7.5, 150 mM NaCl, 0.05% Tween 20, 0.02% NaN$_3$ anti-6× His biotinylated anti mouse antibody and strepavidin conjugated alkaline phosphatase. The plates were washed 4 times in 10 mM potassium phosphate buffer pH 7.4, 0.05% Tween. Tropix CDP-Star/Sapphire II solution was used for the luminescent detection of alkaline phosphatase.

2. Results.

The RIP DD has similar properties to other members of the death domain superfamily of proteins in that it forms large molecular weight aggregates at physiological pH. At pH 4.5, RIP DD is predominantly monomeric as evident by its behavior on a gel filtration column (G2000) and by 1D NMR data. The RIP DD was well behaved under the NMR conditions (50 mM acetate buffer pH 4.5, 250 mM NaCl, 20 mM DTT) allowing for 98% of the backbone and >97% of the sidechains to be assigned. A list of the $^1$H, $^{15}$N, and $^{13}$C chemical shifts for RIP DD is available as Supplementary Material.

Identification of secondary structural elements in proteins has traditionally relied upon patterns of NOE s (Wuthrich 1986) and more recently on the proton and carbon chemical shift (Wishart & Sykes, 1994; Wishart et al., 1992). FIG. 1 summarizes the secondary structural elements of the RIP DD which contains a total of five α-helices: helix 1 (residues K596-L605), helix 2 (residues Q609-D622), helix 3 (residues V628-E639), helix 4 (residues T645-Q655), and helix 5 (residues I659-L665). The N-terminus (A574-G595) of RIP DD is unstructured as indicated in FIG. 1 by the lack of deviation in the $^{13}C_\alpha$ and $^{13}C_\beta$ Chemical Shift from random coil. In addition, the observed $^3J_{HN-H\alpha}$ values were typical of an extended conformation and the amide signal for these residues completely exchanged with solvent within five minutes. The signals for the N-terminal residues in the $^1$H-$^{15}$N NOESY-HSQC and $^1$H-$^{13}$C NOESY-HSQC were truncated and the only NOEs observed for this stretch of sequence were intra-residue and sequential, indicating that this region of the protein is highly flexible and unstructured.

Structural overview. The N-terminus of RIP DD is unstructured (residues A574-L587), therefore, it was not used in the structure calculations. The structure of RIP DD encompassing residues D588-H672 was determined from a total of 954 distance constraints, 44 hydrogen bond constraints, and 140 dihedral angle constraints comprising 63 φ, constraints, 55 ψ constraints, 15 $\chi_1$ constraints, 7 $\chi_2$ constraints. The final ensemble of 21 structures contained no distance constraint violations greater than 0.25 Å and no torsion angle constraint violations greater than 3°. The NMR structures are well defined, as evident by the atomic r.m.s.d. of the 21 simulated annealing structures about the mean coordinate positions where the backbone of the helical regions and all atom in the helical region is 0.46 Å and 1.03 Å, respectively (Table 1). The RIP DD NMR structure is consistent with a good quality structure based on PROCHECK and Ramachandran analysis (Laskowski et al., 1996; Laskowski et al., 1993). A Ramachandran plot of the minimized average structure shows a total of 85.5% of the residues are in the most favored region and 13.2% in the additional allowed region, and 1.3% in the generously allowed region. PROCHECK analysis indicates an overall G-factor of 0.05 and only six bad contacts.

Figure 2:
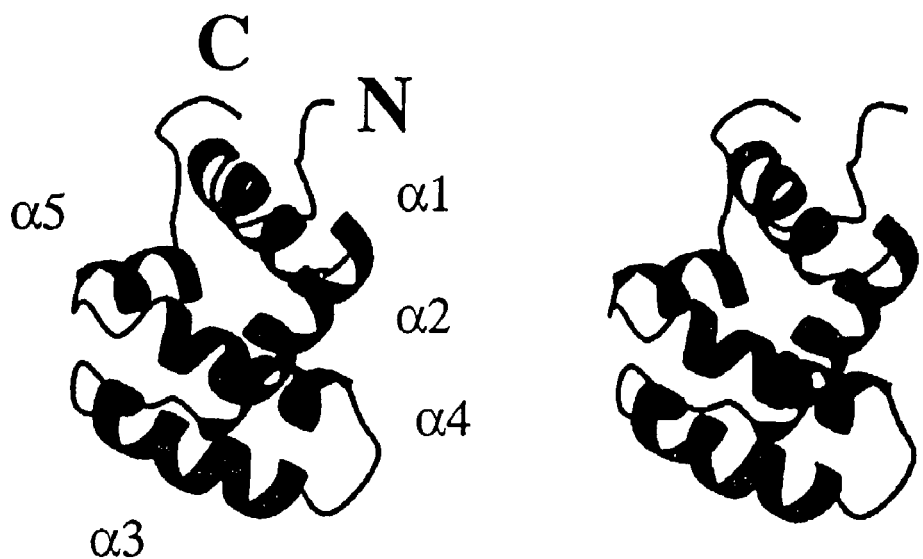
FIGS. 2A and 2B. The solution structure of RIP DD. (A) Stereo-view of the ribbon diagram of the averaged minimized structure of RIP DD. (B) Stereo-view of the $C_\alpha$, trace of an ensemble of 21 structures calculated using the program XPLOR. No structures had distance violations >0.25 Å or angle violations >3.0°.
Figure 2:
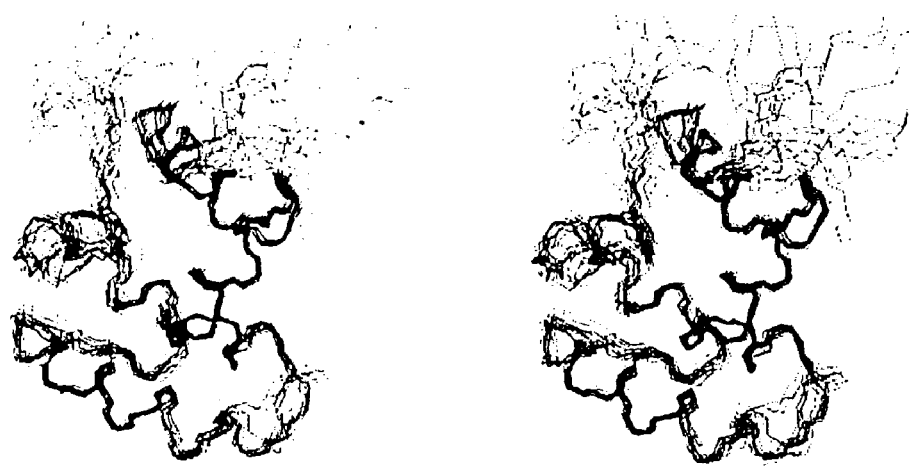
Figure 3:
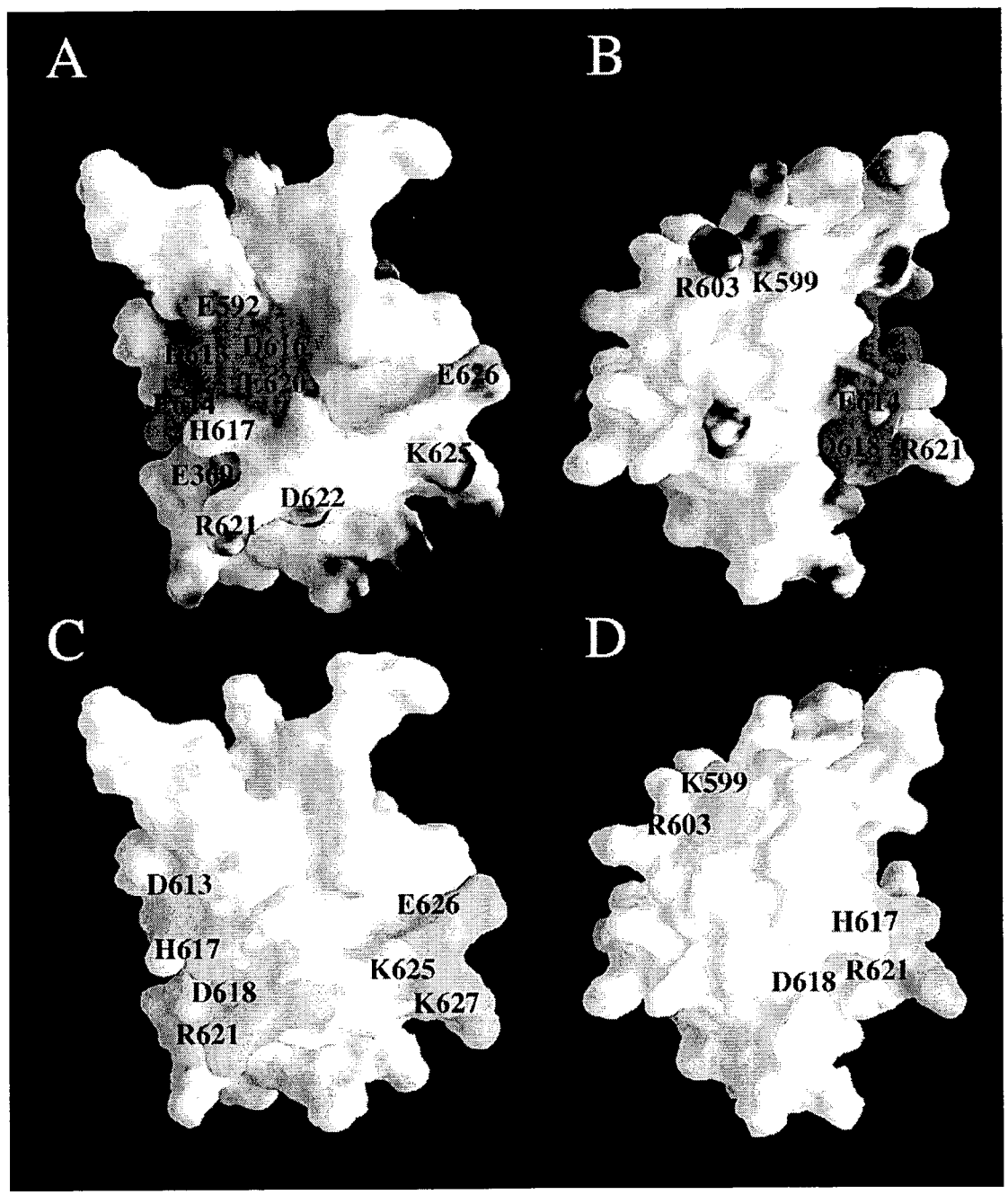
FIGS. 3A-3D. Surface diagram of RIP DD. (A) The regions of the RIP DD surface that are charged are shaded. Acidic residues from helix 2 (D613, E614, D616, and E620), the loop between helix 2 and helix 3 (D622), and helix 3 (E639) come together to form an acidic patch. (B) The RIP DD surface is rotated 120° about the z-axis from (A). (C&D) Mutations that reduce the binding affinity to TRADD are labeled. The surface of (C) is in the same orientation as (A) and the surface of (D) is in the same orientation as (B).

The RIP DD contains 5 amphipathic α-helices (FIGS. 2A and 2B) where the sidechains of the hydrophobic residues in the helices form an extensive network of interactions that constitute the core of the protein. Helices 1 and 3 are aligned parallel to each other and helix 2, which is the longest helix, spans the length of one side of the protein and is aligned almost perpendicular to helices 1 and 3. Helices 4 and 5 are aligned anti-parallel to each other and are bisected by helix 2. The surface of RIP DD contains several charged residues (FIGS. 3A and 3B). Several acidic residues cluster together to form an acidic patch composed of residues originating from helix 2 (D613, E614, D616, and E620), the loop between helix 2 and helix 3 (D622), and helix 3 (E639). The surface of RIP DD contains two regions of the protein that contain solvent exposed hydrophobic residues (data not shown). One site contains residues from the N- and C-terminus (I590, L594, and I666) and the other contains residues from helix 3 (Y629, M631, and W635).

Figure 4:
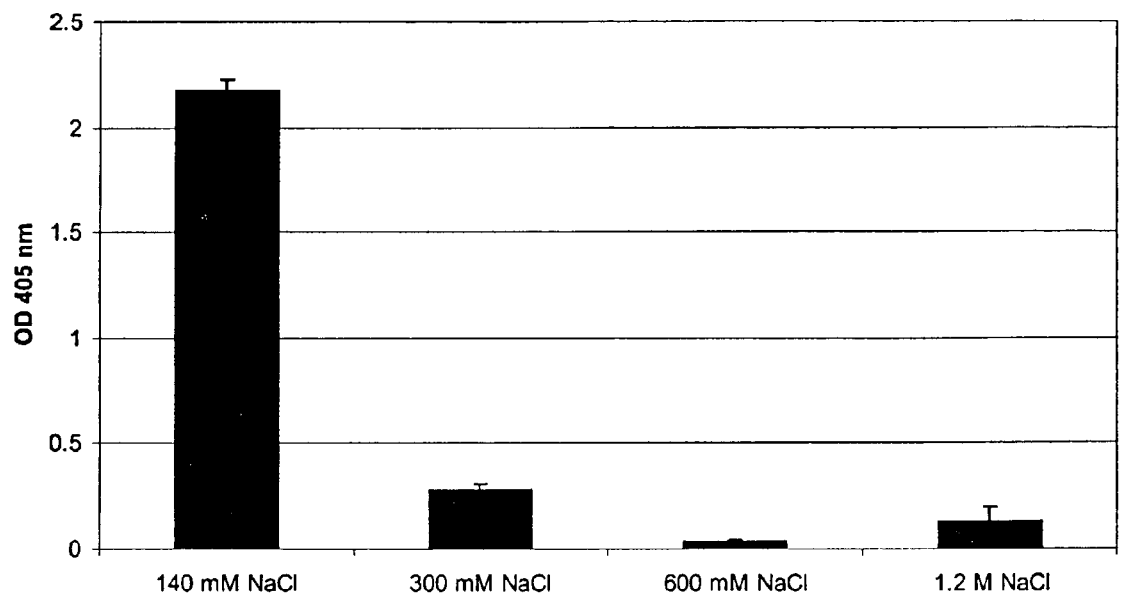
FIGS. 4A and 4B. (A) Effect of the ionic strength on the binding of RIP-DD (30 μg/mL) to MBP-TRADD. (B) ELISA of RIP-DD binding to MBP-TRADD. MBP-TRADD was immobilized at 500 ng/well on 96 well plates. The reference at 100% is the binding of the wild type protein to MBP-TRADD. The values used for the determination of the binding percentage were obtained with ~30 μg/ml of soluble protein.
Figure 4:
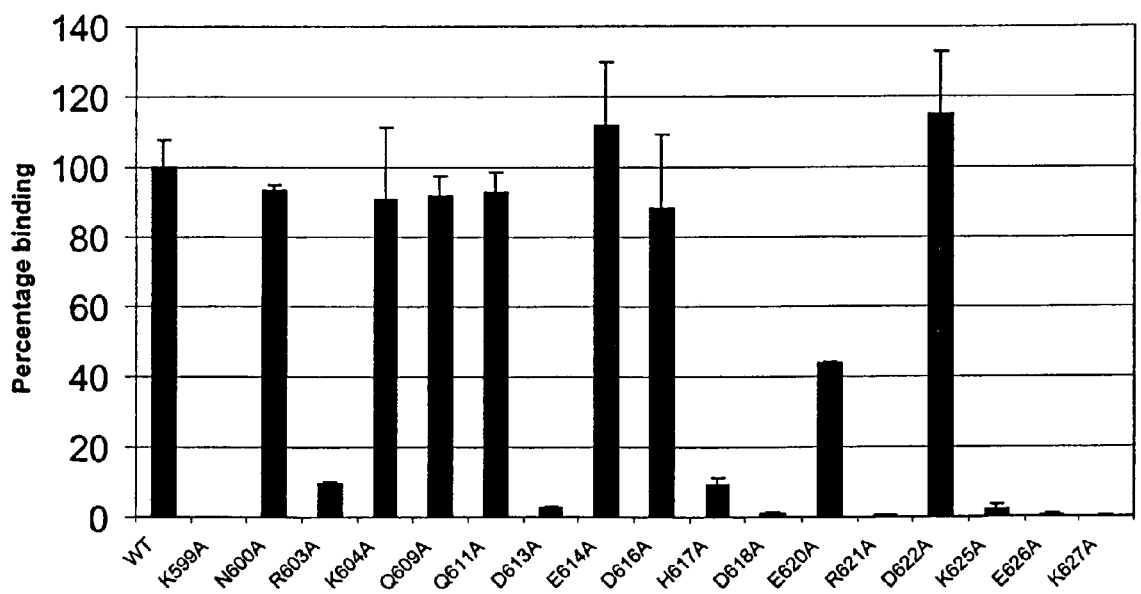
Figure 5:
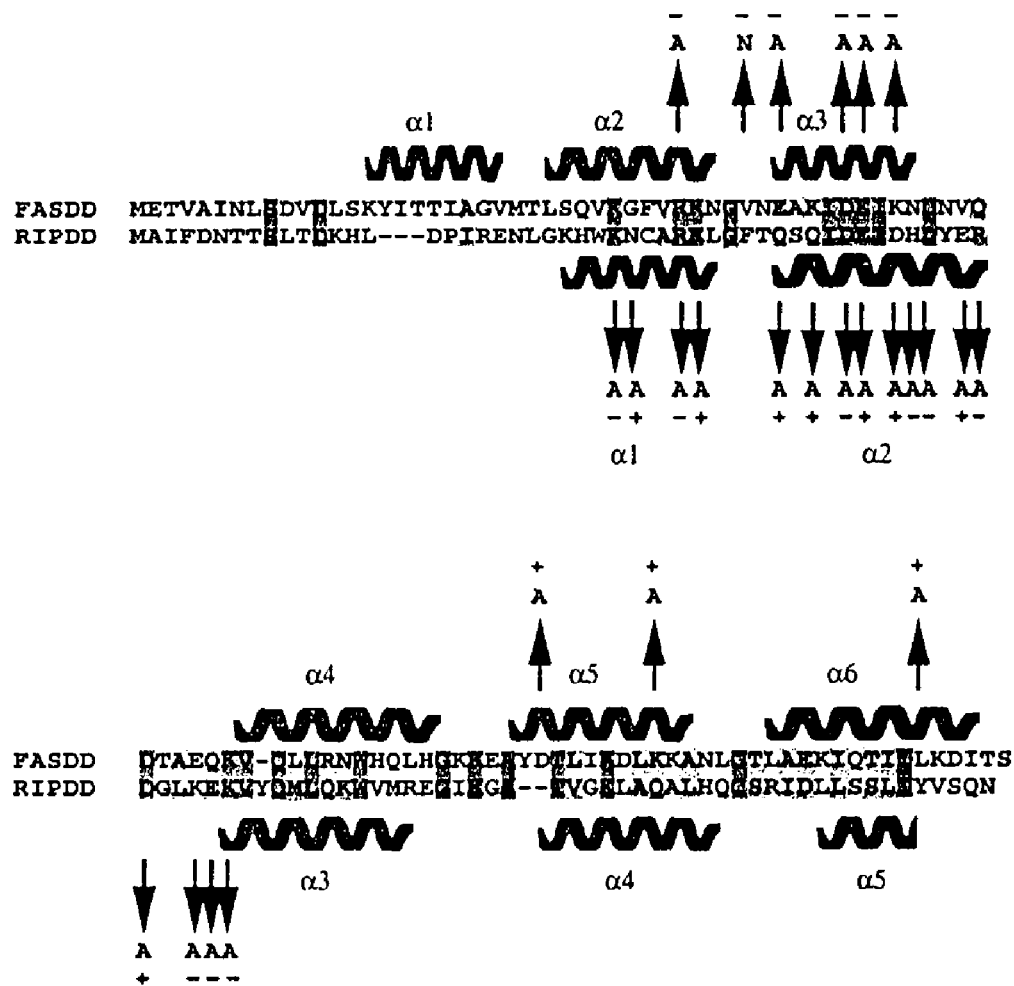
FIG. 5. Sequence alignment of the death domains of FAS (SEQ ID NO:2) and RIP (SEQ ID NO:3). Identical residues and homologous residues are shaded. The helices identified from the NMR structure of FAS DD (Huang et al., 1996) are located above the sequence and the helices identified from the NMR structure of RIP DD are located below the sequence. The mutations are indicated by an arrow pointing to the amino acid residue of substitution. A minus sign above the FAS mutation indicates that this mutant aggregates less than the wild-type protein (Huang et al., 1996). A minus sign below the RIP DD mutation indicates reduced binding to TRADD.

Effect of RIP-DD single point mutations on interaction with TRADD DD. A structure/function study of the FAS DD identified critical charged residues located in helix 2, the loop between helix 2 and helix 3, and helix 3 that when mutated altered the ability of the protein to self-associate and to bind to FADD DD (Huang et al., 1996). Similar key charged residues were also identified for the FADD DD (Jeong et al., 1999) and TNFR-1 DD (Telliez et al., 2000) implying that electrostatic interactions may be important for this protein interaction motif. To determine if the mode of interaction between the RIP DD and TRADD DD is electrostatic in nature a salt titration was performed. Increasing concentrations of NaCl decreased the association between the RIP DD and TRADD (FIG. 4A). Based on these results, five conserved charged residues (R603, D613, E614, D616, and E626) of RIP DD were mutated to Ala according to a sequence alignment with the FAS DD (FIG. 5). After characterization of the five mutants, two different regions of the surface of RIP DD were identified that disrupted binding to TRADD. To further characterize the potential binding sites an additional twelve solvent exposed charged residues were mutated to Ala. In all, a total of seventeen amino acids were mutated to alanine (FIG. 5). The amino acid alanine was for the mutational analysis since it eliminates the contribution from the side chain while potentially minimizing any alteration in the overall protein structure.

All the RIP DD mutants depicted in FIG. 5 were studied for their ability to interact with TRADD. The full-length TRADD protein was expressed as a MBP fusion (MBP-TRADD) and was immobilized on 96 well plates for ELISA. Mutation of K599A and R603A of helix 1 abolished the interaction with TRADD while mutation of N600A and K604A of helix 1 retained binding properties similar to the wild-type protein (FIG. 4B). Additionally, mutation of D613A, H617A, D618A, and R621A of helix 2 all diminish binding to TRADD whereas Q611A, E614A, D616A, E620A, and D622A all retain binding properties similar to the wild-type protein. Mutation of three charged residues (K625A, E626A, and K627A) in the loop between helix 2 and helix 3 all abolished binding to TRADD. The mutations that abolished binding with TRADD were mapped onto the surface of RIP DD as illustrated in FIGS. 3C and 3D. The mutations that abolished the interaction of RIP DD with TRADD cluster on two distinct regions of the RIP DD surface. One face of the protein contains mutations from helix 2 (D613A, H617A, D618A, and R621A) and the loop between helix 2 and helix 3 (K625A, E626A, and K627A) FIG. 3C, and the other face contains residues from helix 1 (K599A and R603A) FIG. 3D.

3. Discussion.

Sequence alignments among various pairs of death domains have shown that typically there is ~20% sequence identity (Feinstein et al., 1995; Hofmann, 1999). Using FAS DD as a representative example of the other death domains with known structures, a sequence alignment with RIP DD (FIG. 5) indicates that twenty-four residues are identical and half of these identical residues are charged. Likewise, several residues containing sequence similarity are also charged. The secondary structure content of RIP DD (FIG. 1 and FIG. 5) is helical, which is consistent with the other members of the death domain superfamily; however, RIP DD contains a core of five α-helices whereas the other death domain family members contain a core of six α-helices. A comparison of the secondary structure shows that helices 1-5 of the RIP DD align well with helices 2-6 of the FAS DD even though there are slight differences in helix length (FIG. 5). Nevertheless, a comparison of the overall topology between FAS DD and RIP DD reveals significant differences between the two proteins. The most striking difference is that the first helix in FAS DD is apparently missing in the RIP DD structure based upon the sequence alignment (FIG. 5). Furthermore, an attempt to superimpose the FAS DD with the RIP DD based upon the sequence alignment yielded structures that only superimposed well on individual helices and not on the overall fold. An attempt to superimpose the two structures based upon a secondary structure alignment resulted in a poor overlay of the global fold as well. The best overlay of the two structures resulted from a structural overlay where only four of the α-helices were reasonably aligned (not shown). This overlay matched helix 1 of RIP DD with helix 1 of FAS DD, helix 2 of RIP DD with helix 4 of FAS DD, helix 3 of RIP DD with helix 5 of FAS DD, and helix 4 of RIP DD with helix 6 of FAS DD. The remaining helices that didn't superimpose based upon this structural alignment were the C-terminal helix 5 of RIP DD and helices 2 and 3 of the FAS DD. Interestingly, helices 2 and 3 of the FAS DD have been shown to be critical for self-aggregation and interaction with the FADD DD. These results suggest that the overall topology of RIP DD represents a novel fold for the death domain superfamily of proteins which may be responsible for unique binding properties of this protein (ie. interactions with TRADD and RAIDD).

Similar to many of the proteins in the death domain superfamily, RIP DD contains a charged surface (FIGS. 3A and 3B) where titration with NaCl disrupted the interaction between RIP DD and TRADD indicating that the homotypic interaction is at least in part electrostatic (FIG. 4A). The electrostatic interaction between RIP DD and TRADD is consistent with the proposed interactions of FAS DD with FADD DD (Jeong et al., 1999) and of TNFR-1 DD with TRADD DD (Telliez et al., 2000). Mutagenesis studies carried out on FAS DD (Huang et al., 1996) indicated that the region of the protein that is important for both self-aggregation and interaction with FADD DD are located in helix 2, in the loop between helix 2 and helix 3, and in helix 3. An analogous study of FADD DD (Jeong et al., 1999) found that mutation of charged residues in helices 2 and 3 disrupted binding with FAS DD and disrupted the interactions necessary for self-association. In both cases, the residues that were mutated and affected binding between FAS DD and FADD DD were charged residues. According to most published sequence alignments of the death domains, (Feinstein et al., 1995; Hofmann, 1999) some of the residues of FAS DD that abolished binding with FADD (helices 2 and 3) are conserved in RIP DD (Huang et al., 1996) (FIG. 5). Prior to the availability of the RIP DD structure, a series of single-point mutants of RIP DD (R603A, D613A, E614A, D616A, and E626A) were made based upon the results of the mutagenesis study of FAS DD (Huang et al., 1996) (FIG. 5) in an attempt to identify the RIP DD binding surface with TRADD. Once the RIP DD structure was determined and compared to FAS DD it was clear that the global fold of RIP DD was novel among the death domain superfamily. Therefore, an additional twelve surface exposed charged residues were identified as part of a potential binding surface with TRADD and mutated. Mutations of charged residues in helix 1, helix 2, and the loop between helix 2 and helix 3 of RIP DD disrupt association with TRADD which suggest the identification of the major binding sites on RIP DD. The RIP DD mutations that abolished binding with TRADD cluster in two main regions as illustrated in FIGS. 3C and 3D. One cluster contains mutated residues from helix 2 (D613A, H617A, D618A, and R621A) and the loop between helix 2 and helix 3 (K625A, E626A, and K627A) FIG. 3C, and the other cluster contains residues from helix 1 (K599A and R603A) in FIG. 3D.

RIP is recruited to the TNFR-1 complex through a death domain/death domain interaction with TRADD. Our results for the interaction between RIP DD and TRADD DD are consistent with the proposed idea that the interaction between TNFR-1 DD and TRADD DD (Telliez et al., 2000) is at least in part electrostatic indicating that the surface of TRADD DD is charged. This is similar to the proposed interactions between FAS DD (Huang et al., 1996) with FADD DD (Jeong et al., 1999) and TNFR-1 DD with TRADD DD (Telliez et al., 2000). The stoichiometry of the complex between RIP DD and TRADD DD is unknown at this time. However, mutagenesis studies have identified two distinct regions on the surface of RIP DD that are spatially distributed on opposite faces (~120° rotation) of the protein. This implies that there are at least two TRADD DD binding sites on RIP DD suggesting that RIP DD might make contact with at least two TRADD molecules in the TNFR-1 complex.

The solution structure of RIP DD reveals a novel three-dimensional organization relative to other members of the death domain family. The difference in the overall structure of RIP DD could explain the specificity of its interaction with other death domains such as TRADD DD and RAIDD. Additionally, mutagenesis studies have identified two distinct sites on the surface of the RIP DD that alter the binding affinity for the TRADD protein, implying that there may be two TRADD DD binding sites on RIP DD. The RIP DD surface corresponding to the TRADD DD binding site is composed of charged residues suggesting a complimentary surface on TRADD DD and a binding interaction that is primarily electrostatic in nature.

TABLE I

Structural, Energetic Statistics and Atomic rms Differences

Structural and Energetic Statistics

| | <SA> | (SA)r |
|---|---|---|
| rms deviations from exptl distance restraints (Å) (954) | 0.0101 ± 0.001 | 0.0058 |
| No. of distance restraint violations greater than 0.25 Å | 0 | 0 |
| rms deviations from exptl dihedral restraints (deg) (92) | 0.1156 ± 0.09 | 0.0500 |
| No. of dihedral restraint violations greater than 3 (deg) | 0 | 0 |
| rms deviations from idealized covalent geometry | | |
| bonds (Å) | 0.0028 ± 0.0004 | 0.0013 |
| angles (deg) | 0.341 ± 0.023 | 0.2016 |
| impropers (deg) | 0.299 ± 0.0182 | 0.1824 |
| Energetics | | |
| $E_{repel}$ (kcal mol$^{-1}$) | 13 ± 3 | 8.0 |
| $E_{NOE}$ (kcal mol$^{-1}$) | 5 ± 2 | 1.6 |
| $E_{cdih}$ (kcal mol$^{-1}$) | 0.18 ± 0.29 | 0.02 |
| $E_{bond}$ (kcal mol$^{-1}$) | 11.3 ± 3.5 | 2.3 |
| $E_{imp}$ (kcal mol$^{-1}$) | 10.0 ± 1 | 3.7 |
| $E_{ang}$ (kcal mol$^{-1}$) | 44.8 ± 5 | 16 |
| Procheck[a] | | |
| residues in most favorable region of Ramachandran plot | 94.7 ± 0.4 | 85.5 |
| residues in additionally allowed region of Ramachandran plot | 4.4 ± 0.3 | 13.2 |
| residues in generously allowed region of Ramachandran plot | 0.5 ± 0.1 | 1.3 |
| residues in disallowed region of Ramachandran plot | 0.4 ± 0.1 | 0 |
| overall G-factor | 0.28 ± 0.01 | 0.05 |
| no of bad contacts | 3.6 ± 1.7 | 6 |

Non-hydrogen Atomic rms Differences (Å)

| | All residues[b] | | Secondary structure[c] | |
|---|---|---|---|---|
| | backbone atoms | all atoms | backbone atoms | all atoms |
| <SA> vs SA | 1.66 ± 0.29 | 2.25 ± 0.24 | 0.46 ± 0.09 | 1.03 ± 0.08 |
| <SA> vs (SA)r | 1.82 ± 0.31 | 2.53 ± 0.32 | 0.52 ± 0.09 | 1.15 ± 0.09 |
| (SA)r vs SA | 0.77 | 1.19 | 0.24 | 0.53 |

The NMR structures are denoted as follows: <SA> are the final 21 ensemble structures; SA is the mean structure obtained from averaging the cartesian coordinates of individual ensemble members; and (SA)r is the minimized average structure obtained by regularization of SA. $E_{repel}$ was calculated using a final force constant of 4.0 kcal mol$^{-1}$ Å$^{-4}$ with van der Waals hard sphere radii scaled by 0.78. $E_{NOE}$ was calculated using a square-well potential with center-averaging and a force constant of 50 kcal mol$^{-1}$ Å$^{-2}$. $E_{cdih}$ was calculated using a force constant of 200 kcal mol$^{-1}$ rad$^{-2}$. $E_{bond}$, $E_{angle}$ and $E_{improper}$ were calculated using force constants of 1000 kcal mol$^{-1}$ Å$^{-2}$, 500 kcal mol$^{-1}$ rad$^{-2}$ and 500 kcal mol$^{-1}$ rad$^{-2}$, respectively.
[a]These were calculated using the PROCHECK program (Laskowski et al., 1996; Laskowski et al., 1993).
[b]In all atomic rms differences calculations, only the backbone atoms (N, $C_\alpha$ and C) are included in the least squared best fitting.
[c]Core five helices.

REFERENCES

Archer, S. J., Ikura, M., Torchia, D. A. & Bax, A. (1991). An alternative 3D NMR technique for correlating backbone $^{15}$N with side chain Hβ resonances in larger proteins. *J. Magn. Reson.* 95(3), 636-41.

Bax, A., Clore, G. M. & Gronenborn, A. M. (1990). Proton-proton correlation via isotropic mixing of $^{13}$C magnetization, a new three-dimensional approach for assigning proton and $^{13}$C spectra of $^{13}$C-enriched proteins. *J. Magn. Reson.* 88(2), 425-31.

Bax, A., Delaglio, F., Grzesiek, S. & Vuister, G., W. (1994). Resonance assignment of methionine methyl groups and χ3 angular information from long-range proton-carbon and carbon-carbon J correlation in a calmodulin-peptide complex. *J. Biomol. NMR* 4, 787-797.

Bax, A., Max, D. & Zax, D. (1992). Measurement of long-range $^{13}$C-$^{13}$C J couplings in a 20-kDa protein-peptide complex. *J. Am. Chem. Soc.* 114, 6924-6924.

Brunger, A. T. (1993). *X-PLOR Version 3.1 Manual*, Yale University, New Haven, USA, Conn.

Chan, F. K., Chun, H. J., Zheng, L., Siegel, R. M., Bui, K. L. & Lenardo, M. J. (2000). A domain in TNF receptors that mediates ligand-independent receptor assembly and signaling. *Science* 288(5475), 2351-4.

Chou, J. J., Matsuo, H., Duan, H. & Wagner, G. (1998). Solution structure of the RAIDD CARD and model for CARD/CARD interaction in caspase-2 and caspase-9 recruitment. *Cell* 94(2), 171-80.

Clore, G. M. & Gronenborn, A. M. (1994). Multidimensional heteronuclear nuclear magnetic resonance of proteins. *Methods Enzymol.* 239, 349-362.

Cornilescu, G., Delaglio, F. & Bax, A. (1999). Protein backbone angle restraints from searching a database for chemical shift and sequence homology. *J Biomol. NMR* 13(3), 289-302.

Delaglio, F., Grzesiek, S., Vuister, G. W., Zhu, G., Pfeifer, J. & Bax, A. (1995). NMRPipe: a multidimensional spectral processing system based on UNIX pipes. *J. Biomol. NMR* 6(3), 277-93.

Duan, H. & Dixit, V. M. (1997). RAIDD is a new 'death' adaptor molecule. *Nature* 385(6611), 86-9.

Eberstadt, M., Huang, B., Chen, Z., Meadows, R. P., Ng, S. C., Zheng, L., Lenardo, M. J. & Fesik, S. W. (1998). NMR structure and mutagenesis of the FADD (Mort1) death-effector domain. *Nature* 392(6679), 941-5.

Feinstein, E., Kimchi, A., Wallach, D., Boldin, M. & Varfolomeev, E. (1995). The death domain: a module shared by proteins with diverse cellular functions. *Trends Biochem. Sci.* 20(9), 342-4.

Garrett, D. S., Kuszewski, J., Hancoca, T. J., Lodi, P. J., Vuister, G. W., Gronenborn, A. M. & Clore, G. M. (1994). The impact of direct refinement against three-bond HN-CaH coupling constants on protein structure determination by NMR. *J. Magn. Reson., Ser. B* 104, 99-103.

Garrett, D. S., Powers, R., Gronenborn, A. M. & Clore, G. M. (1991). A common sense approach to peak picking in two-, three-, and four dimensional spectra using automatic computer analysis of contour diagrams. *J. Magn. Reson.* 95, 214-220.

Grell, M., Scheurich, P., Meager, A. & Pfizenmaier, K. (1993). TR60 and TR80 tumor necrosis factor (TNF)-receptors can independently mediate cytolysis. *Lymphokine Cytokine Res.* 12(3), 143-8.

Grzesiek, S., Anglister, J. & Bax, A. (1993a). Correlation of backbone amide and aliphatic side-chain resonances in $^{13}C/^{15}N$ enriched proteins by isotropic mixing of $^{13}C$ magnetization. *J. Magn. Reson., Ser. B* 101(1), 114-19.

Grzesiek, S. & Bax, A. (1992). Correlating backbone amide and side chain resonances in larger proteins by multiple relayed triple resonance NMR. *J. Am. Chem. Soc* 114(16), 6291-3.

Grzesiek, S. & Bax, A. (1993). Amino acid type determination in the sequential assignment procedure of uniformity $^{13}C/^{15}N$ enriched proteins. *J. Biomol. NMR* 3(2), 185-204.

Grzesiek, S., Vuister, G. W. & Bax, A. (1993b). A simple and sensitive experiment for measurement of $J_{cc}$ couplings between backbone carbonyl and methyl carbons in isotopically enriched proteins. *J. Biomol. NMR* 3(4), 487-93.

Hofmann, K. (1999). The modular nature of apoptotic signaling proteins. *Cell Mol. Life Sci.* 55(8-9), 1113-28.

Hsu, H., Huang, J., Shu, H. B., Baichwal, V. & Goeddel, D. V. (1996a). TNF-dependent recruitment of the protein kinase RIP to the TNF receptor-1 signaling complex. *Immunity* 4(4), 387-96.

Hsu, H., Shu, H. B., Pan, M. G. & Goeddel, D. V. (1996b). TRADD-TRAF2 and TRADD-FADD interactions define two distinct TNF receptor 1 signal transduction pathways. *Cell* 84(2), 299-308.

Hsu, H., Xiong, J. & Goeddel, D. V. (1995). The TNF receptor 1-associated protein TRADD signals cell death and NF-kappa B activation. *Cell* 81(4), 495-504.

Huang, B., Eberstadt, M., Olejniczak, E. T., Meadows, R. P. & Fesik, S. W. (1996). NMR structure and mutagenesis of the Fas (APO-1/CD95) death domain. *Nature* 384(6610), 638-41.

Jeong, E. J., Bang, S., Lee, T. H., Park, Y. I., Sim, W. S. & Kim, K. S. (1999). The solution structure of FADD death domain. Structural basis of death domain interactions of Fas and FADD. *J. Biol. Chem.* 274(23), 16337-42.

Kay, L. E. (1995). Pulsed field gradient multi-dimensional NMR methods for the study of protein structure and dynamics in solution. *Prog. Biophys. Mol. Biol.* 63, 277-99.

Kay, L. E. & Bax, A. (1990). New methods for the measurement of NH-CαH coupling constants in $^{15}N$-labeled proteins. *J. Magn. Reson.* 86, 110-126.

Kelliher, M. A., Grimm, S., Ishida, Y., Kuo, F., Stanger, B. Z. & Leder, P. (1998). The death domain kinase RIP mediates the TNF-induced NF-kappaB signal. *Immunity* 8(3), 297-303.

Kuszewski, J., Gronenborn, A. M. & Clore, G. M. (1996). Improving the quality of NMR and crystallographic protein structures by means of a conformational database potential derived from structure databases. *Protein Sci.* 5(6), 1067-80.

Kuszewski, J., Gronenbom, A. M. & Clore, G. M. (1997). Improvements and extensions in the conformational database potential for the refinement of NMR and X-ray structures of proteins and nucleic acids. *J. Magn. Reson.* 125(1), 171-7.

Laskowski, R., Rullmannn, J., MacArthur, M., Kaptein, R. & J M, T. (1996). AQUA and PROCHECK-NMR: programs for checking the quality of protein structures solved by NMR. *J. Biomol. NMR* 8(4), 477-486.

Laskowski, R. A., MacArthur, M. W., Moss, D. S. & Thornton, J. M. (1993). PROCHECK: a program to check the stereochemical quality of protein structures. *J. Appl. Crystallogr.* 26, 283-291.

Liepinsh, E., Ilag, L. L., Otting, G. & Ibanez, C. F. (1997). NMR structure of the death domain of the p75 neurotrophin receptor. *Embo J.* 16(16), 4999-5005.

Muhandiram, D. R. & Kay, L. E. (1994). Gradient-Enhanced Triple-Resonance Three-Dimensional NMR Experiments with Improved Sensitivity. *J. Magn. Reson., Ser. B* 103, 208-216.

Nilges, M., Clore, G. M. & Gronenborn, A. M. (1988). Determination of three-dimensional structures of proteins from interproton distance data by hybrid distance geometry-dynamical simulated annealing calculations. *FEBS Lett.* 229(2), 317-24.

Pascal, S. M., Muhandiram, D. R., Yamazaki, T., Forman-Kay, J. D. & Kay, L. E. (1994). Nuclear magnetic resonance structure of an SH2 domain of phospholipase C-g 1 complexed with a high affinity binding peptide. *J. Magn. Reson.* 103, 197-201.

Qin, H., Srinivasula, S. M., Wu, G., Fernandes-Alnemri, T., Alnemri, E. S. & Shi, Y. (1999). Structural basis of procaspase-9 recruitment by the apoptotic protease-activating factor 1. *Nature* 399(6736), 549-57.

Smith, C. A., Farrah, T. & Goodwin, R. G. (1994). The TNF receptor superfamily of cellular and viral proteins: activation, costimulation, and death. *Cell* 76(6), 959-62.

Stanger, B. Z., Leder, P., Lee, T. H., Kim, E. & Seed, B. (1995). RIP: a novel protein containing a death domain that interacts with Fas/APO-1 (CD95) in yeast and causes cell death. *Cell* 81(4), 513-23.

Sukits, et al. (2001). Solution Structure of the Tumor Necrosis Factor Receptor-1 Death Domain. *J. Mol. Biol.* 310(4), 895-906.

Tartaglia, L. A. & Goeddel, D. V. (1992). Two TNF receptors. *Immunol. Today* 13(5), 151-3.

Tartaglia, L. A., Rothe, M., Hu, Y. F. & Goeddel, D. V. (1993). Tumor necrosis factor's cytotoxic activity is signaled by the p55 TNF receptor. *Cell* 73(2), 213-6.

Telliez, J. B., Xu, G. Y., Woronicz, J. D., Hsu, S., Wu, J. L., Lin, L., Sukits, S. F., Powers, R. & Lin, L. L. (2000). Mutational Analysis and NMR studies of the Death Domain of the Tumor Necrosis Factor Receptor-1. *J. Mol. Biol.* 300(5), 1323-1333.

Vuister, G. W. & Bax, A. (1993). Quantitative J correlation: a new approach for measuring homonuclear three-bond J(HN-Hα) coupling constants in $^{15}$N-enriched proteins. *J. Am. Chem. Soc.* 115, 7772-7777.

Wishart, D. S. & Sykes, B. D. (1994). The $^{13}$C chemical-shift index: a simple method for the identification of protein secondary structure using $^{13}$C chemical-shift data. *J. Biomol. NMR* 4(2), 171-80.

Wishart, D. S., Sykes, B. D. & Richards, F. M. (1992). The chemical shift index: a fast and simple method for the assignment of protein secondary structure through NMR spectroscopy. *Biochemistry* 31(6), 1647-51.

Wuthrich, K., Billeter, M. & Braun, W. (1983). Pseudo-structures for the 20 common amino acids for use in studies of protein conformations by measurements of intramolecular proton-proton distance constraints with nuclear magnetic resonance. *J. Mol. Biol.* 169(4), 949-61.

Xiao, T., Towb, P., Wasserman, S. A. & Sprang, S. R. (1999). Three-dimensional structure of a complex between the death domains of Pelle and Tube. *Cell* 99(5), 545-55.

Zhou, P., Chou, J., Olea, R. S., Yuan, J. & Wagner, G. (1999). Solution structure of Apaf-1 CARD and its interaction with caspase-9 CARD: a structural basis for specific adaptor/caspase interaction. *Proc. Natl. Acad. Sci. USA* 96(20), 11265-70.

All publications mentioned herein above, whether to issued patents, pending applications, published articles, protein structure deposits, or otherwise, are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for identifying an agent that inhibits Receptor Interacting Protein death domain (RIP DD), comprising:
   providing a solution comprising RIP DD;
   determining the three dimensional structure of RIP DD in the solution;
   identifying an active site of RIP DD from the three dimensional structure of RIP DD, wherein the three dimensional structure comprises the relative structural coordinates of RIP DD as represented in FIGS. 6 to 6A-38, ± a root mean square deviation from the backbone atoms of RIP DD of not more than 1.5 Å; and
   performing computer fitting analysis to identify an agent which inhibits said active site.

2. The method of claim 1, wherein the ± a root mean square deviation from the backbone atoms of RIP DD is not more than 1.0 Å.

3. The method of claim 1, wherein the ± a root mean square deviation from the backbone atoms of RIP DD is not more than 0.5 Å.

4. The method of claim 1, further comprising contacting the identified agent with a RIP DD and determining the effect the agent has on RIP DD activity.

5. The method of claim 4, wherein the agent inhibits RIP DD activity.

6. The method of claim 1, further comprising contacting the identified agent with a RIP DD in the presence of a RIP DD binding molecule, and determining the effect the agent has on binding of the RIP DD to the RIP DD binding molecule.

7. The method of claim 1, wherein the structure is determined using NMR spectroscopy.

8. The method of claim 1, wherein RIP DD comprises amino acid residues K596-L605 (α1 helix), amino acid residues Q609-D622 (α2 helix), amino acid residues V628-E639 (α3 helix), amino acid residues T645-Q655 (α4 helix) of RIP DD, and amino acid residues I659-L665 (α3 helix), of FIG. 1 (SEQ ID NO:1), or conservative substitutions thereof.

9. The method of claim 1, wherein RIP DD comprises amino acid residues 574-671 of FIG. 1 (SEQ ID NO:1), or conservative substitutions thereof.

10. The method of claim 1, further comprising storing the three-dimensional structure of the active site of RIP DD in a machine readable storage medium.

11. The method of claim 1, further comprising displaying the three dimensional structure of RIP DD.

12. A method for identifying an agent that inhibits Receptor Interacting Protein death domain (RIP DD), comprising:
   providing a solution comprising RIP DD;

determining the three dimensional structure of RIP DD in the solution;

identifying an active site of RIP DD from the three dimensional structure of RIP DD, wherein the active site comprises the relative structural coordinates of amino acid residues D6 13, H617, D618, R621, K625, E626 and K627 according to FIGS. 6 to 6A-38, ± a root mean square deviation from the backbone atoms of RIP DD of not more than 1.5 Å.

13. The method of claim 12, wherein the ± a root mean square deviation from the backbone atoms of RIP DD is not more than 1.0 Å.

14. The method of claim 12, wherein the ± a root mean square deviation from the backbone atoms of RIP DD is not more than 0.5 Å.

15. The method of claim 12, wherein the active site further comprises the relative structural coordinates of amino acid residues K599 and R603 according to FIGS. 6 to 6A-38, ± a root mean square deviation from the backbone atoms of RIP DD is not more than 1.5 Å.

16. The method of claim 15, wherein the ± a root mean square deviation from the backbone atoms of RIP DD is not more than 1.0 Å.

17. The method of claim 15, wherein the ± a root mean square deviation from the backbone atoms of RIP DD is not more than 0.5 Å.

18. The method of claim 12, wherein RIP DD comprises amino acid residues K596-L605 (α1 helix), amino acid residues Q609-D622 (α2 helix), amino acid residues V628-E639 (α3 helix), amino acid residues T645-Q655 (α4 helix) of RIP DD, and amino acid residues I659-L665 (α3 helix), of FIG. 1 (SEQ ID NO:1), or conservative substitutions thereof.

19. The method of claim 12, wherein RIP DD comprises amino acid residues 574-671 of FIG. 1 (SEQ ID NO:1), or conservative substitutions thereof.

20. The method of claim 12, further comprising storing the three-dimensional structure of the active site of RIP DD in a machine readable storage medium.

21. The method of claim 12, further comprising displaying the three dimensional structure of RIP DD.

* * * * *